(12) United States Patent
Pushkarev et al.

(10) Patent No.: US 9,725,765 B2
(45) Date of Patent: Aug. 8, 2017

(54) METHODS FOR OBTAINING A SEQUENCE

(75) Inventors: Dmitry Pushkarev, Stanford, CA (US);
Stephen R. Quake, Stanford, CA (US);
Ayelet Voskoboynik, Aptos, CA (US);
Michael Kertesz, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/608,770

(22) Filed: Sep. 10, 2012

(65) Prior Publication Data
US 2013/0157870 A1 Jun. 20, 2013

Related U.S. Application Data

(60) Provisional application No. 61/532,882, filed on Sep. 9, 2011.

(51) Int. Cl.
*C12Q 1/68* (2006.01)

(52) U.S. Cl.
CPC ......... *C12Q 1/6874* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

| | | |
|---|---|---|
| 5,614,389 A | 3/1997 | Auerbach |
| 5,733,733 A | 3/1998 | Auerbach |
| 5,849,558 A | 12/1998 | Morgan et al. |
| 5,888,737 A | 3/1999 | DuBridge et al. |
| 5,945,326 A | 8/1999 | Morgan et al. |
| 6,030,830 A | 2/2000 | Saxon et al. |
| 6,048,719 A | 4/2000 | Kong et al. |
| 6,048,731 A | 4/2000 | Kong et al. |
| 6,060,245 A | 5/2000 | Sorge et al. |
| 6,074,831 A | 6/2000 | Yakhini et al. |

(Continued)

FOREIGN PATENT DOCUMENTS

| | | |
|---|---|---|
| EP | 0359714 B1 | 3/1990 |
| EP | 0869174 B1 | 10/1998 |

(Continued)

OTHER PUBLICATIONS

Browning, et al. Rapid and Accurate Haplotype Phasing and Missing-Data Inference for Whole-Genome Association Studies by Use of Localized Haplotype Clustering. Am J Hum Genet. Nov. 2007;81(5):1084-97. Epub Sep. 21, 2007.

(Continued)

*Primary Examiner* — Kaijiang Zhang
(74) *Attorney, Agent, or Firm* — Knobbe, Martens, Olson & Bear, LLP

(57) ABSTRACT

The invention generally relates to methods for obtaining a sequence, such as a consensus sequence or a haplotype sequence. In certain embodiments, methods of the invention involve determining an amount of amplifiable nucleic acid present in a sample, partitioning the nucleic acid based upon results of the determining step such that each partitioned portion includes, on average, a subset of unique sequences, sequencing the nucleic acid to obtain sequence reads, and assembling a consensus sequence from the reads.

63 Claims, 16 Drawing Sheets

(56) References Cited

U.S. PATENT DOCUMENTS

| | | | |
|---|---|---|---|
| 6,162,400 A | 12/2000 | Schembri | |
| 6,191,267 B1 | 2/2001 | Kong et al. | |
| 6,245,545 B1 | 6/2001 | Kong et al. | |
| 6,313,284 B1 | 11/2001 | Kwiatkowski et al. | |
| 6,361,947 B1 | 3/2002 | Dong et al. | |
| 6,714,874 B1 | 3/2004 | Myers et al. | |
| 6,790,946 B2 | 9/2004 | Kwiatkowski et al. | |
| 6,846,658 B1 | 1/2005 | Vaisvila et al. | |
| 6,872,529 B2 | 3/2005 | Su | |
| 6,951,720 B2 | 10/2005 | Burgin, Jr. et al. | |
| 6,958,225 B2 | 10/2005 | Dong | |
| 7,244,567 B2 | 7/2007 | Chen et al. | |
| 7,247,486 B2 | 7/2007 | Schembri | |
| 7,406,385 B2 | 7/2008 | Sorenson | |
| 7,452,671 B2 | 11/2008 | Shapero et al. | |
| 7,575,865 B2 | 8/2009 | Leamon et al. | |
| 7,582,420 B2 | 9/2009 | Oliphant et al. | |
| 7,611,869 B2 | 11/2009 | Fan | |
| 7,709,197 B2 | 5/2010 | Drmanac | |
| 7,901,891 B2 | 3/2011 | Drmanac | |
| 7,960,104 B2 | 6/2011 | Drmanac et al. | |
| 2002/0051994 A1 | 5/2002 | Kwiatkowski et al. | |
| 2002/0142314 A1 | 10/2002 | Dong et al. | |
| 2003/0008306 A1 | 1/2003 | Turnbull et al. | |
| 2003/0082535 A1 | 5/2003 | Leushner et al. | |
| 2003/0143599 A1 | 7/2003 | Makarov et al. | |
| 2003/0165841 A1 | 9/2003 | Burgin et al. | |
| 2003/0170652 A1 | 9/2003 | Inoko et al. | |
| 2003/0211506 A1 | 11/2003 | Kong et al. | |
| 2004/0002090 A1 | 1/2004 | Mayer et al. | |
| 2004/0067493 A1 | 4/2004 | Matsuzaki et al. | |
| 2004/0086892 A1 | 5/2004 | Crothers et al. | |
| 2004/0110153 A1 | 6/2004 | Dong et al. | |
| 2004/0171047 A1 | 9/2004 | Dahl et al. | |
| 2004/0191812 A1 | 9/2004 | Davydova et al. | |
| 2004/0209299 A1 | 10/2004 | Pinter et al. | |
| 2004/0224324 A1 | 11/2004 | Dear | |
| 2004/0248153 A1 | 12/2004 | Dear et al. | |
| 2005/0112636 A1 | 5/2005 | Hurt et al. | |
| 2005/0147973 A1 | 7/2005 | Knott | |
| 2005/0158769 A1 | 7/2005 | Vaisvila et al. | |
| 2006/0073493 A1 | 4/2006 | Fasulo et al. | |
| 2006/0281082 A1 | 12/2006 | Zhu | |
| 2007/0009894 A1 | 1/2007 | Crothers | |
| 2007/0099208 A1 | 5/2007 | Drmanac et al. | |
| 2007/0196849 A1 | 8/2007 | Spier | |
| 2008/0096255 A1 | 4/2008 | Harbers et al. | |
| 2008/0160511 A1 | 7/2008 | Dawson et al. | |
| 2008/0234136 A1 | 9/2008 | Drmanac et al. | |
| 2008/0274466 A1 | 11/2008 | McKernan | |
| 2009/0005252 A1 | 1/2009 | Drmanac et al. | |
| 2009/0011943 A1 | 1/2009 | Drmanac et al. | |
| 2009/0035823 A1 | 2/2009 | Soldatov et al. | |
| 2009/0099041 A1 | 4/2009 | Church et al. | |
| 2009/0105094 A1 | 4/2009 | Heiner et al. | |
| 2009/0118129 A1 | 5/2009 | Turner | |
| 2009/0118488 A1 | 5/2009 | Drmanac et al. | |
| 2009/0137404 A1 | 5/2009 | Drmanac et al. | |
| 2009/0137414 A1 | 5/2009 | Drmanac et al. | |
| 2009/0155781 A1 | 6/2009 | Drmanac et al. | |
| 2009/0176234 A1 | 7/2009 | Drmanac et al. | |
| 2009/0181861 A1 | 7/2009 | Li et al. | |
| 2009/0233291 A1 | 9/2009 | Chen et al. | |
| 2009/0264299 A1 | 10/2009 | Drmanac et al. | |
| 2009/0270273 A1 | 10/2009 | Burns et al. | |
| 2009/0298064 A1 | 12/2009 | Batzoglou et al. | |
| 2010/0028888 A1 | 2/2010 | Smith et al. | |
| 2010/0069250 A1* | 3/2010 | White et al. | 506/4 |
| 2010/0069263 A1 | 3/2010 | Shendure et al. | |
| 2010/0120098 A1 | 5/2010 | Grunenwald et al. | |
| 2011/0003701 A1 | 1/2011 | Ferreri et al. | |
| 2011/0015096 A1 | 1/2011 | Chiu | |
| 2011/0033854 A1 | 2/2011 | Drmanac et al. | |
| 2011/0071053 A1 | 3/2011 | Drmanac et al. | |
| 2011/0081687 A1 | 4/2011 | McKernan | |
| 2011/0159499 A1 | 6/2011 | Hindson et al. | |
| 2011/0201507 A1 | 8/2011 | Rava et al. | |
| 2011/0223585 A1 | 9/2011 | Gullberg et al. | |
| 2011/0251084 A1 | 10/2011 | Brenan et al. | |
| 2011/0281736 A1 | 11/2011 | Drmanac et al. | |
| 2011/0281738 A1 | 11/2011 | Drmanac et al. | |
| 2011/0319281 A1 | 12/2011 | Drmanac | |
| 2012/0011086 A1 | 1/2012 | Zhang et al. | |
| 2012/0135893 A1 | 5/2012 | Drmanac et al. | |

FOREIGN PATENT DOCUMENTS

| | | |
|---|---|---|
| EP | 0983288 B1 | 3/2000 |
| EP | 1048731 B1 | 11/2000 |
| EP | 1197549 B1 | 4/2002 |
| EP | 1303530 B1 | 4/2003 |
| EP | 1558764 B1 | 8/2005 |
| EP | 1598427 A1 | 11/2005 |
| EP | 1616008 B1 | 1/2006 |
| EP | 1757683 A1 | 2/2007 |
| EP | 969102 B1 | 12/2007 |
| EP | 2058396 A1 | 5/2009 |
| EP | 2202322 A1 | 6/2010 |
| EP | 2620497 A1 | 7/2013 |
| GB | 2496016 | 5/2013 |
| WO | WO-96/23904 A1 | 8/1996 |
| WO | WO-98/07738 A1 | 2/1998 |
| WO | WO-98/51698 A1 | 11/1998 |
| WO | WO-98/51783 A1 | 11/1998 |
| WO | WO-99/13094 A2 | 3/1999 |
| WO | WO-01/94544 A2 | 12/2001 |
| WO | WO-02/090522 A2 | 11/2002 |
| WO | WO-02/103046 A2 | 12/2002 |
| WO | WO-03/036434 A2 | 5/2003 |
| WO | WO-03/083137 A2 | 10/2003 |
| WO | 2004022758 A1 | 3/2004 |
| WO | WO-2004/044549 A2 | 5/2004 |
| WO | WO-2004/058989 A2 | 7/2004 |
| WO | WO-2004/059289 A2 | 7/2004 |
| WO | WO-2004/092375 A2 | 10/2004 |
| WO | WO-2005/021717 A2 | 3/2005 |
| WO | WO-2005/030929 A2 | 4/2005 |
| WO | WO-2006/003721 A1 | 1/2006 |
| WO | 2006119066 A2 | 11/2006 |
| WO | 2006137734 A1 | 12/2006 |
| WO | WO-2006/138257 A2 | 12/2006 |
| WO | WO-2006/138284 A2 | 12/2006 |
| WO | WO-2007/024653 A2 | 3/2007 |
| WO | WO-2007/044245 A2 | 4/2007 |
| WO | 2007/073171 A2 | 6/2007 |
| WO | WO-2007/092538 A2 | 8/2007 |
| WO | WO-2007/101075 A2 | 9/2007 |
| WO | WO-2007/133831 A2 | 11/2007 |
| WO | WO-2008/083327 A2 | 7/2008 |
| WO | WO-2008/084405 A2 | 7/2008 |
| WO | 2009045344 A2 | 4/2009 |
| WO | WO-2009/076238 A2 | 6/2009 |
| WO | WO-2009/089384 A1 | 7/2009 |
| WO | WO-2009/120183 A2 | 10/2009 |
| WO | WO-2009/132028 A1 | 10/2009 |
| WO | 2010148039 A2 | 12/2010 |
| WO | 2011053987 A1 | 5/2011 |
| WO | WO-2011/066476 A1 | 6/2011 |
| WO | WO-2012/005595 A2 | 1/2012 |
| WO | WO-2012/008831 A1 | 1/2012 |
| WO | 2012029577 A1 | 3/2012 |
| WO | 2012080591 A1 | 6/2012 |
| WO | 2012142611 A2 | 10/2012 |
| WO | 2012149042 A2 | 11/2012 |
| WO | 2012162267 A2 | 11/2012 |
| WO | 2013036929 A1 | 3/2013 |

OTHER PUBLICATIONS

Dear, et al. Happy Mapping, Practical Approach Series. vol. 184, 1997, pp. 95-123.

(56) References Cited

OTHER PUBLICATIONS

Howie, et al. A Flexible and Accurate Genotype Imputation Method for the Next Generation of Genome-Wide Association Studies. PLoS Genet. Jun. 2009;5(6):e1000529. Epub Jun. 19, 2009.

Huang, et al. CAP3: A DNA Sequence Assembly Program. Genome Res. Sep. 1999;9(9):868-77.

Kitzman, et al. Haplotype-resolved genome sequencing of a Gujarati Indian individual. Nat Biotechnol. Jan. 2011;29(1):59-63. Epub Dec. 19, 2010.

Peters, et al. Accurate whole-genome sequencing and haplotyping from 10 to 20 human cells. Nature. Jul. 11, 2012 ;487(7406):190-5. doi: 10.1038/nature11236.

International Search Report and Written Opinion for PCT/US12/54461, dated Feb. 4, 2013, 19 pages.

Syed, et al., "Optimized library preparation method for next-generation sequencing," 2009, Nature Methods 6 (Oct. 2009), pp. i-ii.

Jiang, et al., "Old can be new again: HAPPY whole genome sequencing, mapping and assembly," Apr. 15, 2009, Int'l J. Bio. Sci. 5:298-303.

Arneson, et al., "PCR-based whole genome amplification," 2007, Chapter 18 (pp. 293-317) of Hughes, S. and Moody, A., PCR (Method Express), Scion Publishing Ltd, Oxfordshire UK.

Third-Party Submission Under 37 CFR 1.290 Concise Description of Relevance with Pre-Issuance Submission Under 37 C.F.R. 1.290 filed in U.S. Appl. No. 13/608,778 on Sep. 24, 2013 (39 pages).

Third-Party Observations in Relation to GB Application 1216076.8, May 23, 2014, 7 pages.

Lasken, et al., "Mechanism of chimera formation during the Multiple Displacement Amplification reaction," BMC Biotechnology 2007, 7:19, 11 pages.

Chen et al., "Scanning the human genome at kilobase resolution," Genome Research (2008); vol. 18, pp. 751-762, See Abstract, p. 752 col. 1 para 2, Fig 1. Available at http://genome.cshlp.org/content/18/5/751.full.pdf+html.

Combined Search and Examination Report under Section 17 & 18(3) for Application No. GB1216076.8, dated Feb. 25, 2013, 9 pages.

Cummings et al., "Combining target enrichment with barcode multiplexing for high throughput SNP discovery," BMC Genomics 2010, 11:641, published online Nov. 18, 2010.

Examination Report under Section 18(3) for Application No. GB1216076.8, dated Feb. 26, 2014, 5 pages.

Farias-Hesson et al., "Semi-Automated Library Preparation for High-Throughput DNA Sequencing Platforms," J. Biomed. Biotechnol., 2010:617469, published online Jun. 8, 2010.

Further Search Report under Section 17 for Application No. GB1216076.8, dated Feb. 23, 2014, 2 pages.

Grothues et al., 1993, "PCR amplification of megabase DNA with tagged random primers (T-PCR)" Nucleic Acids Research 21:1321-1322.

Third-Party Observations in Relation to GB Application 1216076.8, Sep. 12, 2013, 6 pages.

Salazar-Gonzalez et al., "Deciphering human immunodeficiency virus . . . ", Journal of Virology (2008); vol. 82, pp. 3952-3970, See whole document, esp. p. 3954 col. 2 para 2—p. 3955 col. 1 para 4. Available at http://jvi.asm.org/content/82/8/3952.full.pdf+html.

Supplement Third-Party Observations in Relation to GB Application 1216076.8, Nov. 1, 2013, 14 pages.

Voskoboynik et al., eLife 2013;2:e00569 (for brevity, only pp. 1 and 18 are provided).

Xu et al., "Dual primer emulsion PCR for next generation DNA sequencing," Bio Techniques 2010, 48:409-412.

Kapa Library Quantification Press Release (Jul. 1, 2010), originally available at http://www.anachem.co.uk.news.2010.kapangs, currently available at (and retrieved from) https://web.archive.org.web/20101108005835/http://www.anachem.co.uk/news/2010/kapangs.

Supplementary European Search Report issued for 12830052.2, mailed on May 7, 2015.

Emily H. Turner, et al. "Methods for Genomic Partitioning", Annual Review of Genomics and Human Genetics, vol. 10, No. 1, (Sep. 1, 2009), pp. 263-284.

G. Bentley et al., "High-Resolution, high-throughput HLA genotyping by next-generation sequencing", Tissue Antigens, vol. 74, No. 5., (Nov. 1, 2009), pp. 393-403.

Paul, P. & Apgar, J., Single-molecule dilution and multiple displacement amplification for molecular haplotyping, BioTechniques, Apr. 2005, pp. 553-559, vol. 38.

McCaughan, F. & Dear, P.H., Single-molecule genomics, Journal of Pathology, Jan. 2010, pp. 297-306, vol. 220.

Stephens, J.C. et al., Theoretical Underpinning of the Single-Molecule-Dilution (SMD) Method of Direct Haplotype Resolution, Am. J. Hum. Genet., Jun. 1990, pp. 1149-1155, vol. 46.

Ruano, G. et al., Haplotype of multiple polymorphisms resolved by enzymatic amplification of single DNA molecules, PNAS, Aug. 1990, pp. 6296-6300, vol. 87.

International Search Report for Canadian Patent Application No. 2,848,304 dated Sep. 15, 2016.

Examination Report dated Oct. 1, 2015, for UK Patent Application No. GB1216076.8, filed Oct. 9, 2012 (14 pages).

\* cited by examiner

USING PCR

1. Ligate A-prim-A

2. Circularize

Final product:

USING RESTRICTION ENZYMES

1. Ligate A-rest-A

2. Circularize        3. Cut with restriction enzyme

Final product:

METHODS FOR OBTAINING A SEQUENCE

RELATED APPLICATION

The present application claims the benefit of and priority to U.S. provisional patent application Ser. No. 61/532,882, filed Sep. 9, 2011, the content of which is incorporated by reference herein in its entirety.

GOVERNMENT SUPPORT

This invention was made with Government support under Grant Number AG037968 awarded by the National Institute of Health (NIH). The Government has certain rights in this invention.

FIELD OF THE INVENTION

The invention generally relates to methods for obtaining a sequence, such as a consensus sequence or a haplotype sequence.

BACKGROUND

Methods to sequence or identify significant segments of the human genome and genetic variations within those segments are becoming commonplace. However, a major impediment to understanding the health implications of genomic variation lies in the ability to correlate genomic differences with the human health consequences of those differences. Whole genome sequencing is an important first step toward elucidation of the genomic underpinnings of human health. Once sequenced, genomic DNA must be assembled or aligned to a reference sequence. A generally-accepted protocol for genome assembly involves using fosmids and BAC libraries in which long pieces of DNA are introduced into bacterial cells that are sequenced independently and reassembled. Such a process is expensive, laborious, and time consuming (e.g., a few weeks to months).

Recent advances in sequencing throughput and library preparation has allowed mammalian-sized genomes to be sequenced in a matter of days. Current sequencing technologies allow the generation of enormous amounts of sequence using short sequence reads (i.e., lengths of about 100 bp to about 200 bp). Those technologies provide up to 30 GB of sequences per lane, which is equivalent to 10× coverage of the human genome.

However, application of those technologies to de-novo genome assemblies is limited by short sequence read length, which is insufficient to resolve complex genome structure and to produce consistent genome assembly. Further, short sequence reads cannot be used to obtain phasing data (i.e., which variants are on the same chromosome). Additionally, assembly from short reads requires construction of a de-bruign graph, which is a computationally-intensive process requiring supercomputers with large amount of RAM, which limits application to large sequencing centers with access to supercomputers. Thus, it is difficult and expensive to use short sequence reads to get quality de-novo reference genome assemblies.

SUMMARY

The invention generally relates to methods for obtaining a sequence, such as a consensus sequence or a haplotype sequence. Methods of the invention allow for sequencing of long continuous (kilobase scale) nucleic acid fragments using conventional short read sequencing technologies. Methods of the invention are accomplished by determining an amount of amplifiable nucleic acid present in a sample, partitioning the nucleic acid based upon results of the determining step such that each partitioned portion includes, on average, a subset of unique sequences, sequencing the nucleic acid to obtain sequence reads, and assembling a consensus sequence from the reads. Limiting the number of amplifiable molecules per partitioned portion so that almost 100% of all amplifiable molecules are present as single copies greatly reduces or eliminates chances of having a repeated or homologous sequence within a partitioned portion. Thus, sample complexity is significantly reduced, which reduces ambiguity in the reconstruction of a consensus sequence. In some cases, the reconstruction can achieve complete unambiguity. In this manner, methods of the invention allow conversion of short sequence reads (about 10 bp to about 200 bp) into intermediate sized fragments (about 10,000 bp) that can be assembled into full chromosomes to provide reference quality assemblies. In some embodiments, the fraction of the unique sequences in the sample is greater than 10%, 20%, 50%, or 95%.

Nucleic acid obtained from biological samples typically is fragmented to produce suitable fragments for analysis. Thus, methods of the invention may further involve an initial step of fragmenting obtained nucleic acid. To further provide for unambiguous reconstruction of a consensus sequence, methods of the invention may also involve attaching unique marker identifiers to ends of each fragment, thus ensuring that homologous fragments, for example originating from homologous copies of chromosomes, can be detected based upon the unique markers that are attached to each fragment. In other embodiments, To further provide for unambiguous reconstruction of a consensus sequence, methods of the invention may also involve attaching labels to the nucleic acids in each partitioned portion. Exemplary labels include nucleic acid binding proteins, optical labels, nucleotide analogs, and others known in the art. In preferred embodiments, the labels are bar code sequences. In some embodiments, the labels are adaptor primer sequences. These adaptor sequences described in the invention, in some embodiments, allow resolving assembly ambiguities by linking the related sequence information of sequence segments together. In some embodiments, the adaptor sequences adjacent to the ends of the one or more nucleic acids are different. In some embodiments, the one or more target polynucleotides comprise at least a first target polynucleotide adjacent to a first known nucleotide sequence at at least one end and a second target polynucleotide adjacent to a second known nucleotide sequence at at least one end, wherein the first known nucleotide sequence is not the same as the second known nucleotide sequence. In some embodiments, the first target polynucleotide further comprises a third known nucleotide sequence at at least one end, wherein the second target polynucleotide further comprises a fourth known nucleotide sequence at at least one end, wherein the third known nucleotide sequence is dependent on the first known nucleotide sequence and wherein the fourth known nucleotide sequence is dependent on the second known nucleotide sequence. In some embodiments, relating sequence information from the plurality of fragments into the first target polynucleotide comprises linking the first and the third known nucleotide sequences. In some embodiments, the first and third known nucleotide sequences are different from the second and fourth known nucleotide sequences. The nucleic acid obtained from biological samples may originate from genomic DNA. In some embodiments, the genomic DNA may originate from a polyploidy genome. The nucleic acid obtained from biological samples may comprise a portion of a major histocompatibility complex gene. In some embodiments, the nucleic acid may originate from fetal DNA.

Partitioning of the fragments into partitioned portions may be by any method known in the art. For example, partitioning may involve dispensing the sample into different wells of a microwell plate, or partitioning may involve segmenting the sample into droplets. In particular embodiments, partitioning is performed under microfluidic control.

After partitioning, the fragmented nucleic acids may be amplified by any methods known in the art. In particular embodiments, PCR is used to amplify the fragments. The amplified fragments in each partitioned portion may then be fragmented and bar code sequences are attached to these fragments. Fragmenting may be by any method known in the art, such as restriction digesting or by application of mechanical force, e.g., sonication. In some embodiments, the bar code sequences may be nucleic acid sequences. The length of the bar code sequences may be greater than 3 nucleotide long. In certain embodiments, the fragments are longer than 10 bp or 250 bp, or shorter than 1000 bp or 2000 bp.

After bar codes have been incorporated into the nucleic acid templates, the templates are sequenced. Sequencing may be by any method known in the art. In certain embodiments, sequencing is sequencing by synthesis. In other embodiments, sequencing is single molecule sequencing by synthesis. In some embodiments, sequencing is ion semiconductor sequencing. In some embodiments, sequencing is nanopore sequencing. In some embodiments, sequencing is sequencing by electron microscopy. In certain embodiments, sequencing involves hybridizing a primer to the template to form a template/primer duplex, contacting the duplex with a polymerase enzyme in the presence of a detectably labeled nucleotides under conditions that permit the polymerase to add nucleotides to the primer in a template-dependent manner, detecting a signal from the incorporated labeled nucleotide, and sequentially repeating the contacting and detecting steps at least once, wherein sequential detection of incorporated labeled nucleotide determines the sequence of the nucleic acid. In some embodiments, the sequencing comprises obtaining paired end reads. The accuracy or average accuracy of the sequence information may be greater than 80%, 90%, 95%, 99% or 99.98%. In some embodiments, the sequence information obtained is more than 50 bp, 100 bp or 200 bp. The sequence information may be obtained in less than 1 month, 2 weeks, 1 week 1 day, 3 hours, 1 hour, 30 minutes, 10 minutes, or 5 minutes. The sequence accuracy or average accuracy may be greater than 95% or 99%. The sequence coverage may be greater than 20 fold or less than 500 fold. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorescien, coumarin, BODIPY, alexa, or conjugated multi-dyes. In some embodiments, the nucleotide is flagged if one or more of its sequence segments are substantially similar to one or more sequence segments of another nucleotide within the same partition.

Another aspect of the invention provides methods for assembling a consensus sequence that involve obtaining nucleic acid, fragmenting the nucleic acid, determining an amount of amplifiable nucleic acid present in a sample, partitioning the fragmented nucleic acids based upon results of the determining step, amplifying the partitioned nucleic acids, attaching bar codes to the amplified nucleic acid, sequencing the nucleic acid to obtain bar coded sequence reads, and assembling a consensus sequence from the reads. In certain embodiments, each partitioned portion includes, on average, a unique subset of nucleic acids.

In one aspect, the invention relates to a method for relating sequence components in a target polynucleotide, the method comprising: (a) providing at least one sample comprising one or more target polynucleotides each adjacent to a known nucleotide sequence at at least one end, wherein each target polynucleotide comprises one or more sequence segments with a sequence segment length, and wherein the known nucleotide sequence is capable of serving as an amplification target; (b) partitioning the sample into a finite plurality of partitions such that at least a fraction of the sequence segments in at least one partition is estimated to be present as a single copy in the at least one partition with a likelihood that is less than 99.999%; (c) subjecting the partition to polynucleotide fragmentation thereby generating a set of fragments; (d) obtaining partial or complete sequence information from at least a subset of the fragments; and (e) relating sequence information from a plurality of fragments into a subset of the one or more target polynucleotides. In a similar aspect, the invention relates to a method for relating sequence components in a target polynucleotide, the method comprising: (a) providing at least one sample comprising one or more target polynucleotides each adjacent to a known nucleotide sequence at at least one end, wherein each target polynucleotide comprises one or more sequence segments with a sequence segment length of greater than 30 bp, and wherein the known nucleotide sequence is capable of serving as an amplification target; (b) partitioning the sample into a finite plurality of partitions such that at least a fraction of the sequence segments in at least one partition is estimated to be present as a single copy in the at least one partition with a likelihood that is less than 100%; (c) subjecting the partition to polynucleotide fragmentation thereby generating a set of fragments; (d) obtaining partial or complete sequence information from at least a subset of the fragments; and (e) relating sequence information from a plurality of fragments into a subset of the one or more target polynucleotides. In some embodiments, the methods comprise subjecting at least one partition to nucleic acid amplification using the known nucleotide sequence as an amplification target thereby amplifying the one or more target polynucleotides into amplicons such that at least a fraction of the sequence segments originating from the at least one or more target polynucleotides or the amplicons in the at least one partition is estimated to be present as a single copy prior to amplification in the at least one partition with a likelihood that is less than 99.999%. In some embodiments, the at least one sample comprises a first target polynucleotide and a second target polynucleotide each adjacent to a first known nucleotide sequence and a second known nucleotide sequence at at least one end, wherein the first known nucleotide sequence is not the same as the second known nucleotide sequence. In some embodiments the sequence segment length is greater than about 30 bp. In some embodiments, the sequence segment length is greater than about 50 bp. In some embodiments, the sequence segment length is less than about 100 bp. In some embodiments, the fraction is greater than 10%. In some embodiments, the fraction is greater than 20%. In some embodiments, the fraction is greater than 50%. In some embodiments, the fraction is 95%. In some embodiments, the likelihood is greater than 80%. In some embodiments, likelihood is 99%. In some embodiments, upon partitioning at least one sequence segment is present in multiple copies in the at least one partition. In some embodiments, the method further comprises amplifying the target polynucleotide prior to subjecting the partition to polynucleotide fragmentation. In some embodiments, the target polynucleotide is adjacent to a known nucleotide sequence at both ends. In some embodiments, the known sequence is introduced onto the target polynucleotide by ligating an adaptor oligonucleotide. In some embodiments, on average, the fragments are longer than 10 bp. In some embodiments, on average, the fragments are shorter than 2000 bp. In some embodiments, on average, the fragments are shorter than 1000 bp. In some embodiments, on average, the fragments are longer than 250 bp. In some embodiments, on average, the one or more target polynucleotides are longer than 5000 bp. In some embodiments, on average, the one or more target polynucleotides are longer than 10000 bp. In some embodiments, the fragments within a partition are labeled with one or more partition specific barcodes. In some embodiments, the barcodes are nucleic acid sequences. In some embodiments, the barcodes are greater than 3 nucleotides long. In some embodiments, the barcodes are greater than 5 nucleotides long. In some embodiments, the one or more partition specific barcodes comprise 2 barcodes that are each greater than 2 nucleotides long. In some embodiments, all two partition specific barcodes comprise at least two differences in the nucleic acid sequence. In some embodiments, the sequence information comprises sequence reads obtained by sequencing. In some embodiments, the sequence information comprises an accuracy of greater than 99%. In some embodiments, the sequence information comprises an accuracy of greater than 95%. In some embodiments, the sequence information comprises an accuracy of greater than 90%. In some embodiments, the sequence information comprises an accuracy of greater than 80%. In some embodiments, the sequence information comprises an average accuracy of greater than 99%. In some embodiments, the sequence information comprises an average accuracy of greater than 95%. In some embodiments, the sequence information comprises an average accuracy of greater than 90%. In some embodiments, the sequence information comprises an average accuracy of greater than 80%. In some embodiments, the sequence reads comprise an accuracy of greater than 99.98%. In some embodiments, the sequence information spans more than 50 bp. In some embodiments, the sequence information spans more than 100 bp. In some embodiments, the sequence information spans more than 200 bp. In some embodiments, all sequence information is obtained in less than 1 month. In some embodiments, all sequence information is obtained in less than 2 weeks. In some embodiments, all sequence information is obtained in less than 1 week. In some embodiments, all sequence information is obtained in less than 1 day. In some embodiments, all sequence information is obtained in less than 3 hours. In some embodiments, all sequence information is obtained in less than 1 hour. In some embodiments, all sequence information is obtained in less than 30 minutes. In some embodiments, all sequence information is obtained in less than 10 minutes. In some embodiments, all sequence information is obtained in less than 5 minutes. In some embodiments, the relating step comprises an average accuracy of at least 95%. In some embodiments, the relating step comprises an average accuracy of at least 99%. In some embodiments, the target polynucleotide within the sample is flagged if one or more of its sequence segments are substantially similar to one or more sequence segments of a second target polynucleotide partitioned into the same partition. In some embodiments, the methods further comprise a sequence coverage of greater than 20 fold. In some embodiments, the methods further comprise an average sequence coverage of less than 500 fold. In some embodiments, the sequencing comprises sequencing by synthesis. In some embodiments, the sequencing comprises ion semiconductor sequencing. In some embodiments, the sequencing comprises single molecule real time sequencing. In some embodiments, the sequencing comprises nanopore sequencing. In some embodiments, the sequencing comprises sequencing by electron microspcopy. In some embodiments, the target polynucleotide originates from genomic DNA. In some embodiments, the genomic DNA originates from a polyploid genome. In some embodiments, the target polypeptide comprises a portion of a major histocompatibility complex gene. In some embodiments, the target polypeptide originates from fetal DNA. In some embodiments, the sequencing comprises obtaining paired end reads.

In some embodiments, the methods further comprise utilizing computing resources that are delivered over a network to improve detection of sequence variants and detection average accuracy. In some embodiments, the one or more target polynucleotides originate from a single molecule, and wherein the related sequence information links two or more positions on the single molecule. In some embodiments, the two or more positions on the single molecule are separated by more than 5000 bp. In some embodiments, the two or more positions on the single molecule are separated by more than 10000 bp. In some embodiments, the one or more target polynucleotides comprise a first target polynucleotide and a second polynucleotide and the related sequence information to the first target polynucleotide and the related sequence information to the second target polynucleotide are linked.

In some embodiments, the methods further comprise detecting a genomic structural variation.

In some embodiments, the one or more target polynucleotides originate from one or more tissue samples, wherein relating sequence information comprises detecting a plurality of sequence variants in the one or more tissue samples, and wherein the plurality of sequence variants from one or more tissue sample are compared.

In some embodiments, the methods further comprise providing a diagnosis based on the related sequence information. In some embodiments, the diagnosis is directed to a disease selected from the group consisting of allergic rhinitis, allergic conjunctivitis, allergic asthma, atopic eczema, atopic dermatitis, food allergy, severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects, rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens, hemangiomatosis in newborns, secondary progressive multiple sclerosis, chronic progressive myelodegenerative disease, neurofibromatosis, ganglioneuromatosis, keloid formation, Paget's Disease of the bone, fibrocystic disease (e.g., of the breast or uterus), sarcoidosis, Peronies and Duputren's fibrosis, cirrhosis, atherosclerosis and vascular restenosis, hematologic malignancies and solid tumors, 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

In some embodiments, the one or more target polynucleotides comprise at least a first target polynucleotide adjacent to a first known nucleotide sequence at at least one end and a second target polynucleotide adjacent to a second known nucleotide sequence at at least one end, wherein the first known nucleotide sequence is not the same as the second known nucleotide sequence. In some embodiments, the first target polynucleotide further comprises a third known nucleotide sequence at at least one end, wherein the second target polynucleotide further comprises a fourth known nucleotide sequence at at least one end, wherein the third known nucleotide sequence is dependent on the first known nucleotide sequence and wherein the fourth known nucleotide sequence is dependent on the second known nucleotide sequence. In some embodiments, relating sequence information from the plurality of fragments into the first target polynucleotide comprises linking the first and the third known nucleotide sequences. In some embodiments, the first and third known nucleotide sequences are different from the second and fourth known nucleotide sequences.

In some embodiments, the methods further comprise identifying the presence of a pathogen in the at least one sample. In some embodiments, the pathogen is selected from the group consisting of a bacterial agent, a virus, a parasite, and a fungus. In some embodiments, the bacterial agent is selected from the group consisting of *Escherichia coli*, *Salmonella*, *Shigella*, *Klebsiella*, *Pseudomonas*, *Listeria monocytogenes*, *Mycobacterium tuberculosis*, *Mycobacterium aviumintracellulare*, *Yersinia*, *Francisella*, *Pasteurella*, *Brucella*, *Clostridia*, *Bordetella pertussis*, *Bacteroides*, *Staphylococcus aureus*, *Streptococcus pneumonia*, B-Hemolytic strep., *Corynebacteria*, *Legionella*, *Mycoplasma*, *Ureaplasma*, *Chlamydia*, *Neisseria gonorrhea*, *Neisseria meningitides*, *Hemophilus influenza*, *Enterococcus faecalis*, *Proteus vulgaris*, *Proteus mirabilis*, *Helicobacter pylori*, *Treponema palladium*, *Borrelia burgdorferi*, *Borrelia recurrentis*, *Rickettsial pathogens*, *Nocardia*, and *Acitnomycetes*. In some embodiments, the fungus is selected from the group consisting of *Cryptococcus neoformans*, *Blastomyces dermatitidis*, *Histoplasma capsulatum*, *Coccidioides immitis*, *Paracoccidioides brasiliensis*, *Candida albicans*, *Aspergillus fumigautus*, *Phycomycetes* (*Rhizopus*), *Sporothrix schenckii*, *Chromomycosis*, and *Maduromycosis*. In some embodiments, the virus is selected from the group consisting of human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses. In some embodiments, the parasite is selected from the group consisting of *Plasmodium falciparum*, *Plasmodium malaria*, *Plasmodium vivax*, *Plasmodium ovale*, *Onchoverva volvulus*, *Leishmania*, *Trypanosoma* spp., *Schistosoma* spp., *Entamoeba histolytica*, *Cryptosporidum*, *Giardia* spp., *Trichimonas* spp., *Balatidium coli*, *Wuchereria bancrofti*, *Toxoplasma* spp., *Enterobius vermicularis*, *Ascaris lumbricoides*, *Trichuris trichiura*, *Dracunculus medinesis*, trematodes, *Diphyllobothrium latum*, *Taenia* spp., *Pneumocystis carinii*, and *Necator americanis*. In some embodiments, the pathogen comprises a drug resistant pathogen. In some embodiments, the drug resistant pathogen is selected from the group consisting of vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus.

In a similar aspect with related embodiments, the invention relates to a method of relating sequence components in a target polynucleotide comprising: (a) providing at least one sample comprising one or more target polynucleotides wherein each target polynucleotide comprises one or more sequence segments with a sequence length; (b) partitioning the sample into a finite plurality of partitions such that at least a fraction of the sequence segments in at least one partition is estimated to be present as a single copy in the at least one partition with a likelihood that is less than 99.999%; (c) subjecting the partition to polynucleotide fragmentation thereby generating a set of fragments; (d) obtaining partial or complete sequence information from the fragments; and (e) relating sequence information from a plurality of fragments into the target polynucleotides. In some embodiments, a fraction of said one or more target polynucleotides in the sample are each attached to one or more labels. In some embodiments, said label is nucleic acid binding proteins, optical labels, nucleotide analogs, or oligonucleotides.

In another similar aspect with related embodiments, the invention relates to a method for relating sequence components in a target polynucleotide, the method comprising: (a) providing at least one sample comprising one or more target polynucleotides each adjacent to a known nucleotide sequence at at least one end, wherein each target polynucleotide comprises one or more sequence segments with a sequence segment length; (b) partitioning the sample into a finite plurality of partitions and subjecting at least one partition to nucleic acid amplification thereby amplifying the one or more target polynucleotides into amplicons such that at least a fraction of the sequence segments originating from the at least one or more target polynucleotides or the amplicons in the at least one partition is estimated to be present as a single copy prior to amplification in the at least one partition with a likelihood that is less than 99.999%; (c) subjecting the partition to polynucleotide fragmentation thereby generating a set of fragments; (d) obtaining partial or complete sequence information from at least a subset of the fragments; and (e) relating sequence information from a plurality of fragments into a subset of the one or more polynucleotides. In yet another similar aspect with related embodiments, the invention relates to a method for relating sequence components in a target polynucleotide, the method comprising: (a) providing at least one sample comprising one or more target polynucleotides each adjacent to a known nucleotide sequence at at least one end, wherein each target polynucleotide comprises one or more sequence segments with a sequence segment length of greater than 30 bp; (b) partitioning the sample into a finite plurality of partitions and subjecting at least one partition to nucleic acid amplification thereby amplifying the one or more target polynucleotides into amplicons such that at least a fraction of the sequence segments originating from the at least one or more target polynucleotides or the amplicons in the at least one partition is estimated to be present as a single copy prior to amplification in the at least one partition with a likelihood that is less than 100%; (c) subjecting the partition to polynucleotide fragmentation thereby generating a set of fragments; (d) obtaining partial or complete sequence information from at least a subset of the fragments; and (e) relating sequence information from a plurality of fragments into a subset of the one or more target polynucleotides.

In any aspect of the invention, the method may comprise partitioning the sample into a finite plurality of partitions such that at least a fraction of the sequence segments within a target polynucleotide or within an amplifiable or amplified, for example exponentially amplifiable or amplified, target polynucleotide, in at least one partition is estimated to be present as a single copy in the at least one partition with a likelihood that is lower than 100%, 99.999%, 99.99%, 99.98%, 99.95%, 99.9%, 99.5%, 99.0%, 95%, 90% or less. In any aspect of the invention, the method may comprise partitioning the sample into a finite plurality of partitions such that at least a fraction of the sequence segments within a target polynucleotide or within an amplifiable or amplified, for example exponentially amplifiable or amplified, target polynucleotide, in at least one partition is estimated to be present as a single copy in the at least one partition with a likelihood that is higher than 80%, 90%, 95%, 99%, 99.5%, 99.95%, 99.98%, 99.99%, 99.999%, or more. In any aspect, sequence segment length can be greater than about 10, 20, 30, 40, 50, 60, 70, 80, 90, 100 bp or more. In any aspect, the fraction of the sequence segments estimated to be present as a single copy in a partition can be greater than 5, 10, 20, 30, 40, 50, 60, 70, 80, 90, 95, 99% or greater. In any aspect, the fraction of the sequence segments within amplifiable or amplified, for example exponentially amplifiable or amplified, target polynucleotides, estimated to be present as a single copy in a partition can be greater than 5, 10, 20, 30, 40, 50, 60, 70, 80, 90, 95, 99% or greater. In any aspect, the fragments and/or the target polynucleotides can be longer than 10, 20, 30, 40, 50, 100, 200, 300, 400, 500, 1000, 2000 bp or more. In any aspect, the fragments and/or the target polynucleotides can be shorter than 30, 40, 50, 100, 200, 300, 400, 500, 1000, 2000, 3000, 4000, 5000, 10000, 20000, 30000, 40000, 50000 bp or more. In any aspect, the barcodes can be 2, 3, 4, 5, 6, 7, 8, 9, 10, 11, 12, 13, 14, 15, 16, 17, 18, 19, 20 nucleotides long or longer. In any aspect, the partition specific barcodes may comprise 1, 2, 3, 4, 5, 6, 7, 8, 9, 10 or more barcodes. In any aspect, the sequence information may comprise an accuracy or average accuracy of 80, 90, 95, 98, 99, 99.5, 99.8, 99.9, 99.99, 99.995% or higher. In any aspect, the sequence information may span or on average span more than 30, 40, 50, 60, 70, 80, 90, 100, 120, 150, 180, 200, 250, 300, 400, 500 bp or more. In any aspect the sequence information may be obtained in less than 1 month, 2 weeks, 1 week, 1 day, 3, hours, 1 hour, 30 minutes, 10 minutes, 5 minutes, 1 minute, or less. In any aspect, the relating step may comprise an accuracy or average accuracy of 80, 90, 95, 98, 99, 99.5, 99.8, 99.9, 99.99, 99.995% or higher. In any aspect, the method may comprise a sequence coverage of greater than 2, 3, 4, 5, 6, 7, 8, 9, 10, 12, 15, 20, 25, 30, 40, 50, 60, 70, 80, 90, 100, 200, 300, 400 fold or more. In any aspect, the method may comprise a sequence coverage of less than 500, 400, 300, 200, 100, 90, 80, 70, 60, 50, 40, 30, 25, 20, 15, 12, 10, 9, 8, 7, 6, 5, 4, 3, 2 fold or less.

In another related aspect, the invention relates to a kit for relating sequence components in the one or more target polynucleotides, comprising (a) one or more restriction endonucleases; (b) an enzyme capable of repairing at least one end of polynucleotides; (c) one or more ligases capable of ligating an oligonucleotide sequence to the one or more target polynucleotides; (d) one or more known nucleotide sequences capable of serving as an amplification target; (e) a system capable of selecting a subset of the one or more target polynucleotides of a desired length; and (f) one or more polymerases capable of polynucleotide synthesis. In another aspect, the invention relates to a for relating sequence components in a target polynucleotide, comprising (a) a device comprising a substrate with one or more reaction volumes comprising one or more restriction endonucleases capable of polynucleotide fragmentation; (b) a device comprising a substrate with one or more reaction volumes comprising one or more oligonucleotides with a known sequence; and (c) a device comprising a substrate with one or more reaction volumes comprising one or more polymerases capable of polynucleotide synthesis.

Another aspect of the invention relates to a method of forming a linear nucleic acid molecule comprising a target polynucleotide with an adaptor oligonucleotide at each end, comprising (a) providing a target polynucleotide and an intermediate polynucleotide, wherein the intermediate polynucleotide comprises at least two adaptor oligonucleotides, (b) forming a circular polynucleotide construct by combining the target polynucleotide with the intermediate polynucleotide at each end, and (c) cleaving the circular polynucleotide construct within the intermediate polynucleotide to form a linearized molecule. In some embodiments, the target polynucleotide is subjected to a size selection technique for a particular sized polynucleotide at about 50, 100, 250, 500, 1000, 2500, 5000, or 10,000 nucleotides. In some embodiments, the target polynucleotide is created by fragmentation of a large double stranded polynucleotide by mechanical shearing, chemical or enzymatic treatment. The target polynucleotide, in certain embodiments, is created by a polymerase and nucleotide triphosphates. In some embodiments, the target polynucleotide is subjected to melting temperature thereby producing a single stranded target polynucleotide. The target polynucleotide, in some embodiments, comprises a sticky end that pairs sufficiently complementary with the intermediate polynucleotide. In some embodiments, the target polynucleotide comprises a blunt end. In some embodiments, the blunt end is generated by fragmentation and enzymatic end repair. In some embodiments, the enzymatic end repair comprises a polymerase and one or more nucleotide triphosphates. In some embodiments, the target polynucleotide comprises a poly-N-tail. In some embodiments, the poly-N-tail comprises one or more adenine, thymine, guanine or cytosine nucleotide bases at either its 3' or 5' end that pair sufficiently complementary with the intermediate polynucleotide. In some embodiments, the poly-N-tail is at a 3' end of the target polynucleotide. In some embodiments, the intermediate polynucleotide is sufficiently complementary to the poly-N-tail. In some embodiments, in step (a) the target polynucleotide and the intermediate polynucleotide are present in a ratio of about 1:1, 1:2, 1:3, 1:4, 1:6, 1:8, 1:10 or 1:20. In some embodiments, in step (b) the target polynucleotide and the intermediate polynucleotide are ligated in a ratio of 1:1. In some embodiments, the adaptor oligonucleotide is single or double stranded. In some embodiments, the circular polynucleotide construct is single or double stranded. In some embodiments, the adaptor oligonucleotides at each end of the target polynucleotide are substantially the same. In some embodiments, the adaptor oligonucleotides at each end of the target polynucleotide are different. In some embodiments, at least 3 bases of the adaptor oligonucleotides at each end of the target polynucleotide are different. In some embodiments, at least 4 bases of the adaptor oligonucleotides at each end of the target polynucleotide are different. In some embodiments, there are more than one adaptor oligonucleotides at each end. In some embodiments, the adaptor oligonucleotide comprises one or more identification elements. In some embodiments, at least one of the one or more identification elements comprises a unique identifying tag. In some embodiments, at least one of the one or more identification elements comprises a multiple cloning site. In some embodiments, at least one of the one or more identification elements comprises a universal priming site. In some embodiments, at least one of the one or more identification elements comprises a recognition site for a polymerase. In some embodiments, at least one of the one or more identification elements comprises a nick in the adaptor oligonucleotide. In some embodiments, at least one of the one or more identification elements comprises a molecular binding site. In some embodiments, at least one of the one or more identification elements comprises a recognition site for a topoisomerase enzyme and wherein the topoisomerase is capable of attaching to the recognition site a 3' end of the recognition site. In some embodiments, the attaching comprises forming a covalent bond. In some embodiments, the adaptor oligonucleotide further comprises a combination of the one or more identification elements described earlier in any order. In some embodiments, the intermediate polynucleotide is cleaved using a restriction endonuclease. In some embodiments, ligation of blunt or sticky ends comprises a ligase. In some embodiments, cleaving the circular polynucleotide construct comprises adenine-thymine or guanine-cytosine complementary base pairing. In some embodiments, forming a circular polynucleotide comprises using a topoisomerase enzyme. In some embodiments, the methods in the invention further comprises an additional recovery step employing affinity capture to a molecular binding site in an adaptor oligonucleotide. In some embodiments, the affinity capture is employed after the step wherein the circular polynucleotide construct within the intermediate polynucleotide is cleaved. In some embodiments, the one or more identification elements allow for identification or isolation of the target polynucleotide.

In another aspect, the invention relates to a composition capable of creating a linear nucleic acid molecule comprising a target polynucleotide with an adaptor oligonucleotide at each end for the identification and isolation of a target polynucleotide, comprising (a) the target polynucleotide, (b) an intermediate polynucleotide comprising at least two adaptor oligonucleotides, wherein the intermediate polynucleotide further comprises at least one or more elements that allow for circularization, linearization, identification, amplification or isolation. In some embodiments, the elements of the composition are selected from the group consisting of a unique identifying tag, a multiple cloning site, a universal priming site, a recognition site for a polymerase, a molecular binding site, and a topoisomerase enzyme covalently attached at 3' end to its recognition site. In some embodiments, the composition comprises the intermediate polynucleotide and the target polynucleotide in a ratio of about 1:1, 2:1, 3:1, 4:1, 5:1, 6:1, 8:1, 10:1, or 20:1. In some embodiments, the target polynucleotide is rendered into a circular molecule. In some embodiments, the circular molecule in the composition further comprises the intermediate polynucleotide. In related aspects, the invention relates to a kit comprising the composition capable of creating the linear nucleic acid molecule comprising the target polynucleotide with an adaptor oligonucleotide at each end, further comprising one or more components selected from the group consisting of one or more polymerases, one or more ligases, one or more restriction endonucleases, one or more primers complementary to a universal priming site, one or more molecular binding molecules that recognize a molecular binding site, one or more topoisomerases, one or more single nucleotide triphosphates and one or more terminal transferases. In some embodiments, the kit further comprises one or more class II transposons. In some embodiments, the kit further comprises a sequencing adaptor, a sequencing primer, or a barcode adaptor.

In another aspect, the invention relates to a method for obtaining a sequence, comprising determining an amount of amplifiable nucleic acid present in a sample, partitioning the nucleic acid based upon results of the determining step such that each partitioned portion comprises, on average, a subset of unique sequences, sequencing the nucleic acid to obtain sequence reads, and obtaining a sequence from the reads. In some embodiments, prior to the determining step, the method further comprises fragmenting the nucleic acid. In some embodiments, The method further comprises attaching a set of unique marker identifier to ends of each fragment. In some embodiments, the unique marker identifiers comprise bar code sequences that are part of adapter sequences. In some embodiments, the bar code sequences are the same. In some embodiments, the bar code sequences are different. In some embodiments, the method further comprises attaching labels to the nucleic acids in each partitioned portion. In some embodiments, the labels are bar code sequences. In some embodiments, prior to the attaching labels step, the method further comprises amplifying the nucleic acids in each partitioned portion. In some embodiments, after the amplifying step, the method further comprises fragmenting the amplified nucleic acids in each partitioned portion. In some embodiments, fragmenting comprises restriction digesting. In some embodiments, fragmenting comprises mechanically fragmenting. In some embodiments, fragmenting comprises using an in vitro translocation enzyme. In some embodiments, partitioning comprises dispensing the sample into different wells of a microwell plate. In some embodiments, partitioning comprises segmenting the sample into droplets. In some embodiments, partitioning is performed under microfluidic control. In some embodiments, sequencing is sequencing-by-synthesis. In some embodiments, sequencing is single molecule sequencing-by-synthesis. In some embodiments, the sequence is a consensus sequence. In some embodiments, the sequence is a haplotype sequence.

In another aspect of the invention, a method for obtaining a sequence is described, comprising obtaining nucleic acid, fragmenting the nucleic acid, determining an amount of amplifiable nucleic acid present in a sample, partitioning the fragmented nucleic acids based upon results of the determining step, amplifying the partitioned nucleic acids, attaching bar codes to the amplified nucleic acid, sequencing the nucleic acid to obtain bar coded sequence reads, and obtaining a sequence from the reads. In some embodiments, each partitioned portion comprises, on average, a unique subset of nucleic acids. In some embodiments, the method further comprises attaching marker identifiers to ends of the fragments. In some embodiments, fragmenting comprises restriction digesting. In some embodiments, fragmenting comprises mechanically fragmenting. In some embodiments, fragmenting comprises using an in vitro translocation enzyme. In some embodiments, partitioning comprises dispensing the sample into different wells of a microwell plate. In some embodiments, partitioning comprises segmenting the sample into droplets. In some embodiments, partitioning is performed under microfluidic control. In some embodiments, sequencing is sequencing-by-synthesis. In some embodiments, sequencing is single molecule sequencing-by-synthesis. In some embodiments, the sequence is a consensus sequence. In some embodiments, the sequence is a haplotype sequence.

In yet another aspect, a system for reagent dispensing is disclosed that comprises a first vessel having a flow through hole on a bottom portion of the vessel, and a second vessel, wherein the system is configured such that the first vessel is situated above the second vessel such that the second vessel is capable of receiving a reagent from the first vessel. In some embodiments, the first and second vessels are multi-well plates. In some embodiments, the multiwell plates are 96 or 384 well plates. In some embodiments, the first vessel further comprises a cover. In some embodiments, the system further comprises a centrifuge. In some embodiments, the system further comprises a permeable membrane, wherein the membrane is situated between the first and second vessels. In some embodiments, force generated by the centrifuge causes a reagent in the first vessel to pass through the membrane and into the second vessel.

In another aspect of the invention, a method for dispensing reagents is described that comprises providing a system comprising a first vessel having a flow through hole on a bottom portion of the vessel, a second vessel, wherein the system is configured such that the first vessel is situated above the second vessel such that the second vessel is capable of receiving a reagent from the first vessel, dispensing a reagent into the first vessel, and applying centrifugal force to the system to cause the reagent to pass into the second vessel. In some embodiments, prior to the providing step, the method further comprises dispensing a sample into the second vessel. In some embodiments, the first and second vessels are multiwell plates. In some embodiments, the multiwell plates are 96 or 384 well plates. In some embodiments, the first vessel further comprises a cover. In some embodiments, the centrifugal force is generated by a centrifuge. In some embodiments, the system further comprises a permeable membrane, wherein the membrane is situated between the first and second vessels.

BRIEF DESCRIPTION OF THE DRAWINGS

FIG. 5A shows a method that uses PCR and FIG. 5B shows a method that uses a restriction enzyme.

DETAILED DESCRIPTION

Methods of the invention provide a highly-scalable library construction method that allows accurate reconstruction of intermediate sized genomic fragments from short paired reads. According to embodiments of the invention, genomic DNA is converted into a library of intermediately sized fragments 8-10 kb that are amplified inside partitioned portions after artificially limiting number of template molecules per portion. Resulting amplicon libraries are fragmented and converted to sequencing libraries labeled with unique bar codes to allow reads to be split according to partitioned portion after sequencing. Long fragments are then reassembled using a sequencing algorithm from the short paired reads.

Figure 1:
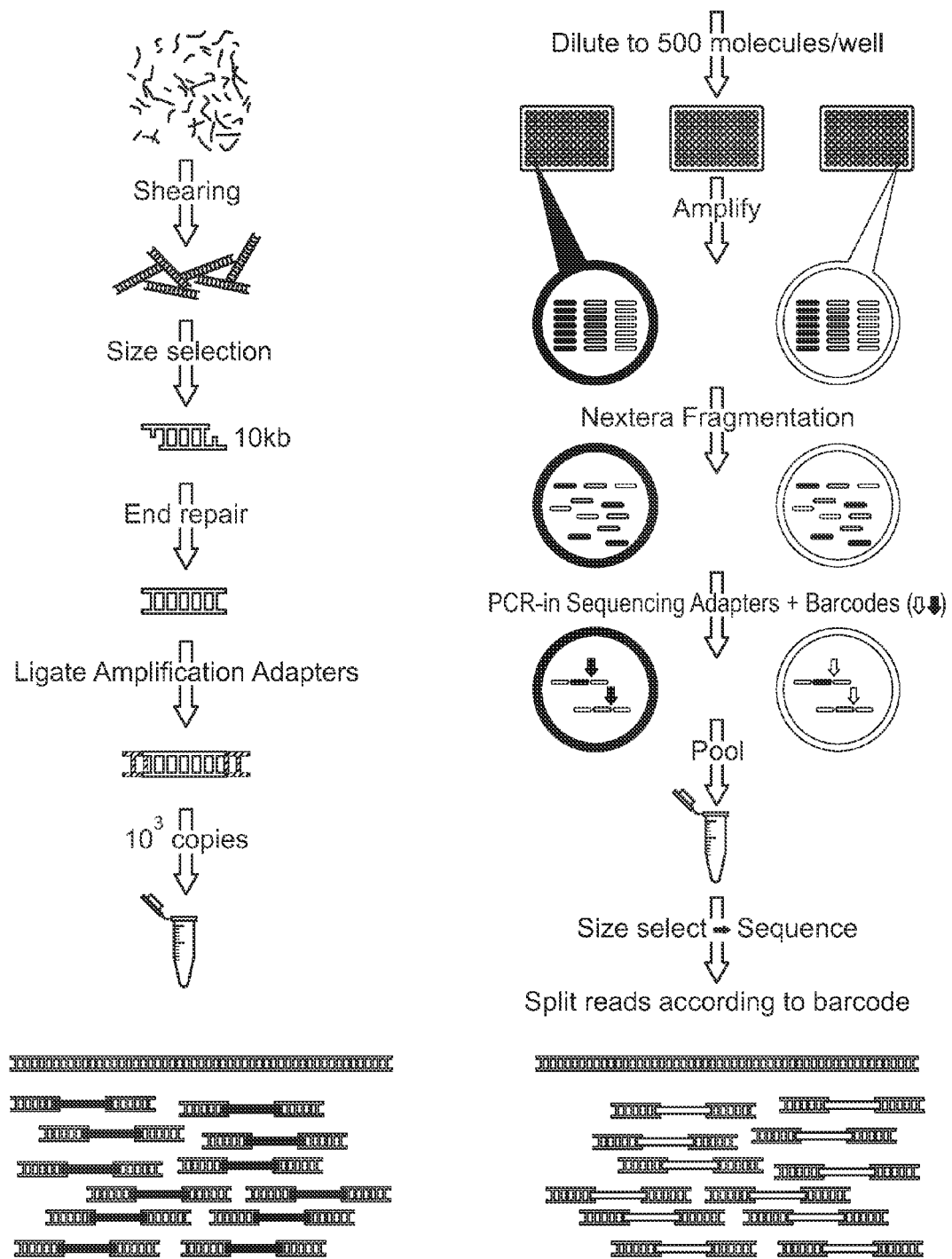
FIG. 1 is a diagram showing an exemplary embodiments of methods of the invention.

FIG. 1 provides an exemplary embodiment of methods of the invention. In one embodiment, nucleic acid template molecules (e.g., DNA or RNA) are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present invention include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982).

In specific aspects, the present invention introduces a concept of multiplexing two or more enzymatic processes in one reaction, and teaches how to optimize a highly multiplexed enzymatic process. In particular embodiments, the present invention is directed to compositions and methods for simultaneous processing of DNA molecules with a combination of enzymes in a one-step-one-tube reaction and producing either a collection of molecules suitable for further processing, for example for amplification, or in some cases, the methods and compositions of the invention result in amplified DNA molecules. In particular embodiments, the methods of the invention can be easily applied to any type of fragmented double stranded DNA including but not limited to, for example, free DNA isolated from plasma, serum, and/or urine; apoptotic DNA from cells and/or tissues; DNA fragmented enzymatically in vitro (for example, by DNase I and/or restriction endonuclease); and/or DNA fragmented by mechanical forces (hydro-shear, sonication, nebulization, etc.). Additional suitable methods and compositions of producing nucleic acid molecules comprising stem-loop oligonucleotides are further described in detail in U.S. Pat. No. 7,803,550, which is herein incorporated by reference in its entirety.

In other embodiments, the invention can be easily applied to any high molecular weight double stranded DNA including, for example, DNA isolated from tissues, cell culture, bodily fluids, animal tissue, plant, bacteria, fungi, viruses, etc.

Nucleic acid obtained from biological samples typically is fragmented to produce suitable fragments for analysis. Template nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid template molecules can be from about 2 kb bases to about 40 kb. In a particular embodiment, nucleic acids are about 6 kb-10 kb fragments. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In one embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$—($OCH_2$—$CH_2$)$_x$OH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), .beta.-mercaptoethanol, DTE, GSH, cysteine, cysteamine, tricarboxyethyl phosphine (TCEP), or salts of sulfurous acid.

Size selection of the nucleic acids may be performed to remove very short fragments or very long fragments. The nucleic acid fragments can be partitioned into fractions comprising a desired number of fragments using any suitable method known in the art. In some embodiments, the fractions include about 1, 2, 5, 10, 50, 100, 250, 500, 750, 1000, 1500, 2000, 5000 or 10,000 molecules. Suitable methods to limit the fragment size in each fragment are known in the art. In various embodiments of the invention, the fragment size is limited to 1, 2, 3, 4, 5, 7, 10, 12, 15, 20, 25, 30, 50, 100 kb or longer.

In various embodiments, the fragments are amplified after partitioning. Any amplification method known in the art may be used. Examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In particular embodiments, PCR is used to amplify DNA molecules after they are dispensed into individual partitions. In some cases, one or more specific priming sequences within amplification adapters are utilized for PCR amplification. The amplification adapters may be ligated to fragmented DNA molecules before or after dispensing into individual partitions. Polynucleotides comprising amplification adapters with suitable priming sequences on both ends can be PCR amplified exponentially. Typically, polynucleotides with only one suitable priming sequence, for example due to imperfect ligation efficiency of amplification adapters comprising priming sequences would only undergo linear amplification. Further, polynucleotides can be eliminated from amplification, for example PCR amplification, all together, if no adapters comprising suitable priming sequences are ligated. In some embodiments, the number of PCR cycles vary between 10-30, but can be as low as 9, 8, 7, 6, 5, 4, 3, 2 or less or as high as 40, 45, 50, 55, 60 or more. As a result, exponentially amplifiable fragments carrying amplification adapters with a suitable priming sequence can be present in much higher (1000 fold or more) concentration compared to linearly amplifiable or un-amplifiable fragments, after a PCR amplification. Benefits of PCR, as compared to whole genome amplification techniques (such as amplification with randomized primers or Multiple Displacement Amplification using phi29 polymerase) include, but are not limited to a more uniform relative sequence coverage—as each fragment can be copied at most once per cycle and as the amplification is controlled by thermocycling program, a substantially lower rate of forming chimeric molecules than for example MDA (Lasken et al, 2007, BMC Biotechnology)—as chimeric molecules pose significant challenges for accurate sequence assembly by presenting nonbiological sequences in the assembly graph, which may result in higher rate of misassemblies or highly ambigious and fragmented assembly, reduced sequence specific biases that may result from binding of randomized primers commonly used in MDA versus using specific priming sites with a specific sequence, a higher reproducibility in the amount of final amplified DNA product, which can be controlled by selection of the number of PCR cycles, and a higher fidelity in replication with the polymerases that are commonly used in PCR as compared to common whole genome amplification techniques known in the art.

In some embodiments, end repair is performed to generate blunt end 5' phosphorylated nucleic acid ends using commercial kits, such as those available from Epicentre Biotechnologies (Madison, Wis.).

An adapter oligonucleotide includes any oligonucleotide having a sequence, at least a portion of which is known, that can be joined to a target polynucleotide. Adapter oligonucleotides can comprise DNA, RNA, nucleotide analogues, non-canonical nucleotides, labeled nucleotides, modified nucleotides, or combinations thereof. Adapter oligonucleotides can be single-stranded, double-stranded, or partial duplex. In general, a partial-duplex adapter comprises one or more single-stranded regions and one or more double-stranded regions. Double-stranded adapters can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some embodiments, a single-stranded adapter comprises two or more sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. Adapters comprising a bubble structure can consist of a single adapter oligonucleotide comprising internal hybridizations, or may comprise two or more adapter oligonucleotides hybridized to one another. Internal sequence hybridization, such as between two hybridizable sequences in an adapter, can produce a double-stranded structure in a single-stranded adapter oligonucleotide. Adapters of different kinds can be used in combination, such as a hairpin adapter and a double-stranded adapter, or adapters of different sequences. Hybridizable sequences in a hairpin adapter may or may not include one or both ends of the oligonucleotide. When neither of the ends are included in the hybridizable sequences, both ends are "free" or "overhanging." When only one end is hybridizable to another sequence in the adapter, the other end forms an overhang, such as a 3' overhang or a 5' overhang. When both the 5'-terminal nucleotide and the 3'-terminal nucleotide are included in the hybridizable sequences, such that the 5'-terminal nucleotide and the 3'-terminal nucleotide are complementary and hybridize with one another, the end is referred to as "blunt." Different adapters can be joined to target polynucleotides in sequential reactions or simultaneously. For example, the first and second adapters can be added to the same reaction. Adapters can be manipulated prior to combining with target polynucleotides. For example, terminal phosphates can be added or removed.

Adapters can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. When an adapter oligonucleotide is capable of forming secondary structure, such as a hairpin, sequence elements can be located partially or completely outside the secondary structure, partially or completely inside the secondary structure, or in between sequences participating in the secondary structure. For example, when an adapter oligonucleotide comprises a hairpin structure, sequence elements can be located partially or completely inside or outside the hybridizable sequences (the "stem"), including in the sequence between the hybridizable sequences (the "loop"). In some embodiments, the first adapter oligonucleotides in a plurality of first adapter oligonucleotides having different barcode sequences comprise a sequence element common among all first adapter oligonucleotides in the plurality. In some embodiments, all second adapter oligonucleotides comprise a sequence element common among all second adapter oligonucleotides that is different from the common sequence element shared by the first adapter oligonucleotides. A difference in sequence elements can be any such that at least a portion of different adapters do not completely align, for example, due to changes in sequence length, deletion or insertion of one or more nucleotides, or a change in the nucleotide composition at one or more nucleotide positions (such as a base change or base modification). In some embodiments, an adapter oligonucleotide comprises a 5' overhang, a 3' overhang, or both that is complementary to one or more target polynucleotides.

Complementary overhangs can be one or more nucleotides in length, including but not limited to 1, 2, 3, 4, 5, 6, 7, 8, 9, 10, 11, 12, 13, 14, 15, or more nucleotides in length. Complementary overhangs may comprise a fixed sequence. Complementary overhangs may comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

Adapter oligonucleotides can have any suitable length, at least sufficient to accommodate the one or more sequence elements of which they are comprised. In some embodiments, adapters are about, less than about, or more than about 10, 15, 20, 25, 30, 35, 40, 45, 50, 55, 60, 65, 70, 75, 80, 90, 100, 200, or more nucleotides in length.

The terms "joining" and "ligation" as used herein, with respect to two polynucleotides, such as an adapter oligonucleotide and a target polynucleotide, refers to the covalent attachment of two separate polynucleotides to produce a single larger polynucleotide with a contiguous backbone. Methods for joining two polynucleotides are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adapter oligonucleotide is joined to a target polynucleotide by a ligase, for example a DNA ligase or RNA ligase. Multiple ligases, each having characterized reaction conditions, are known in the art, and include, without limitation NAD$^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Ligation can be between polynucleotides having hybridizable sequences, such as complementary overhangs. Ligation can also be between two blunt ends. Generally, a 5' phosphate is utilized in a ligation reaction. The 5' phosphate can be provided by the target polynucleotide, the adapter oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction (e.g. an adapter end and a target polynucleotide end) provide a 5' phosphate, such that two covalent linkages are made in joining the two ends. In some embodiments, only one of the two ends joined in a ligation reaction (e.g. only one of an adapter end and a target polynucleotide end) provides a 5' phosphate, such that only one covalent linkage is made in joining the two ends. In some embodiments, only one strand at one or both ends of a target polynucleotide is joined to an adapter oligonucleotide. In some embodiments, both strands at one or both ends of a target polynucleotide are joined to an adapter oligonucleotide. In some embodiments, 3' phosphates are removed prior to ligation. In some embodiments, an adapter oligonucleotide is added to both ends of a target polynucleotide, wherein one or both strands at each end are joined to one or more adapter oligonucleotides. When both strands at both ends are joined to an adapter oligonucleotide, joining can be followed by a cleavage reaction that leaves a 5' overhang that can serve as a template for the extension of the corresponding 3' end, which 3' end may or may not include one or more nucleotides derived from the adapter oligonucleotide. In some embodiments, a target polynucleotide is joined to a first adapter oligonucleotide on one end and a second adapter oligonucleotide on the other end. In some embodiments, two ends of a target polynucleotide are joined to the opposite ends of a single adapter oligonucleotide. In some embodiments, the target polynucleotide and the adapter oligonucleotide to which it is joined comprise blunt ends. In some embodiments, separate ligation reactions are carried out for each sample, using a different first adapter oligonucleotide comprising at least one barcode sequence for each sample, such that no barcode sequence is joined to the target polynucleotides of more than one sample. A target polynucleotide that has an adapter oligonucleotide joined to it is considered "tagged" by the joined adapter.

In some embodiments, joining of an adapter to a target polynucleotide produces a joined product polynucleotide having a 3' overhang comprising a nucleotide sequence derived from the adapter.

In some embodiments, after joining at least one adapter oligonucleotide to a target polynucleotide, the 3' end of one or more target polynucleotides is extended using the one or more joined adapter oligonucleotides as template. For example, an adapter comprising two hybridized oligonucleotides that is joined to only the 5' end of a target polynucleotide allows for the extension of the unjoined 3' end of the target using the joined strand of the adapter as template, concurrently with or following displacement of the unjoined strand. Both strands of an adapter comprising two hybridized oligonucleotides may be joined to a target polynucleotide such that the joined product has a 5' overhang, and the complementary 3' end can be extended using the 5' overhang as template. As a further example, a hairpin adapter oligonucleotide can be joined to the 5' end of a target polynucleotide. In some embodiments, the 3' end of the target polynucleotide that is extended comprises one or more nucleotides from an adapter oligonucleotide. For target polynucleotides to which adapters are joined on both ends, extension can be carried out for both 3' ends of a double-stranded target polynucleotide having 5' overhangs. This 3' end extension, or "fill-in" reaction, generates a complementary sequence, or "complement," to the adapter oligonucleotide template that is hybridized to the template, thus filling in the 5' overhang to produce a double-stranded sequence region. Where both ends of a double-stranded target polynucleotide have 5' overhangs that are filled in by extension of the complementary strands' 3' ends, the product is completely double-stranded. Extension can be carried out by any suitable polymerase known in the art, such as a DNA polymerase, many of which are commercially available. DNA polymerases can comprise DNA-dependent DNA polymerase activity, RNA-dependent DNA polymermase activity, or DNA-dependent and RNA-dependent DNA polymerase activity. DNA polymerases can be thermostable or non-thermostable. Examples of DNA polymerases include, but are not limited to, Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, Klenow fragment, and variants, modified products and derivatives thereof 3' end extension can be performed before or after pooling of target polynucleotides from independent samples.

In some embodiments, the fill-in reaction is followed by or performed as part of amplification of one or more target polynucleotides using a first primer and a second primer, wherein the first primer comprises a sequence that is hybridizable to at least a portion of the complement of one or more of the first adapter oligonucleotides, and further wherein the second primer comprises a sequence that is hybridizable to at least a portion of the complement of one or more of the second adapter oligonucleotides. Each of the first and second primers may be of any suitable length, such as about, less than about, or more than about 10, 15, 20, 25, 30, 35, 40, 45, 50, 55, 60, 65, 70, 75, 80, 90, 100, or more nucleotides, any portion or all of which may be complementary to the corresponding target sequence (e.g. about, less than about, or more than about 5, 10, 15, 20, 25, 30, 35, 40, 45, 50, or more nucleotides). "Amplification" refers to any process by which the copy number of a target sequence is increased. Methods for primer-directed amplification of target polynucleotides are known in the art, and include without limitation, methods based on the polymerase chain reaction (PCR). Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adapter fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 50, or more cycles. In some embodiments, amplification is performed following the fill-in reaction. Amplification can be performed before or after pooling of target polynucleotides from independent samples.

In some embodiments, target polynucleotides from independent samples are pooled after the joining step. Pooling can be performed immediately after the joining step, or following one or more intervening steps between joining and pooling. Pools can comprise any fraction of the total target polynucleotides from a joining reaction, including the whole reaction volume. Samples can be pooled evenly or unevenly. Target polynucleotides can be further processed before or after pooling, for example to purify desired products or eliminate undesired products. Pools can comprise polynucleotides from any number of independent samples, such as at least 2, 3, 4, 5, 6, 7, 8, 9, 10, 12, 16, 20, 24, 28, 32, 36, 40, 50, 60, 70, 80, 90, 100, 128, 192, 384, 500, 1000 or more samples. In some embodiments, target polynucleotides are pooled based on the barcodes to which they are joined. In some embodiments, target polynucleotides from independent samples are pooled such that all four bases are evenly represented at one or more positions along the barcode, among barcodes included in the pool. In some embodiments, target polynucleotides from independent samples are pooled such that all four bases are evenly represented at every position along the barcode, among barcodes included in the pool. Where only one barcode is joined to polynucleotides of each sample, samples can be pooled in multiples of four in order to represent all four bases at one or more positions along the barcode evenly, for example 4, 8, 12, 16, 20, 24, 28, 32, 36, 40, 44, 48, 52, 56, 60, 64, 96, 128, 192, 256, 384, and so on. Where two barcodes are included in the joining reaction for each sample, such as two different first adapter oligonucleotides or one first adapter oligonucleotide and one second adapter oligonucleotide each having barcodes, samples can be pooled in multiples of two in order to evenly represent all four bases at one or more positions along the barcode, for example 2, 4, 6, 8, 10, 12, 14, 16, 18, 20, 22, 24, 48, 64, 96, 128, 256, 384, and so on. All combinations of the number of barcodes included in the joining reaction for target polynucleotides from each sample and the multiples in which samples are pooled in order to evenly represent all four nucleotides at one or more positions along the barcode are contemplated by the methods of the invention.

In some embodiments, pooling of target polynucleotides is followed by sequencing one or more polynucleotides in the pool. Sequencing processes are generally template dependent. Nucleic acid sequence analysis that employs template dependent synthesis identifies individual bases, or groups of bases as they are added during a template mediated synthesis reaction, such as a primer extension reaction, where the identity of the base is complementary to the template sequence to which the primer sequence is hybridized during synthesis. Other such processes include ligation driven processes, where oligonucleotides or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Amplification adapters may be attached to the fragmented nucleic acid. Amplification adapters may be attached prior or subsequent to partitioning the nucleic acid. Adapters may be commercially obtained, such as from Integrated DNA Technologies (Coralville, Iowa). In certain embodiments, the adapter sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase (such ligases are available commercially, from New England Biolabs). The polymerase may be any enzyme capable of adding nucleotides to the 3' and the 5' terminus of template nucleic acid molecules. Alternatively, amplification adapters can be added to the target polynucleotide of interest via an intermediate polynucleotide that is comprised of two or more amplification adapters.

Figure 6:
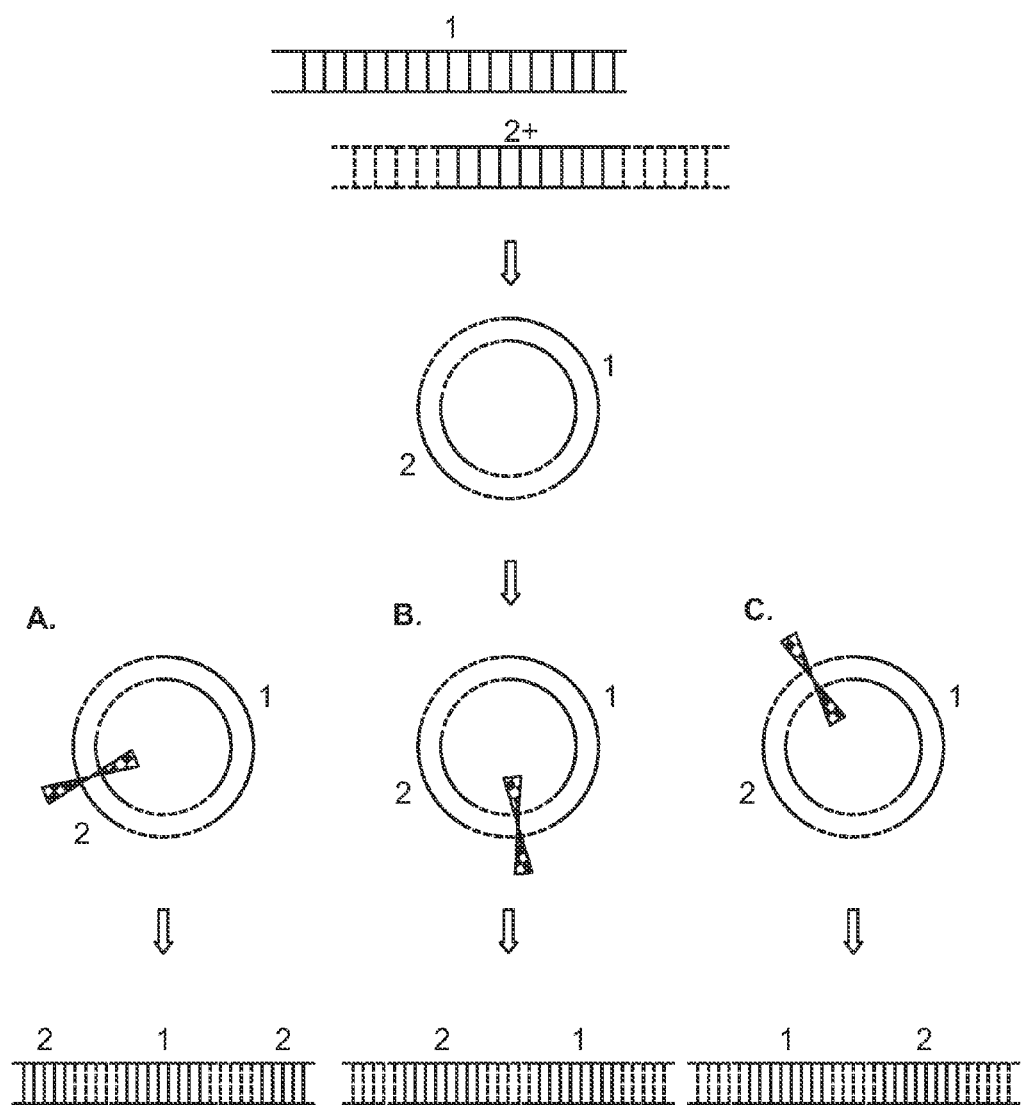
FIG. 6 demonstrates an example of attaching adapters to target polynucleotide according to some embodiments of the invention.

The adapters can be added by ligating a target polynucleotide to an intermediate polynucleotide comprised of compatible adapter ends. The compatible adapter ends can be kept under ligation conditions usually including a ligase, which facilitates the nucleic acid ends to intermolecularly ligate, thereby producing a circularized nucleic acid molecule. In some embodiments, the intermediate polynucleotide comprises a cleavable adapter thereby allowing the transformation of the circular polynucleotide into a linearized molecule with adapters located at each end (FIG. 6 A, B,C). The cleavable adapter may comprise a restriction endonuclease recognition site specific for a restriction endonuclease. The intermediate polynucleotide may comprise a cleavable adapter, for example a nicked adapter. For another example, the adaptor may comprise a cleavable adapter. The cleavable site in the adapter may be a deoxyuridine nucleotide which can be cleaved by uracil DNA glycosylase (UDG) and an AP-lyase. The cleavable adapter may comprise a 3' phosphorothiolate linkage cleaved by a metal ion, included but not limited to $Ag^+$, $Hg^{2+}$ or $Cu^{2+}$. The cleavage reaction may be at a pH of at least about 5 to 9. The temperature for the cleavage reaction may be selected at a temperature of about 22° to 37° degrees Celsius.

There are several ligation methods that can be employed to attach the adapters to a target polynucleotide. Ligation methods can include directional cloning, which uses "sticky ends". Sticky can be are generated by treating a polynucleotide with restriction enzymes to create complementary over-hanging ends. In the presence of a ligase complementary over-hanging ends may be ligated together. Ligation can be performed using non-directional cloning methods by the use of "blunt ends". In certain embodiments, following fragmentation, the ends of the fragments may be repaired, trimmed (e.g. using an exonuclease), or filled (e.g., using a polymerase and dNTPs), to form blunt ends. The blunt ends may have phosphates at the 5' ends and a hydroxyl at each 3' end of the target polynucleotide and the intermediate polynucleotide; alternatively, one or more 5' ends may lack a 5' phosphate. In the presence of a ligase enzyme, the blunt ends phosphates at the 5' ends and hydroxyl at the 3' ends may be ligated together. In certain embodiments, single strand overhangs can be removed to form blunt ends by the use of particular exonucleases that cut free single strand nucleic acids but do not cut double strand nucleic acids. Examples of such exonucleases include, but are not limited to: Exo VII, Exonuclease I, Exonuclease T, Lambda Exonuclease, and T7 Exonuclease.

Alternatively, one could ligate the target polynucleotide and the intermediate polynucleotide using T-A end cloning method. T-A cloning is a subcloning technique that does not use restriction enzymes generated sticky ends. Upon generating blunt ends, the ends can be treated with a polymerase and dATP to form a template independent addition to the 3'-end and the 5'-end of the fragments, thus producing a single A overhanging. The T-A cloning technique relies on the ability of adenine (A) and thymine (T) to complementary base pair on different DNA fragments to hybridize and, in the presence of ligase to form a circular polynucleotide. Alternatively, an investigator can use PCR generated fragments that already contain an "A" overhang by employing a DNA polymerase that leaves an adenine "A" nucleotide at the 3' end during amplification, such as Taq DNA polymerase or equivalents. Thermostable polymerases containing extensive 3' to 5' exonuclease activity are not suitable for this purpose, as they do not leave the 3' adenine-overhangs. The probability of Taq DNA polymerase adding the terminal adenosine overhang may be increased by using PCR primers that have guanines at the 5' end. In another example, thymines (T) can be added using a dideoxythymidine triphosphate (ddTTP) and a terminal transferase. This tailing leaves the vector with a single 3'-overhanging thymine residue on each blunt end. Similarly, one could use G-C cloning in the presence of ligase to form a circular polynucleotide. Commercialized kits with pre-prepared reagents and terminal transferases are available T-A or G-C cloning and well known in the art. T-A/G-C cloning are best utilized when directional cloning is not a requirement.

According to one method the target polynucleotide can be ligated by PCR to the intermediate polynucleotide, by generating a circularized form using a topoisomerase using an intermediate polynucleotide with adapters. In some embodiments, the adapters contain a 5'-(C/T)CCTT-3' recognition site at the 3' ends. The intermediate polynucleotide may contain a topoisomerase enzyme covalently attached to the recognition site generating an intermediate polynucleotide-TOPO modified molecule. The intermediate-TOPO polynucleotide may be mixed with target polynucleotides generated by PCR, allowing for recognition of the intermediate polynucleotide-TOPO 3' by the 5' ends. The strands may be covalently linked by the topoisomerase to form a circular polynucleotide.

In some applications, amplification adapters are added to a target polynucleotide. The target polynucleotide can be single or double stranded. accordingly, the adapters can be either single stranded or double stranded depending on whether the target polynucleotide employed is single or double stranded. A single strand target template may originate from RNA or DNA. CircLigase™ II is a thermostable ssDNA ligase that catalyzes intramolecular ligation of ssDNA templates having a 5'-phosphate and a 3'-hydroxyl group (Epicentre). The target polynucleotide can be further obtained from fragmentation of large DNA or RNA molecules, PCR amplification or from cloned vectors containing the target sequence of interest, such as a commercial cloned gene expression libraries of RNA or DNA.

Figure 5A:
FIGS. 5A-B are schematics showing that end markers can be attached by circularizing long fragments and using a pool of circularization adapters that contain matched pairs of known sequences that are ligated to opposite ends of long fragments.
Figure 5A:
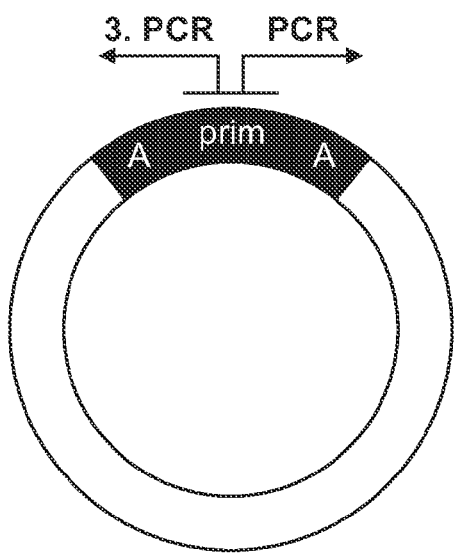
Figure 5A:
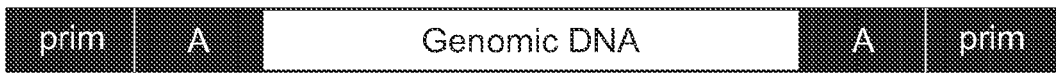
Figure 5B:
Figure 5B:
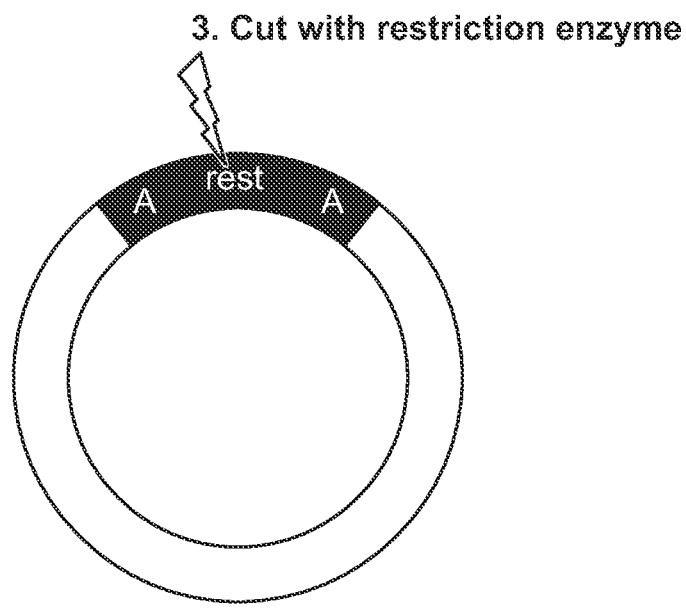
Figure 5B:
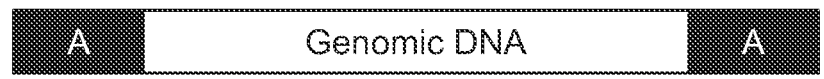

In some embodiments of the invention, end markers/adapters can be attached by circularizing long fragments and using a pool of circularization adapters that contain matched pairs of known sequences that are ligated to opposite ends of long fragments. Such paired adapters may be attached to long fragments allowing for validation of long fragment assembly, for example by checking whether a correctly matching pair of adapters is found on opposite ends of a reconstructed fragment (FIGS. 5A-B).

The ratio of the target polynucleotide and the intermediate polynucleotide within the circular polynucleotide may be varied. In such cases, reiterative steps described above may be performed using multiple cloning site identification elements or nicked identification elements contained within the adapters. Accordingly, a circular polynucleotide containing more than a 1:1 target polynucleotide: intermediate polynucleotide ratio may be generated. In some embodiments, target polynucleotide and the intermediate polynucleotide are present at a 1:2, 1:3, 1:4, 1:6, 1:8, 1:10 or 1:20 ratio.

Adapters containing particular identification elements may be used and may be useful in downstream analysis of the target polynucleotide. More specifically, one could use adapters that contain a unique tag identification element. Tags can include, but are not limited to, for example, a fluorophore, a quantum dot, a dendrimer, a nanowire, a bead, a peptide, a protein, a magnetic bead, a methyl group, a methyltransferase, a non-cutting restriction enzyme, a zinc-finger protein, an antibody, a transcription factor, a DNA binding protein, a hairpin polyamide, a triplex-forming oligodeoxynucleotide, a peptide nucleic acid, a nucleic acid or the equivalents thereof. The methods may include the use of two or more different tags, and a single molecule may accordingly include multiple tags. In some embodiments, a unique tag can be a synthetic or a unique sequence of natural nucleotides that allows for easy identification of the target polynucleotide within a complicated pool of oligonucleotides containing various sequences. In certain embodiments, unique identifiers are attached to the nucleic acid fragments prior to attaching the adapter sequences. In a some embodiments, unique marker identifiers are contained within adapter sequences such that the unique marker sequence is partially contained in the sequencing reads obtained from boundaries of long fragments. This ensures that homologous fragments can be detected based upon the unique markers that are attached to each fragment, thus further providing for unambiguous reconstruction of a consensus sequence. Homologous fragments may occur for example by chance due to genomic repeats, two fragments originating homologous chromosomes, or fragments originating from overlapping locations on the same chromosome. Such fragments may be discarded to ensure that long fragment assembly can be computed unambiguously. The markers may be attached as described above for the adapter sequences. The markers may be included in the adapter sequences.

In some cases, samples may need multiple additional manipulations. An adapter, such as one described above, with a multiple cloning site identification element may be used for additional steps. A multiple cloning site, is a short segment of DNA which contains many, for example up to ~20 restriction enzyme recognition sites. This feature in the adapter can be used for iterative rounds of molecular cloning or subcloning to allow for insertion of a piece of DNA or several pieces of DNA into the multiple cloning site identification elements. This method can be used to vary the ratio of the target polynucleotide and adapter sequences. Alternatively, it can be used to tailor an adapter sequence with specific identification elements within the adapter. In another embodiment, one can modify or concatenate particular identification elements comprising the adapter using nicked or single nucleotide regions site contained in the adapter identification element.

In some applications, parallel amplification of the target polynucleotides is desirable. End adapters with a universal priming site for a DNA polymerase may be utilized for parallel amplification. With adapters located at each end, the target polynucleotides can be simultaneously amplified using universal primers that are sufficiently complementary to a universal priming site allowing for hybridization to upstream and downstream universal priming sequences in the adapters.

In some instances, more controlled amplification of a target polynucleotide may be facilitated, by using an adapter comprising a specific recognition site for a transcription factor. Specifically, an adapter containing a specific transcriptional promoter sequence that is recognized by a particular polymerase can be utilized. Examples of such polymerases include, but are not limited to T7, T3, SP6, or homologues thereof. Such methods can further be employed when it is desirable to transform a single stranded molecule into a double stranded molecule.

In some embodiments, the adapter sequences can contain a molecular binding site identification element to facilitate identification and isolation of the target polynucleotide for downstream applications. Molecular binding as affinity mechanism allows for the interaction between two molecules to result in a stable association complex. Molecules that can participate in molecular binding reactions include: proteins, nucleic acids, carbohydrates, lipids, and small organic molecules such as ligands, peptides or drugs.

One example of protein-protein molecular binding is affinity mechanism is the avidin-biotin system. Avidin, has a high binding affinity for the molecule, biotin. A biotinylated adapter may be used in the intermediate polynucleotide by synthesizing the adapter sequence with biotinaltyed-dNTPs, which are well known in the art. Following the ligation of the target polynucleotide to the biotinaltyed adapters, the biotinaltyed target polynucleotide can be captured using streptavidin magnetic beads. In another embodiment, the molecular binding site is selected from the group consisting of, digoxigenin, a hapten, a ligand, a peptide and a nucleic acid.

When a nucleic acid molecular binding site is used as part of the adapter, it can be used to employ selective hybridization to isolate the target sequence. Selective hybridization may restrict substantial hybridization to target polynucleotides containing the adapter with the molecular binding site and capture nucleic acids, which are sufficiently complementary to the molecular binding site. Thus, through "selective hybridization" one can detect the presence of the target polynucleotide in an unpure sample containing a pool of many polynucleotides. An example of a nucleotide-nucleotide selective hybridization isolation system comprises a system with several capture nucleotides, which are complementary sequences to the molecular binding identification elements, and are optionally immobilized to a solid support. In other embodiments, the capture polynucleotides could be complementary to the target sequences itself or a barcode or unique tag contained within the adapter. The capture polynucleotides can be immobilized to various solid supports, such as inside of a well of a plate, mono-dispersed spheres, microarrays, or any other suitable support surface known in the art. The hybridized complementary adapter polynucleotides attached on the solid support can be isolated, by washing away the undesirable non-binding polynucleotides, leaving the desirable target polynucleotides behind. If complementary adapter molecules are fixed to paramagnetic spheres or similar bead technology for isolation, then spheres can then be mixed in a tube together with the target polynucleotide containing the adapters. When the adapter sequences have been hybridized with the complementary sequences fixed to the spheres, undesirable molecules can be washed away while spheres are kept in the tube with a magnet or similar agent. The desired target molecules can be subsequently released by increasing the temperature, changing the pH, or by using any other suitable elution method known in the art.

In some embodiments, the adapter comprises a nicked adapter. Accordingly, the adapter may contain a single-stranded region within a predominantly double stranded adapter. Such single-stranded regions can take the form of gaps interior to a duplex, or alternatively can be located at the ends forming terminal single-stranded regions. Nicked adapters can be made by several methods. One method is by the use of nickases. Nickases are endonucleases that recognize a specific recognition sequence in double-stranded nucleic acid molecules, and cut one strand at a specific location relative to the recognition sequence, thereby giving rise to single-stranded gaps in duplex DNA. The nicking enzyme may nick one or more of a DNA duplex, an RNA/DNA hybrid and an RNA duplex. Three major sources obtaining sequence-specific DNA nicking enzymes include nicking enzymes from *Chlorella* algae viruses, from which N.CviQXI (CviNY2A) and N.CviPII (CviNYSI) were originally found (Zhang Y. et al. Virology, 240:366-375 (1998); Xia Y. et al. Nucl. Acids Res. 16:9477-9487 (1988)), bacteria in which N.BstNBI and N.BstSEI were discovered (Morgan R. D. et al. Biol. Chem. 381:1123-5 (2000); Abdurashitov, et al., Mol. Biol. (Mosk) 30:1261-1267 (1996)), and enzymes generated by protein engineering from existing Type IIA restriction enzymes. Examples of nickases that can be used include but are not limited to Nb.BsrDI, Nb.BsmI, Nt.BbvCI, Nb.Bbv.Nb.BtsI and Nt.BstNBI. Site-specific DNA nicking endonucleases are used to form the single-stranded regions by nicking at the boundaries of the single-strand regions, either on opposing DNA strands (creating terminal single-stranded regions) or on the same strand (creating a single-strand gap). The skilled artisan will appreciate that any other site-specific nicking enzyme would give equivalent results. In other aspect of the invention, a nicked adapter can be made by incorporating uracil into one strand of an adaptor sequence and nicking is accomplished subsequently by using uracil-DNA glycosylase which acts by limiting uracil from DNA molecules by cleaving the N-glycosylic bond.

In other aspects of the invention, nicked regions can also be used for several applications including: joining, detecting, cutting and purifying the unpaired adapter regions containing the nick site. Such application can be carried out by restriction enzymes which preferentially cleave single stranded nucleic acids. In one aspect the nicked adapter can used to make a preferred cleavage site for a restriction endonuclease thereby linearizing the circularized polynucleotide. In general, various restriction enzymes can cut single stranded nucleic acids under the correct conditions. Examples of restriction endonucleases that preferentially cleave single-stranded nucleotide regions include, but are not limited, HhaI and CfoI, or equivalents thereof. Alternatively, a general restriction enzyme can be employed to cleave single stranded nucleic acids.

Single-stranded nicked regions within the adapter can facilitate the assembly of multiple nucleic acid fragments and intermediate polynucleotides. This is useful in the construction of intermediate polynucleotide with particular adapter identification elements discussed herein. These applications include strand displacement DNA amplification. Strand displacement DNA amplification, includes introducing a specific nick in the target polynucleotide by a nicking enzyme. Strand displacement DNA polymerase or other equivalent DNA polymerases can initiate a new strand synthesis at the nick and displace the nicked strand, resulting in linear DNA amplification products.

Nicked DNA can also be used to facilitate recombinant DNA technology for gene fragment assembly. Staggered nicks can be introduced in top and bottom strands to generate large cohesive ends (e.g. 8 to 20 nt long). The complementary cohesive ends can anneal together and bypass the ligation step. Nicking enzymes can also be used in preparation of ssDNA ends for DNA fragment assembly in linear or circular form. Strand-specific DNA nicking enzymes can be used to form single-stranded regions by nicking at the boundaries of the single-stranded regions, either on opposing DNA strands, creating terminal single-stranded regions, or on the same strand, creating single-stranded gap regions. Duplex DNA containing a single nick exhibits altered migration through agarose or ploycrylamide gel-based assays. The altered migration characteristic can be used for isolation and purification of the target polynucleotide using standard nucleic acid purification techniques known in the art.

As used herein, the term "barcode" refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are at least 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differ from every other barcode in the plurality at least two nucleotide positions, such as at least 2, 3, 4, 5, 6, 7, 8, 9, 10, or more positions. In some embodiments, both a first adapter and a second adapter comprise at least one of a plurality of barcode sequences. In some embodiments, barcodes for second adapter oligonucleotides are selected independently from barcodes for first adapter oligonucleotides. In some embodiments, first adapter oligonucleotides and second adapter oligonucleotides having barcodes are paired, such that adapters of the pair comprise the same or different one or more barcodes. In some embodiments, the methods of the invention further comprise identifying the sample from which a target polynucleotide is derived based on a barcode sequence to which the target polynucleotide is joined. In general, a barcode may comprise a nucleic acid sequence that when joined to a target polynucleotide serves as an identifier of the sample from which the target polynucleotide was derived.

FIGS. 5A-B show an embodiment in which a short bar code (for example 4 bp) is added to the end markers. In certain embodiments, the same end-signal bar code is on both sides of the 10 kb molecule. Thus, after assembling the 10 kb reads, one can tell that there's no misassembly by making sure that the two ends have the same bar code. In other embodiments, the bar codes on both ends are different. In these embodiments, it is only important that the relationship between the two bar codes be known. So one could use a set of bar codes, for example "A-primer-B" and "Q-primer-R" (here A, B, Q, and R represent a short bar code, e.g. 4-nt long sequence), as long as the links A-B and Q-R are known.

In certain embodiments, ligation is used to place the same barcode on both sides (FIG. 5A, bar codes are denoted "A" and the results goes "A-primer-A"). The nucleic acid is then circularize and amplified from the primer site in the middle (in both directions; FIG. 5A). Alternatively, one could ligate a construct of the form "A-primer1-restriction-primer2-A" and then after circularization use a restriction enzyme to cut at the "restriction" size, followed by PCR of primer1 and primer2 to amplify (FIG. 5B). Methods of the invention involve determining an amount of amplifiable nucleic acid present in a sample. Any known method may be used to quantify amplifiable nucleic acid, and an exemplary method is the polymerase chain reaction (PCR), specifically quantitative polymerase chain reaction (QPCR). QPCR is a technique based on the polymerase chain reaction, and is used to amplify and simultaneously quantify a targeted nucleic acid molecule. QPCR allows for both detection and quantification (as absolute number of copies or relative amount when normalized to DNA input or additional normalizing genes) of a specific sequence in a DNA sample. The procedure follows the general principle of polymerase chain reaction, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567,583 and 5,348,853), Ma et al. (The Journal of American Science, 2(3), 2006), Heid et al. (Genome Research 986-994, 1996), Sambrook and Russell (Quantitative PCR, Cold Spring Harbor Protocols, 2006), and Higuchi (U.S. Pat. Nos. 6,171,785 and 5,994,056). The contents of these are incorporated by reference herein in their entirety.

Two common methods of quantification are: (1) use of fluorescent dyes that intercalate with double-stranded DNA, and (2) modified DNA oligonucleotide probes that fluoresce when hybridized with a complementary DNA. In the first method, a DNA-binding dye binds to all double-stranded (ds)DNA in PCR, resulting in fluorescence of the dye. An increase in DNA product during PCR therefore leads to an increase in fluorescence intensity and is measured at each cycle, thus allowing DNA concentrations to be quantified. The reaction is prepared similarly to a standard PCR reaction, with the addition of fluorescent (ds)DNA dye. The reaction is run in a thermocycler, and after each cycle, the levels of fluorescence are measured with a detector; the dye only fluoresces when bound to the (ds)DNA (i.e., the PCR product). With reference to a standard dilution, the (ds)DNA concentration in the PCR can be determined. Like other real-time PCR methods, the values obtained do not have absolute units associated with it. A comparison of a measured DNA/RNA sample to a standard dilution gives a fraction or ratio of the sample relative to the standard, allowing relative comparisons between different tissues or experimental conditions. To ensure accuracy in the quantification, it is important to normalize expression of a target gene to a stably expressed gene. This allows for correction of possible differences in nucleic acid quantity or quality across samples.

The second method uses a sequence-specific RNA or DNA-based probe to quantify only the DNA containing the probe sequence; therefore, use of the reporter probe significantly increases specificity, and allows quantification even in the presence of some non-specific DNA amplification. This allows for multiplexing, i.e., assaying for several genes in the same reaction by using specific probes with differently colored labels, provided that all genes are amplified with similar efficiency.

This method is commonly carried out with a DNA-based probe with a fluorescent reporter (e.g. 6-carboxyfluorescein) at one end and a quencher (e.g., 6-carboxy-tetramethylrhodamine) of fluorescence at the opposite end of the probe. The close proximity of the reporter to the quencher prevents detection of its fluorescence. Breakdown of the probe by the 5' to 3' exonuclease activity of a polymerase (e.g., Taq polymerase) breaks the reporter-quencher proximity and thus allows unquenched emission of fluorescence, which can be detected. An increase in the product targeted by the reporter probe at each PCR cycle results in a proportional increase in fluorescence due to breakdown of the probe and release of the reporter. The reaction is prepared similarly to a standard PCR reaction, and the reporter probe is added. As the reaction commences, during the annealing stage of the PCR both probe and primers anneal to the DNA target. Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in a real-time PCR thermocycler, and geometric increase of fluorescence corresponding to exponential increase of the product is used to determine the threshold cycle in each reaction.

Relative concentrations of DNA present during the exponential phase of the reaction are determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, $C_t$. Since the quantity of DNA doubles every cycle during the exponential phase, relative amounts of DNA can be calculated, e.g. a sample with a $C_t$ of 3 cycles earlier than another has $2^3=8$ times more template. Amounts of nucleic acid (e.g., RNA or DNA) are then determined by comparing the results to a standard curve produced by a real-time PCR of serial dilutions (e.g. undiluted, 1:4, 1:16, 1:64) of a known amount of nucleic acid.

In certain embodiments, the QPCR reaction involves a dual fluorophore approach that takes advantage of fluorescence resonance energy transfer (FRET), e.g., LIGHTCYCLER hybridization probes, where two oligonucleotide probes anneal to the amplicon (e.g. see U.S. Pat. No. 6,174,670). The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: SCORPIONS probes (e.g., Whitcombe et al., Nature Biotechnology 17:804-807, 1999, and U.S. Pat. No. 6,326,145), Sunrise (or AMPLIFLOUR) primers (e.g., Nazarenko et al., Nuc. Acids Res. 25:2516-2521, 1997, and U.S. Pat. No. 6,117,635), and LUX primers and MOLECULAR BEACONS probes (e.g., Tyagi et al., Nature Biotechnology 14:303-308, 1996 and U.S. Pat. No. 5,989,823).

In other embodiments, the QPCR reaction uses fluorescent Taqman methodology and an instrument capable of measuring fluorescence in real time (e.g., ABI Prism 7700 Sequence Detector). The Taqman reaction uses a hybridization probe labeled with two different fluorescent dyes. One dye is a reporter dye (6-carboxyfluorescein), the other is a quenching dye (6-carboxy-tetramethylrhodamine). When the probe is intact, fluorescent energy transfer occurs and the reporter dye fluorescent emission is absorbed by the quenching dye. During the extension phase of the PCR cycle, the fluorescent hybridization probe is cleaved by the 5'-3' nucleolytic activity of the DNA polymerase. On cleavage of the probe, the reporter dye emission is no longer transferred efficiently to the quenching dye, resulting in an increase of the reporter dye fluorescent emission spectra. Any nucleic acid quantification method, including real-time methods or single-point detection methods may be use to quantify the amount of nucleic acid in the sample. The detection can be performed several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment), as well as any other suitable detection method known in the art for nucleic acid quantification. The quantification may or may not include an amplification step.

The results of the quantitation can be used to determine the proper dilution for partitioning before the sequencing steps. The quantitation may not be experimental. The amount of nucleic acid in the pre-partitioned sample can be determined using various methods or the sample may be supplied with the amount of nucleic acid predetermined. In various embodiments, the fractioned sample is amplified, e.g. using a PCR step. Particularly, the fragmented nucleic acids are partitioned based upon results of the determining step such that each partitioned portion includes, on average, a subset of unique sequences. Limiting the number of amplifiable molecules per partitioned portion greatly reduces or eliminates chances of having a repeated sequence within a partitioned portion. Thus, sample complexity within each partitioned portion is significantly reduced as compared to the original sample, which allows for unambiguous reconstruction of a consensus sequence.

In certain embodiments, the partitioning is performed under microfluidic control. In other embodiments, partitioning involves dispensing the sample into different wells of a microwell plate. Such diluting and dispensing is described for example in Brown et al. (U.S. Pat. Nos. 6,143,496 and 6,391,559), the content of each of which is incorporated by reference herein in its entirety. In certain embodiments, there is, on average, only a single nucleic acid fragment in each well.

In other embodiments, partitioning involves segmenting the sample into droplets. In certain embodiments, there is only a single nucleic acid fragment in each droplet. Droplet forming methods are known in the art and described for example in Davies et al. (U.S. Pat. Nos. 7,993,911; 7,622,076 and U.S. patent application numbers 2010/0304446; 2010/0109320; 2010/0092973; 2010/0075312; and 2008/0277494); Griffiths et al. (U.S. Pat. Nos. 6,489,103; 6,808,882; 7,138,233; 7,252,943; 7,582,446; 7,638,276; 7,897,341; and 7,968,287 and U.S. patent application numbers 2010/0210479; 2009/0325236; and 2009/0197772); Link et al. (U.S. patent application numbers 2011/0000560; 2010/0137163; and 2010/0105866); Stone et al. (U.S. Pat. No. 7,708,949 and U.S. patent application number 2010/0172803), and Anderson et al. (U.S. Pat. No. 7,041,481 and which reissued as RE41,780), the content of each of which is incorporated by reference herein in its entirety.

Generally, a sample fluid becomes dispersed into coflowing streams of an immiscible fluid, such as an oil) to form monodisperse droplets. These droplets can be flowed through channels and reactions can be conducted in the droplets. Briefly, droplet forming devices generally include an inlet channel, and outlet channel, and at least one carrier fluid channel. The channels are configured to meet at a junction. The inlet channel flows sample fluid to the junction, and the carrier fluid channels flow a carrier fluid that is immiscible with the sample fluid to the junction. The inlet channel narrows at its distal portion where it connects to the junction. The inlet channel is oriented to be perpendicular to the carrier fluid channels. Droplets are formed as sample fluid flows from inlet channel to the junction, where the sample fluid interacts with the flowing carrier fluid provided to the junction by carrier fluid channels, thus forming droplets of sample fluid in the carrier fluid that flow to the outlet channel.

The fragmented nucleic acids are then amplified in each partitioned portion. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyperbranched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAs is from Hitachi Software Engineering. The TM (melting or annealing temperature) of each primer is calculated using software programs such as Oligo Design, available from Invitrogen Corp.

To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other, and therefore, this length is a controllable parameter.

With PCR, it is possible to amplify a single copy of a specific target sequence in genomic DNA to a level that can be detected by several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g., genes) for insertion into recombinant vectors.

Methods for performing PCR in droplets are shown for example in Link et al. (U.S. patent application numbers 2008/0014589, 2008/0003142, and 2010/0137163) and Anderson et al. (U.S. Pat. No. 7,041,481 and which reissued as RE41,780), the content of each of which is incorporated by reference herein in its entirety.

Other amplification methods and strategies can also be utilized to detect nucleic acids in biological fluids. For example, another approach would be to combine PCR and the ligase chain reaction (LCR). Since PCR amplifies faster than LCR and requires fewer copies of target DNA to initiate, PCR can be used as first step followed by LCR. The amplified product could then be used in a LCR or ligase detection reaction (LDR) in an allele-specific manner that would indicate if a mutation was present. Another approach is to use LCR or LDR for both amplification and allele-specific discrimination. The later reaction is advantageous in that it results in linear amplification. Thus the amount of amplified product is a reflection of the amount of target DNA in the original specimen and therefore permits quantitation.

LCR utilizes pairs of adjacent oligonucleotides which are complementary to the entire length of the target sequence (Barany F. (1991) PNAS 88:189-193; Barany F. (1991) PCR Methods and Applications 1:5-16). If the target sequence is perfectly complementary to the primers at the junction of these sequences, a DNA ligase will link the adjacent 3' and 5' terminal nucleotides forming a combined sequence. If a thermostable DNA ligase is used with thermal cycling, the combined sequence will be sequentially amplified. A single base mismatch at the junction of the oligonucleotides will preclude ligation and amplification. Thus, the process is allele-specific. Another set of oligonucleotides with 3' nucleotides specific for the mutant would be used in another reaction to identify the mutant allele. A series of standard conditions could be used to detect all possible mutations at any known site. LCR typically utilizes both strands of genomic DNA as targets for oligonucleotide hybridization with four primers, and the product is increased exponentially by repeated thermal cycling.

A variation of the reaction is the ligase detection reaction (LDR) which utilizes two adjacent oligonucleotides which are complementary to the target DNA and are similarly joined by DNA ligase (Barany F. (1991) PNAS 88:189-193). After multiple thermal cycles the product is amplified in a linear fashion. Thus the amount of the product of LDR reflects the amount of target DNA. Appropriate labeling of the primers allows detection of the amplified product in an allele-specific manner, as well as quantitation of the amount of original target DNA. One advantage of this type of reaction is that it allows quantitation through automation (Nickerson et al. (1990) PNAS 87: 8923-8927).

The amplified nucleic acid in each partitioned portion may then be fragmented. Bar code sequences may be attached to these fragments. In various embodiments, the bar code sequences label the nucleic acid fragments in a partition specific manner. Lengths and sequences of bar code sequences can be designed to achieve a desired level of accuracy determining the identity of the partition. Bar code sequences can be designed such that after a tolerable number of point mutations, the identity of the partition can still be deduced with a desired accuracy. The amplified nucleic acid may be fragmented or sheared to a desired length using a variety of mechanical, chemical and/or enzymatic methods. In certain embodiments, a Tn-5 transposase (commercially available from Epicentre Biotechnologies; Madison, Wis.) cuts the amplified nucleic acid into fragments and inserts short pieces of DNA into the cuts. The short pieces of DNA are used to incorporate the bar code sequences.

Attaching bar code sequences to nucleic acid templates is shown in Kahvejian et al. (U.S. patent application number 2008/0081330), and Steinman et al. (International patent application number PCT/US09/64001), the content of each of which is incorporated by reference herein in its entirety. Methods for designing sets of bar code sequences and other methods for attaching bar code sequences are shown in U.S. Pat. Nos. 6,138,077; 6,352,828; 5,636,400; 6,172,214; 6235, 475; 7,393,665; 7,544,473; 5,846,719; 5,695,934; 5,604, 097; 6,150,516; RE39,793; 7,537,897; 6172,218; and 5,863, 722, the content of each of which is incorporated by reference herein in its entirety. In certain embodiments, a single bar code is attached to each fragment. In other embodiments, a plurality of bar codes, e.g., two bar codes, are attached to each fragment.

The bar code sequence generally includes certain features that make the sequence useful in sequencing reactions. For example the bar code sequences are designed to have minimal or no homopolymer regions, i.e., 2 or more of the same base in a row such as AA or CCC, within the bar code sequence. The bar code sequences are also designed so that they are at least one edit distance away from the base addition order when performing base-by-base sequencing, ensuring that the first and last base do not match the expected bases of the sequence.

The bar code sequences are designed such that each sequence is correlated to nucleic acid in a particular portioned portion, allowing sequence reads to be correlated back to the partitioned portion from which they came.

Methods of designing sets of bar code sequences is shown for example in Brenner et al. (U.S. Pat. No. 6,235,475), the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides. Since the bar code sequence is sequenced along with the template nucleic acid, the oligonucleotide length should be of minimal length so as to permit the longest read from the template nucleic acid attached. Generally, the bar code sequences are spaced from the template nucleic acid molecule by at least one base (minimizes homopolymeric combinations).

Methods of the invention involve attaching the bar code sequences to the template nucleic acids. In certain embodiments, the bar code sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules.

The ligation may be blunt ended or via use of complementary over hanging ends. In certain embodiments, following fragmentation, the ends of the fragments may be repaired, trimmed (e.g. using an exonuclease), or filled (e.g., using a polymerase and dNTPs), to form blunt ends. Upon generating blunt ends, the ends may be treated with a polymerase and dATP to form a template independent addition to the 3'-end and the 5-end of the fragments, thus producing a single A overhanging. This single A is used to guide ligation of fragments with a single T overhanging from the 5'-end in a method referred to as T-A cloning.

Alternatively, because the possible combination of overhangs left by the restriction enzymes are known after a restriction digestion, the ends may be left as is, i.e., ragged ends. In certain embodiments double stranded oligonucleotides with complementary over hanging ends are used. In particular embodiments, bar code sequences are incorporated using limited cycle PCR.

According to some embodiments of the invention, the templates are sequenced after incorporating bar codes to nucleic acid templates. Various methods can be used to determine the identity of a partition allowing for easier assembly of sequences into larger fragments. In some embodiments, the partitions remain physically separated. In some embodiments, the nucleic acids are labeled with a dye. Appropriate numbers of partitions can be pooled together allowing for the identification of the partition origin of a sequence. The number of partitions that can be pooled together while allowing for the identification of the partition origin of a nucleic acid sequence may depend on the method of labeling the nucleic acids. Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

The obtained sequence reads can be split according to their bar code, i.e., demultiplexed, and reads originating from individual wells can be saved into separate files. Fragments amplified within each partitioned portion can be reconstructed using a de-novo assembly or by aligning to known reference sequence if such sequence exists. Methods of the invention may take advantage of pair-end reads and sequencing quality scores that represent base calling confidence to reconstruct full length fragments.

To begin the reconstruction process, short reads may be stitched together bioinformatically, e.g. by finding overlaps and extending them. To be able to do that unambiguously, one may ensure that long fragments that were amplified within each partitioned portion are distinct enough, and do not have similar stretches of DNA that will make assembly from short fragments ambiguous, which can occur, for example, if two molecules in the same well originated from overlapping positions on homologous chromosomes, overlapping positions of same chromosome, or a genomic repeat. Such fragments can be detected during sequence assembly process by observing multiple possible ways to extend the fragment, one of which containing a sequence specific to an end marker. End markers can be chosen such that an end marker sequence is not frequently found in DNA fragments of a sample that is analyzed. A probabilistic framework utilizing quality scores can be applied to decide whether a possible sequence extension way represents an end maker and thus the end of a fragment.

Overlapping fragments may be computationally discarded since they no longer represent the same initial long molecule. This process allows to treat a population of molecules resulting after amplification as a clonally amplified population of disjoint molecules with no significant overlap or homology, which enables sequencing errors to be corrected to achieve very high consensus accuracy and allows unambiguous reconstruction of long fragments. If overlaps are not discarded, then one can take into consideration that reads may be originating from fragments originating from two homologous chromosomes or overlapping regions of the same chromosome (in case of diploid organism) which makes error correction difficult and ambiguous.

Computational removal of overlapping fragments also allows use of quality scores to resolve nearly-identical repeats. Resulting long fragments may be assembled into full genomes using any of the algorithms known in the art for genome sequence assembly that can utilize long reads.

In addition to de-novo assembly fragments can be used to obtain phasing (assignment to homologous copies of chromosomes) of genomic variants, by observing that under conditions of experiment described in the preferred embodiment long fragments originate from either one of chromosomes, which enables to correlate and co-localize variants detected in overlapping fragments obtained from distinct partitioned portions.

Figure 7:
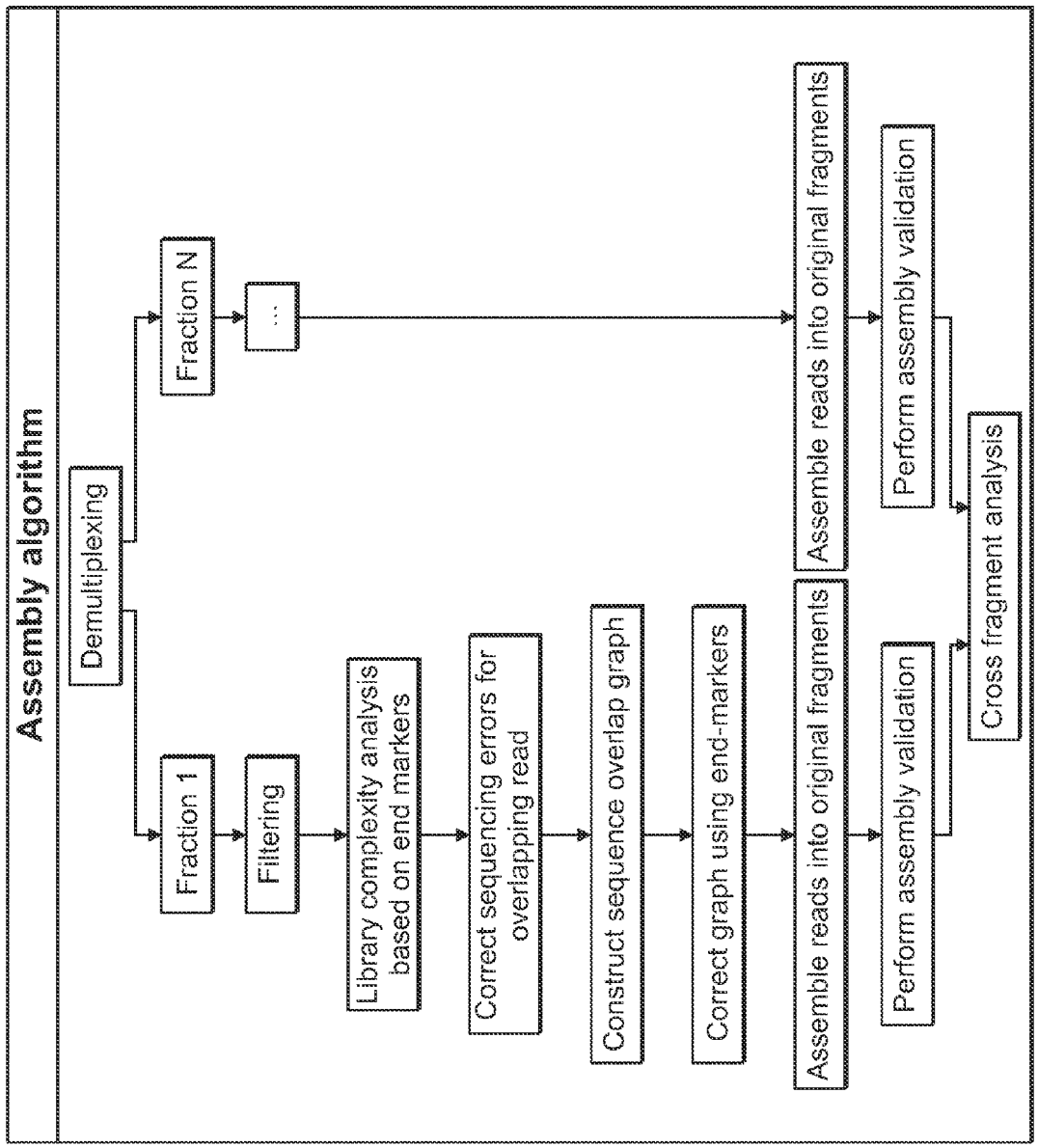
FIG. 7 illustrates an example for a workflow for sequence assembly according to some embodiments of the invention.

FIG. 7 illustrates an example for a workflow for sequence assembly. Accordingly, a demultiplexing step may be applied to separate reads into their fractions of origin, for example, by using the tags/barcodes on the reads. An optional filtering step may filter out or trim reads if they are of too low quality, for example with sequencer quality (Q) values of higher than 15, 12, 10, 8, 6, or 5, are detected as sequencing artifacts, or have a low sequence complexity. A complexity analysis may be optionally incorporated, for example by using end markers to identify reads that originate from the beginning or end of an original fragment. The sequence immediately after the end marker may be used to estimate the number of fragments each fraction contained. Sequencing errors may be corrected for overlapping reads, for example based on the base quality reported by the sequencer for the overlapping reads. A sequence overlap graph may be constructed, for example bye using overlaps between sequences to infer the connectivity and ordering of sequences. The graph may be corrected using the end-markers, by restricting the connection of reads to other reads in a single chosen direction. The reads may be assembled into original fragments, for example by tracing a path along the graph that is consistent with paired reads (if available) to reconstruct the original fragment. Optionally, an assembly validation may be performed. For example, the original reads may be aligned to the assembled fragment, every base along the fragment may be assessed for the presence of supporting reads covering it, and, optionally for the presence of paired reads which map upstream and/or downstream of that base. A cross-fragment analysis may be performed comparing fragments originating from different fractions to detect any possible mis-assemblies.

Methods and systems described herein are equipped to provide sequence information with very high per base accuracies, for example per base accuracies of greater than 80, 90, 95, 99, 99.9, 99.98, 99.99%, 99.999% or higher. The per base accuracies may depend on sequence coverage with underlying short reads, and/or average accuracies for stretches of sequences, for example average accuracies of greater than 80, 90, 95, 99, 99.9, 99.98, 99.99% or higher may be achieved. Sequencing errors affecting per base and average accuracy of sequence information due to underlying sequencing platform may be substantially or completely corrected by majority calls by the assembly methods and systems described herein, such as a computer acting as an assembler. An output with a single long read may be produced from putting together multiple long reads.

Further, methods and systems described herein may allow for increased assembly accuracy; one contributing factor being higher read accuracies allowing for resolution of nearly identical repeats and thus preventing incorrect read assemblies. Genome assembly based on the longer and more accurate reads/sequences described herein would result in higher assembly accuracies compared to traditional genomic reads known in the art. For example, methods and systems of the invention can achieve average assembly accuracies of greater than 90, 95, 99, 99.9, 99.98, 99.99%, or higher.

Further yet, methods and systems described herein may allow for increased genome resequencing accuracies. In various embodiments, hypermapping, phase resolved sequencing, and/or local reassembly is made possible due to reduced sample complexity and multiple short reads covering the sequence reads described herein. In some embodiments, hypermapping may be utilized allowing to cover larger fractions of the genome, for example identical repeats and copy number variations spanned by a common sequence which cannot be uniquely covered with short reads that map equally well to multiple genomic locations.

Figure 8:
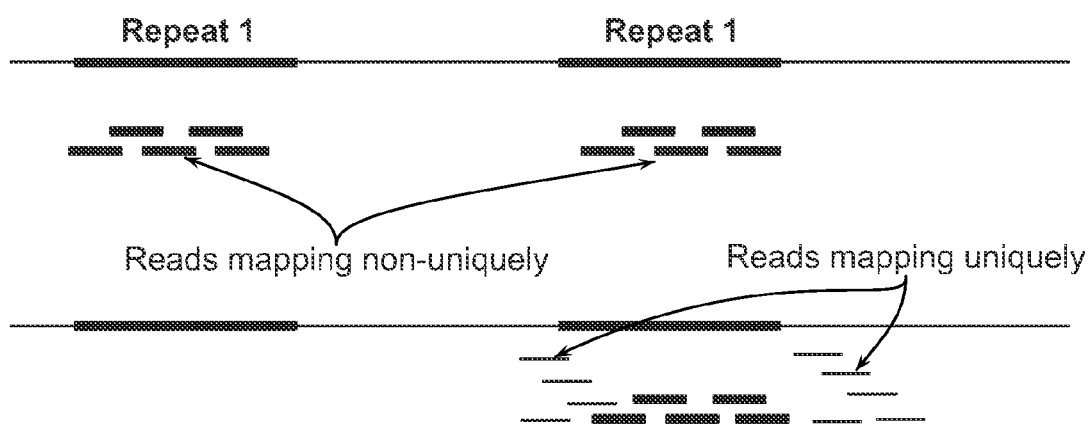
FIG. 8 illustrates application of hypermapping according to some embodiments of the invention.

FIG. 8 illustrates application of hypermapping according to some embodiments of the invention. Hypermapping may be applied to genome resequencing, phasing, cancer analysis, and any other suitable sequencing methods known in the art. Typically, a genome may contain many sequence repeats, some of which are identical or nearly identical. Accordingly, short reads originating from these repeat regions may have multiple equally confident alignments to a reference genome, therefore making it extremely hard to establish which exact copy of the repeat they originated from. Most genome analysis pipelines known in the art place these reads randomly in an effort to preserve coverage depth.

Methods and systems described herein may allow for short reads to originate from a reduced representation of a genome, for example a set of amplifiable fragments in a given fraction. Proper mapping of reads that originate from repeat regions may be achieved by selecting a repeat locus such the repeat locus is spanned by uniquely mapped reads, consistent with the amplifiable fragment originating from that region.

According to various embodiments of the invention, hypermapping effectively reduces the complexity of the genome by only considering parts of the genome that are covered by amplifiable fragments, for example the amplifiable fragments within a specific sample volume/fraction. Accordingly, a much higher fraction of the genome may be accessible to mapping, and incorrect read mappings may be reduced, thereby improving resequencing accuracy.

Methods and systems described herein allow for genome phasing based on reduced genome representation strategies. Each sample volume/fraction may contain a reduced subset of the genome organized as continuous regions of the genome. In various embodiments, each of the sequences originating from a region/fragment within a sample volume/fraction can be deduced to have originated from a single chromosome and thus will only contain variants present on that chromosome. Accordingly, it is possible to reconstruct local chromosome phasing, for example by finding overlapping fragments that share heterozygous variants. Gaps, for example those resulting from a long stretch of homozygous variants, can be covered, for example by using HapMap data and Linkage Disequilibrium.

Various embodiments of the invention utilize cloud based phasing (see for example Shedure et al. Nat Biotechnol. 2011 January; 29(1):59-63). Alternatively. external data, for example data from the 1000 Genomes Project, may be utilized to phase regions relative to each other, for example based on a concept of "Linkage Disequilibrium". Without being bound by theory, DNA is typically passed to offspring in large blocks that are mixture of blocks derived from parents. Accordingly, a few blocks in previously fully phased individuals, for example by trio sequencing or any other suitable method known in the art, may be utilized for finding overlaps with locally phased blocks described herein and proper phasing can be inferred.

Figure 9:
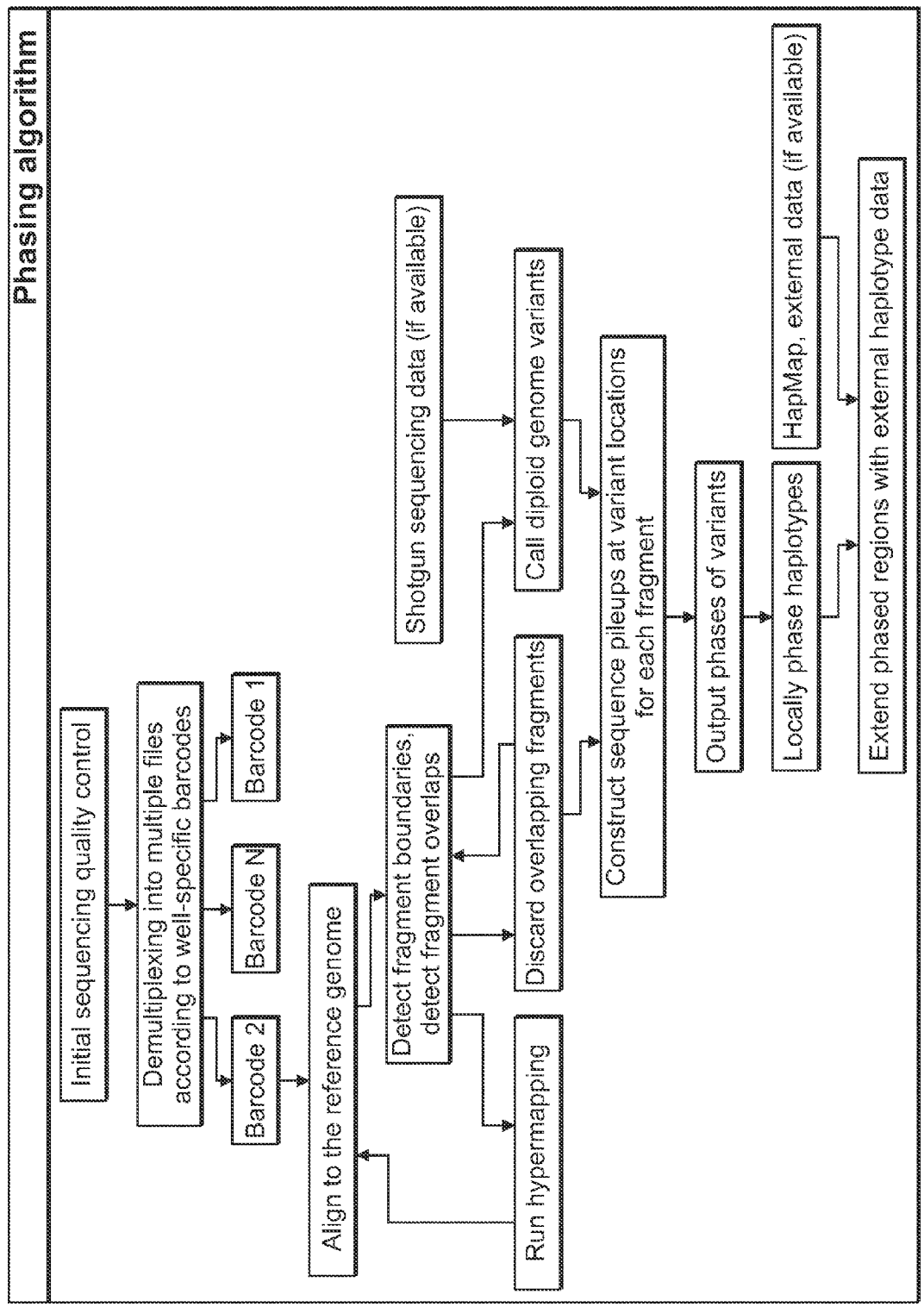
FIG. 9 illustrates an exemplary embodiment comprising a phasing algorithm.

FIG. 9 illustrates an exemplary embodiment comprising a phasing algorithm. Accordingly, an initial sequencing quality control round can be followed by demultiplexing the sequencing results into multiple data depositories, such as files, databases, tables, or any other suitable data storage system known in the art. The demultiplexing can be guided by the barcodes that identify the origin of a sequence read, such as a partition. The demultiplexed information can then be analyzed individually from here on.

The demultiplexed sequence information can be aligned to a reference genome and fragment boundaries and/or overlaps can be detected. A hypermapping algorithm may improve the alignment of the correct reads to the correct parts of the genome. The fragment boundaries and overlaps can be updated accordingly.

Overlapping fragments, such as those that originated from a single partition with two target polynucleotide comprising overlapping sequence segments above a certain length (e.g. over 20, 30, 40, 50, 60, 70, 80, 90, 100 or more bp) may be discarded from the data and a new analysis round may be employed comprising one or more of the detection of fragment boundaries and/or overlaps, hypermapping, and alignment to a reference genome steps.

The detection of fragment boundaries and overlaps may allow for calling diploid genome variants. Auxiliary information, such as shotgun sequencing data, may be incorporated in the genome variant analysis.

Sequence information related to each fragment can be accumulated at all or selected positions, for example at variant positions. Phasing information for variants can be determined and output. Haplotypes can be locally phased. In addition, external data, such as from HapMap, may be combined with local phasing information, for example phasing information covering a range of less than 100, 200, 300, 400, 500, 600, 700, 800, 900, 1000, 1500, 2000, 3000, 4000, or 5000 bp, extending phased regions with external haplotype data over a range of more than 1, 2, 3, 4, 5, 6, 7, 8, 9, 10, 15, 20, 25, 30, 40, 50, 100 kb or more.

Various embodiments of the invention allow for detection of structural variants, for example using standard suitable methods known in the art. Accordingly, relying on the reduced representation methods described herein may reduce noise and increase accuracy of SV detection.

According to various embodiments of the invention, only a fraction of the genome is amplified in each reaction volume/fraction/partition, resulting in fewer repeats interfering with a local reassembly process. Accordingly, parts of the genome that are substantially different from a reference can be locally reconstructed for example by de-novo, reference assisted assembly or using algorithms based on paired end information.

Multiple sample fractions each with a reduced genome representation of a genome, in various embodiments, allows for new kinds of algorithms to be employed. For example, it is possible to resolve some repeats, finding a correct assembly across repeat regions by establishing whether regions spanning the repeat are in proximity to each other.

Figure 10:
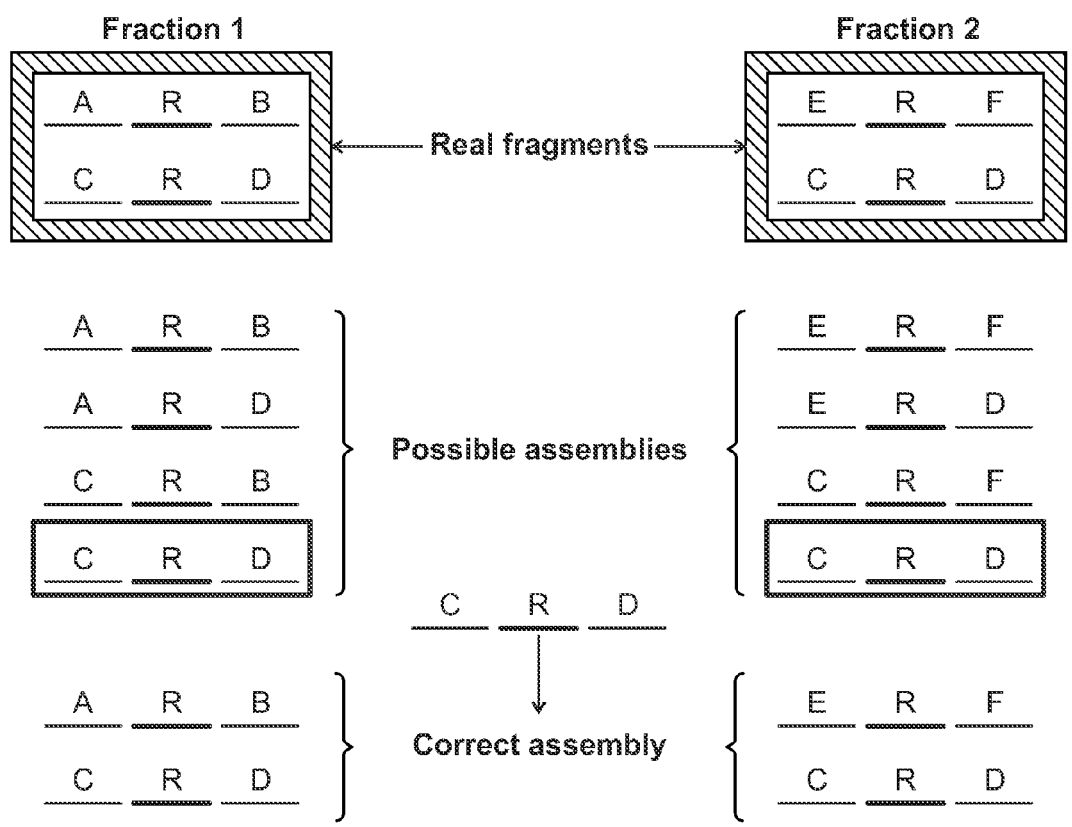
FIG. 10 illustrates an example method for Poor Man's Mate Pair (PMMP) according to some embodiments of the invention.

FIG. 10 illustrates an example method for Poor Man's Mate Pair (PMMP). Two fractions have fragments that contain an identical repeat (R). Within each well, an unambiguous assembly is not possible because two different assemblies would be equally supported by the short reads (ARB and CRD in Fraction 1, and ERF and CRD in Fraction 2). However, by noticing that CRD is found in Fraction 1, and also in Fraction 2, and that neither of sequences "A" or "B" is found in Fraction 2, it can be reasoned that sequences C and D are found in close proximity to each other and thus CRD is the right assembly. Therefore, one can also reconstruct "ARB" and "ERF" assemblies in Fractions 1 and 2. This is a significant improvement over samples with larger or full genome representations. Accordingly, additional information may be obtained by having multiple wells with reduced representations as described herein.

Methods

De-novo Assembly

Complex and repetitive regions of genomes are especially hard to assemble across to generate long sequences. The low accuracy in this process makes it especially hard to differentiate between very similar repeats. In addition, this process is computationally expensive and in some cases not practical.

The long reads obtained using the methods and systems described herein provide long enough sequences to bridge across most known repetitive elements, thus making it possible to assemble very long contigs without breaking at repeat regions. The high accuracy of reads described herein similar repetitive regions can be distinguished avoiding mis-assembly. For example, nearly identical genomic repeat regions with 10, 9, 8, 7, 6, 5, 4, 3, 2, or 1 variations in their sequence can be distinguished using the methods and systems described herein. In some embodiments, the methods described herein can discriminate and quantitate genomic DNA regions. The methods described herein can discriminate and quantitate at least 1; 2; 3; 4; 5; 10, 20; 50; 100; 200; 500; 1,000; 2,000; 5,000; 10,000, 20,000; 50,000; 100,000; 200,000; 300,000; 400,000; 500,000; 600,000; 700,000; 800,000; 900,000; 1,000,000; 2,000,000 or 3,000,000 different genomic DNA regions. The methods described herein can discriminate and quantitate genomic DNA regions varying by 1 nt or more than 1, 2, 3, 5, 10, 15, 20, 21, 22, 24, 25, 30, 40, 50, 60, 70, 80, 90, 100, 200, 300, 400 or 500 nt. Further, the computation requirements, for example memory, CPU runtime of the de-novo assembly from very long reads are much lower than those of, for example, shotgun assembly.

The use of the single-molecule sequencing technologies described herein allows for obtaining reads to originating from a single haplotype. Taken together with the extremely low error rate and long read span phasing of polyploid genomes may be facilitated, allowing for phased de-novo assembly.

The methods and systems described herein facilitate the use of reduced representations of a genome in each individual volume thus decreasing "sample complexity", for example by 10, 100, 1000, 10000, 100000 fold or more, relative to the full genome.

The assembly and post-assembly analysis of reads or clouds using the methods and systems described herein may be enhanced in conjunction with other sequencing technologies known in the art, such as shotgun sequencing, paired-end sequencing or mate-pair sequencing.

In some cases, the methods described herein are used to detect and/or quantify genomic DNA regions such as a region containing a DNA polymorphism. A polymorphism refers to the occurrence of two or more genetically determined alternative sequences or alleles in a population. A polymorphic marker or site is the locus at which divergence occurs. Preferred markers have at least two alleles, each occurring at a frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include single nucleotide polymorphisms (SNP's), restriction fragment length polymorphisms (RFLP's), short tandem repeats (STRs), variable number of tandem repeats (VNTR's), hypervariable regions, minisatellites, dinucleotide repeats, trinucleotide repeats, tetranucleotide repeats, simple sequence repeats, and insertion elements such as Alu. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

Methods and systems described herein can be used to discriminate and quantitate a DNA region containing a DNA polymorphism. The methods described herein can discriminate and quantitate at least 1, 2, 3, 4, 5, 10, 20, 50, 100, 200, 500, 1,000, 2,000, 5,000, 10,000, 20,000, 50,000, 100,000, 200,000, 300,000, 400,000, 500,000, 600,000, 700,000, 800,000, 900,000, 1,000,000, 2,000,000, 3,000,000 or more DNA polymorphisms originating from one or more samples. In some embodiments, the methods described herein can discriminate and quantitate at least 1, 2, 3, 4, 5, 10, 20, 50, 100, 200, 500, 1,000, 2,000, 5,000, 10,000, 20,000, 50,000, 100,000, 200,000, 300,000, 400,000, 500,000, 600,000, 700,000, 800,000, 900,000, 1,000,000, 2,000,000, 3,000,000, or more different polymorphic markers originating form one or more samples. In some embodiments, the methods described herein can discriminate and quantitate at least 1, 2, 3, 4, 5, 10, 20, 50, 100, 200, 500, 1,000, 2,000, 5,000, 10,000, 20,000, 50,000, 100,000, 200,000, 300,000, 400,000, 500,000, 600,000, 700,000, 800,000, 900,000, 1,000,000, 2,000,000, 3,000,000, or more different SNPs originating from one or more samples.

In some embodiments, the methods described herein are used to detect and/or quantify genomic DNA regions by mapping the region to the genome of a species in the case where the transplant donor and the transplant recipient are not from the same species (e.g., xenotransplants). In some embodiments, the methods described herein can discriminate and quantitate a DNA region from a species. The methods described herein can discriminate and quantitate of at least 1, 2, 3, 4, 5, 10, 20, 50, 100, 200, 500, 1,000, 2,000, 5,000, 10,000, 20,000, 50,000, 100,000, 200,000, 300,000, 400,000, 500,000, 600,000, 700,000, 800,000, 900,000, 1,000,000, 2,000,000, 3,000,000, or more DNA regions from a species.

Methods and systems described herein may comprise the detection of genetic variants. In some instances, at least about 2, at least about 3, at least about 4, at least about 5, at least about 10, at least about 15, at least about 20, at least about 30, at least about 40, at least about 50, at least about 100, at least about 200, at least about 300, at least about 400, at least about 500, at least about 600, at least about 700, at least about 800, at least about 900, or at least about 1000 genetic variants are detected in a single reaction. In another example, at least about 2000, at least about 5000, at least about 10000, at least about 15000, at least about 20000, at least about 30000, at least about 40000, at least about 50000, at least about 100000, at least about 200000, at least about 300000, at least about 400000, at least about 500000, at least about 600000, at least about 700000, at least about 800000, at least about 900000, or at least about 1000000 genetic variants are detected in a single reaction. De novo assembly comprising an N50 value or median of 50, 75, 100, 200, 300, 400, 500, 600, 700, 800, 900, 1000 kilobases or more can be achieved using the methods and systems described herein. Genetic variants within these assembled sequences can be identified according to the methods of the invention.

Genome Phasing

Phasing across continuous regions of sequences is greatly facilitated by longer read lengths. Many sequencing based technologies known in the art lack read length to phase across continuous regions, such as regions longer than 200, 300, 400, 500, 700, 1000, 2000, 3000, or more nucleotides. Computational approaches may prove inaccurate and unable to phase low frequency variants, which were not measured across reference populations. In addition, phasing based on trio sequencing, for example including an individual and parents, can be expensive and impractical, requiring access to parents' DNA and cannot reliably establish phasing in locations heterozygous in both parents and a child.

In contrast, methods and systems described herein facilitate generation of long sequences originating from single molecule amplification and spanning across multiple heterozygous sites. Thus, shorter sequence reads, for example reads less than 20, 25, 30, 40, 50, 100, 200, or 300 can be utilized and assembled into longer sequences. Accurate phasing of long sequences by the methods and systems described herein may increase variant calling accuracy, for example by using haploid error models. Further, methods and systems described herein allow for the phasing of low frequency variants not present in reference SNP chips.

In particular embodiments, phasing is done by aliquoting an intermediate amount of amplifiable fragments, for example exponentially amplifiable fragments, in each partition, for example between about 1-10 MB and about 100-200 MB or more, and sequencing them to an intermediate coverage of 2-5 fold. Fragment boundaries can be detected by detecting reads grouping at the specific parts of the genome, and overlapping fragments within a partition can be discarded with the use of the end marker sequence. Unphased SNPs can be identified from alignments of read clouds that are produced by fragments or using standard whole genome sequencing. For each fragment, variants that are supported by reads that originated from this variant can be recorded. This capability is largely supported by the very high probability (>90%, >99%, >99.9%, or higher, depending on the number of amplifiable fragments per partition) that clouds would originate from a single haplotype, that variant phases are mostly consistent within a cloud, and that a probabilistic model, such as Hidden Markov Model can be used to establish the most likely sequence of variant phases across a region on the chromosome. Accordingly, disjoint phased segments of various lengths can be generated, typically up to about 100, 200, 300, 400, or 500 kb, but in some cases as long as multiple megabases in regions with significant cloud coverage and abundance of heterozygous variants. Relative phasing of these locally phased blocks can be established using statistical inference using population phased data, such as HapMap or 1000 genomes project data, and/or statistical model based algorithms, for example implementing a hidden Markov model for establishing most likely relative phasing of locally phased variant blocks. Examples of statistical phasing are well known in the art, including the use of "IMPUTE" (HOWIE, et al. A Flexible and Accurate Genotype Imputation Method for the Next Generation of Genome-Wide Association Studies. PLoS Genet. 2009 June; 5(6):e1000529.) or "BEAGLE" (BROWNING, et al. Rapid and Accurate Haplotype Phasing and Missing-Data Inference for Whole-Genome Association Studies By Use of Localized Haplotype Clustering. Am J Hum Genet. 2007 November; 81(5):1084-97.) software. Statistical phasing is based on the phenomenon of linkage disequilibrium resulting from genomic variants being inherited in large blocks including thousands of variants. Other embodiments include combining phasing approaches described herein with raw whole genome sequencing data, paired end data, or sequencing information from a close relative to establish accurate whole genome variant phasing. Hypermaping can be employed to increase fragment mapping accuracy. Phased genome blocks can be used to establish which variants are collocated on the one of the two chromosomes, whether both copies of a gene are affected by a mutation, or for any other suitable uses known in the art.

Cancer Genome Sequencing

High degrees of accuracy required by cancer genome sequencing can be achieved using the methods and systems described herein. Typically, inaccurate reference genomes make basecalling challenges when sequencing cancer genomes. Heterogeneous samples and small starting materials, for example a sample obtained by biopsy introduce additional challenges. Further, detection of large scale structural variants and/or losses of heterozygosity is often crucial for cancer genome sequencing, as well as the ability to differentiate between somatic variants and errors in basecalling.

Systems and methods described herein may generate accurate long sequences from complex samples containing 2, 3, 4, 5, 6, 7, 8, 9, 10, 12, 15, 20 or more varying genomes. Mixed samples of normal, benign, and/or tumor origin may be analyzed, optionally without the need for a normal control. In some embodiments, starting samples as little as 100 ng or even as little as hundreds of genome equivalents are utilized to generate accurate long sequences. Systems and methods described herein may allow for detection of large scale structural variants and rearrangements, Phased variant calls may be obtained over long sequences spanning 50, 100, 200, 300, 400, 500, 600, 700, 1000, 1500, 2000, 2500, 3000, 4000, 5000, 10000, or more nucleotides.

Figure 11:
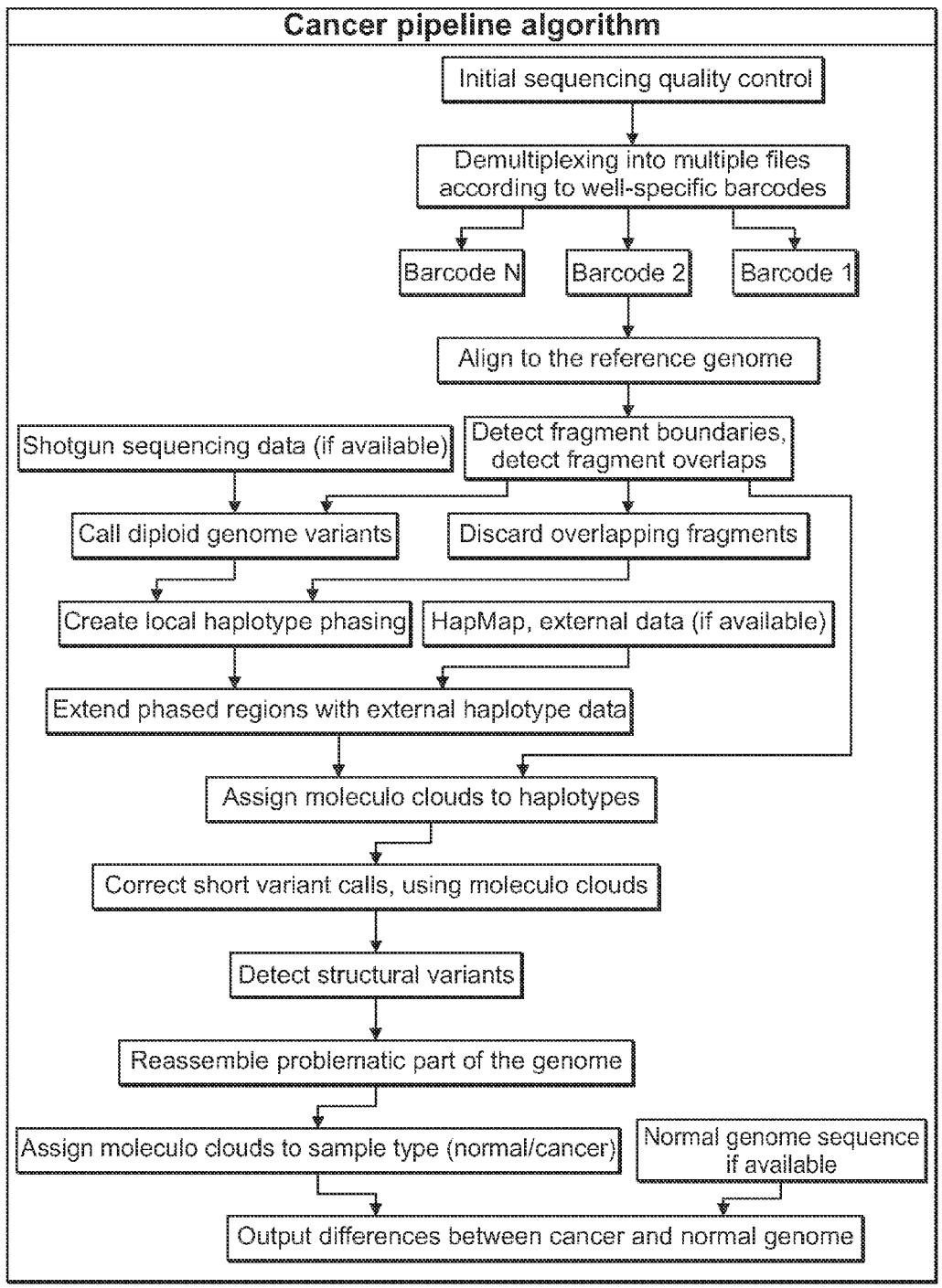
FIG. 11 illustrates an exemplary embodiment comprising an algorithm for cancer detection according to some embodiments of the invention.

FIG. 11 illustrates an exemplary embodiment comprising an algorithm for cancer detection. Accordingly, an initial sequencing quality control round can be followed by demultiplexing the sequencing results into multiple data depositories, such as files, databases, tables, or any other suitable data storage system known in the art. The demultiplexing can be guided by the barcodes that identify the origin of a sequence read, such as a partition. The demultiplexed information can then be analyzed individually from here on.

The demultiplexed sequence information can be aligned to a reference genome and fragment boundaries and/or overlaps can be detected.

Overlapping fragments, such as those that originated from a single partition with two target polynucleotide comprising overlapping sequence segments above a certain length (e.g. over 20, 30, 40, 50, 60, 70, 80, 90, 100 or more bp) may be discarded from the data.

The detection of fragment boundaries and overlaps may allow for calling diploid genome variants. Auxiliary information, such as shotgun sequencing data, may be incorporated in the genome variant analysis. Haplotypes can be locally phased using the genome variant calls. In addition, external data, such as from HapMap, may be combined with local phasing information, for example phasing information covering a range of less than 100, 200, 300, 400, 500, 600, 700, 800, 900, 1000, 1500, 2000, 3000, 4000, or 5000 bp, extending phased regions with external haplotype data over a range of more than 1, 2, 3, 4, 5, 6, 7, 8, 9, 10, 15, 20, 25, 30, 40, 50, 100 kb or more.

Haplotypes determined using the methods and systems described herein may be assigned to computational resources, for example computational resources over a network, such as a cloud system. Short variant calls can be corrected, if necessary, using relevant information that is stored in the computational resources. Structural variants can be detected based on the combined information from short variant calls and the information stored in the computational resources. Problematic parts of the genome, such as those with repeat regions, low sequence accuracy, high variant rates, ALU repeats, segmental duplications, or any other relevant problematic parts known in the art, can be reassembled for increased accuracy.

A sample type can be assigned to the sequence information either locally or in a networked computational resource, such as a cloud. In cases where the source of the information is known, for example when the source of the information is from a cancer or normal tissue, the source can be assigned to the sample as part of a sample type. Other sample type examples generally include, but are not limited to, tissue type, sample collection method, presence of infection, type of infection, processing method, size of the sample, etc. In cases where a complete or partial comparison genome sequence is available, such as a normal genome in comparison to a cancer genome, the differences between the sample data and the comparison genome sequence can be determined and optionally output.

Metagenomics

Methods and systems described herein are well suited to analyze complex samples with large variations of metagenomic representations. Typically, low frequency genomes are hard to assemble, requiring high computational cost due to need to assemble whole sample. Methods and systems described herein, allow for complexity reduction facilitating the analysis of samples comprising more than 1, 2, 3, 4, 5, 6, 7, 8, 9, 10, 20, 30, 40, 50, 100, 200, 300, 400, 500, 1000 or more metagenomic representations. A few, for example about 100-1000 amplifiable molecules can be selected out of the whole pool of DNA, amplified in separated partitions, barcoded, sequenced, and/or analyzed in a partition-specific manner thus reducing computational complexity of the analysis by providing less complex sample within each well. Ability to assemble artificially limited amount of amplifiable sequences together allows for better annotation of DNA samples present in the initial population, because queries against genome databases such as "nt" return results with higher significance as query gets longer. Therefore search sensitivity can be improved using long reads generated by the methods and systems described herein, as compared to shorter reads, such as shotgun short reads.

RNA Sequencing

A significant amount of information may be obtained from long-range dependencies between exons in RNA sequences. Methods and systems described herein may generate long reads of RNA that span across multiple exons. Thus, transcripts of 100, 200, 300, 400, 500, 750, 1000, 1500, 2000, 2500, 3000, or more nucleotides may be reconstructed de-novo using the methods and systems described herein.

In some embodiments, RNA sequences may be mapped against a reference transcriptome. The mapping may optionally require less coverage than de-novo assembling the transcript, which in turn allows for the detection of less abundant transcripts. Methods and systems of the invention may allow for transcripts that are represented at less than a 1000, 900, 800, 700, 600, 500, 400, 300, 200, 100, 50, 40, 30, 20, 10, 9, 8, 7, 6, 5, 4, 3, or 2 copies in a sample. In some cases, the methods described herein are used to detect and/or quantify gene expression. In some embodiments, the methods described herein provide high discriminative and quantitative analysis of multiples transcripts. The methods described herein can discriminate and quantitate the expression of at least 1, 2, 3, 4, 5, 10, 20, 50, 100, 200, 500, 1,000, 2,000, 5,000, 10,000, 20,000, 50,000, 100,000, different target nucleic acids, for example mRNA or cDNA. In some embodiments, the methods described herein are used to detect and/or quantify gene expression of genes with similar sequences. The methods described herein can discriminate and quantitate the expression of transcripts varying by 1 nt or more than 1, 2, 3, 5, 10, 15, 20, 21, 22, 24, 25, 30, 40, 50, 60, 70, 80, 90, 100, 200, 300, 400 or 500 nt in a target nucleic acid, for example mRNA or cDNA.

Multiplexing

In some instances, the foreign molecules are detected in a multiplexed reaction. For example, at least about 2, at least about 3, at least about 4, at least about 5, at least about 10, at least about 15, at least about 20, at least about 30, at least about 40, at least about 50, at least about 100, at least about 200, at least about 300, at least about 400, at least about 500, at least about 600, at least about 700, at least about 800, at least about 900, or at least about 1000 molecules are detected in a single reaction or a single reaction container. In another example, at least about 2000, at least about 5000, at least about 10000, at least about 15000, at least about 20000, at least about 30000, at least about 40000, at least about 50000, at least about 100000, at least about 200000, at least about 300000, at least about 400000, at least about 500000, at least about 600000, at least about 700000, at least about 800000, at least about 900000, or at least about 1000000 molecules are detected in a single reaction or a single reaction container.

Applications

The methods of the present invention can be used in the analysis of genetic information of selective genomic regions of interest as well as genomic regions which may interact with the selective region of interest. Amplification methods as disclosed herein can be used in the devices, kits, and methods known to the art for genetic analysis, such as, but not limited to those found in U.S. Pat. Nos. 6,449,562, 6,287,766, 7,361,468, 7,414,117, 6,225,109, and 6,110,709.

In some cases, amplification methods of the present invention can be used to amplify target nucleic acid for DNA hybridization studies to determine the presence or absence of polymorphisms. The polymorphisms, or alleles, can be associated with diseases or conditions such as genetic disease. In other cases the polymorphisms can be associated with susceptibility to diseases or conditions, for example, polymorphisms associated with addiction, degenerative and age related conditions, cancer, and the like. In other cases, the polymorphisms can be associated with beneficial traits such as increased coronary health, or resistance to diseases such as HIV or malaria, or resistance to degenerative diseases such as osteoporosis, Alzheimer's or dementia.

The compositions and methods of the invention can be used for diagnostic, prognostic, therapeutic, patient stratification, drug development, treatment selection, and screening purposes. The present invention provides the advantage that many different target molecules can be analyzed at one time from a single biomolecular sample using the methods of the invention. This allows, for example, for several diagnostic tests to be performed on one sample.

The composition and methods of the invention can be used in genomics. The methods described herein will typically provide an answer rapidly which is very desirable for this application. The methods and composition described herein can be used in the process of finding biomarkers that may be used for diagnostics or prognostics and as indicators of health and disease. The methods and composition described herein can be used to screen for drugs, e.g., drug development, selection of treatment, determination of treatment efficacy and/or identify targets for pharmaceutical development. The ability to test gene expression on screening assays involving drugs is very important because proteins are the final gene product in the body. In some embodiments, the methods and compositions described herein will measure both protein and gene expression simultaneously which will provide the most information regarding the particular screening being performed.

The composition and methods of the invention can be used in gene expression analysis. The methods described herein discriminate between nucleotide sequences. The difference between the target nucleotide sequences can be, for example, a single nucleic acid base difference, a nucleic acid deletion, a nucleic acid insertion, or rearrangement. Such sequence differences involving more than one base can also be detected. The process of the present invention is able to detect infectious diseases, genetic diseases, and cancer. It is also useful in environmental monitoring, forensics, and food science. Examples of genetic analyses that can be performed on nucleic acids include e.g., SNP detection, STR detection, RNA expression analysis, promoter methylation, gene expression, virus detection, viral subtyping and drug resistance.

The present methods can be applied to the analysis of biomolecular samples obtained or derived from a patient so as to determine whether a diseased cell type is present in the sample, the stage of the disease, the prognosis for the patient, the ability to the patient to respond to a particular treatment, or the best treatment for the patient. The present methods can also be applied to identify biomarkers for a particular disease.

In some embodiments, the methods described herein are used in the diagnosis of a condition. As used herein the term "diagnose" or "diagnosis" of a condition includes predicting or diagnosing the condition, determining predisposition to the condition, monitoring treatment of the condition, diagnosing a therapeutic response of the disease, and prognosis of the condition, condition progression, and response to particular treatment of the condition. For example, a blood sample can be assayed according to any of the methods described herein to determine the presence and/or quantity of markers of a disease or malignant cell type in the sample, thereby diagnosing or staging the a disease or a cancer.

In some embodiments, the methods and composition described herein are used for the diagnosis and prognosis of a condition.

Numerous immunologic, proliferative and malignant diseases and disorders are especially amenable to the methods described herein. Immunologic diseases and disorders include allergic diseases and disorders, disorders of immune function, and autoimmune diseases and conditions. Allergic diseases and disorders include but are not limited to allergic rhinitis, allergic conjunctivitis, allergic asthma, atopic eczema, atopic dermatitis, and food allergy. Immunodeficiencies include but are not limited to severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects. Autoimmune and immune dysregulation disorders include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens.

Proliferative diseases and disorders that may be evaluated by the methods of the invention include, but are not limited to, hemangiomatosis in newborns; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Malignant diseases and disorders that may be evaluated by the methods of the invention include both hematologic malignancies and solid tumors.

Hematologic malignancies are especially amenable to the methods of the invention when the sample is a blood sample, because such malignancies involve changes in blood-borne cells. Such malignancies include non-Hodgkin's lymphoma, Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders.

Plasma cell disorders that may be evaluated by the methods of the invention include multiple myeloma, amyloidosis and Waldenstrom's macroglobulinemia.

Example of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

The methods described herein can be used to diagnose pathogen infections, for example infections by intracellular bacteria and viruses, by determining the presence and/or quantity of markers of bacterium or virus, respectively, in the sample.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia, B-Hemolytic strep., Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Fungal infectious agents which can be detected by the present invention include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidum, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii*, and *Necator americanis*.

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention Thus, the target molecules detected using the compositions and methods of the invention can be either patient markers (such as a cancer marker) or markers of infection with a foreign agent, such as bacterial or viral markers.

The compositions and methods of the invention can be used to identify and/or quantify a target molecule whose abundance is indicative of a biological state or disease condition, for example, blood markers that are upregulated or downregulated as a result of a disease state.

In some embodiments, the methods and compositions of the present invention can be used for cytokine expression. The low sensitivity of the methods described herein would be helpful for early detection of cytokines, e.g., as biomarkers of a condition, diagnosis or prognosis of a disease such as cancer, and the identification of subclinical conditions.

Sample

The different samples from which the target polynucleotides are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, or organ sample derived therefrom, including, for example, cultured cell lines, biopsy, blood sample, or fluid sample containing a cell. The subject may be an animal, including but not limited to, an animal such as a cow, a pig, a mouse, a rat, a chicken, a cat, a dog, etc., and is usually a mammal, such as a human. Samples can also be artificially derived, such as by chemical synthesis. In some embodiments, the samples comprise DNA. In some embodiments, the samples comprise genomic DNA. In some embodiments, the samples comprise mitochondrial DNA, chloroplast DNA, plasmid DNA, bacterial artificial chromosomes, yeast artificial chromosomes, oligonucleotide tags, or combinations thereof. In some embodiments, the samples comprise DNA generated by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic isolation step, purification of nucleic acids can be performed after any step in the methods of the invention, such as to remove excess or unwanted reagents, reactants, or products.

In some embodiments, sample polynucleotides are fragmented into a population of fragmented DNA molecules of one or more specific size range(s). In some embodiments, fragments are generated from at least about 1, 10, 100, 1000, 10000, 100000, 300000, 500000, or more genome-equivalents of starting DNA. Fragmentation may be accomplished by methods known in the art, including chemical, enzymatic, and mechanical fragmentation. In some embodiments, the fragments have an average length from about 10 to about 10,000, 20,000, 30,000, 40,000, 50,000 or more nucleotides. In some embodiments, the fragments have an average length from about 50 to about 2,000 nucleotides. In some embodiments, the fragments have an average length from about 100-50,000, 200-2,500, 10-1,000, 10-800, 10-500, 50-500, 50-250, 50-150 nucleotides, or any range bounded by any of these values (e.g. about 200-500). In some embodiments, the fragments have an average length less than 500 nucleotides, such as less than 400 nucleotides, less than 300 nucleotides, less than 200 nucleotides, or less than 150 nucleotides. In some embodiments, the fragmentation is accomplished mechanically comprising subjection sample polynucleotides to acoustic sonication. In some embodiments, the fragmentation comprises treating the sample polynucleotides with one or more enzymes under conditions suitable for the one or more enzymes to generate double-stranded nucleic acid breaks. Examples of enzymes useful in the generation of polynucleotide fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of $Mg^{++}$ and in the presence of $Mn^{++}$. In some embodiments, fragmentation comprises treating the sample polynucleotides with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence. In some embodiments, the method includes the step of size selecting the fragments via standard methods such as column purification or isolation from an agarose gel.

In some embodiments, the 5' and/or 3' end nucleotide sequences of fragmented DNA are not modified prior to ligation with one or more adapter oligonucleotides. For example, fragmentation by a restriction endonuclease can be used to leave a predictable overhang, followed by ligation with one or more adapter oligonucleotides comprising an overhang complementary to the predictable overhang on a DNA fragment. In another example, cleavage by an enzyme that leaves a predictable blunt end can be followed by ligation of blunt-ended DNA fragments to adapter oligonucleotides comprising a blunt end. In some embodiments, the fragmented DNA molecules are blunt-end polished (or "end repaired") to produce DNA fragments having blunt ends, prior to being joined to adapters. The blunt-end polishing step may be accomplished by incubation with a suitable enzyme, such as a DNA polymerase that has both 3' to 5' exonuclease activity and 5' to 3' polymerase activity, for example T4 polymerase. In some embodiments, end repair is followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. DNA fragments having an overhang can be joined to one or more adapter oligonucleotides having a complementary overhang, such as in a ligation reaction. For example, a single adenine can be added to the 3' ends of end repaired DNA fragments using a template independent polymerase, followed by ligation to one or more adapters each having a thymine at a 3' end. In some embodiments, adapter oligonucleotides can be joined to blunt end double-stranded DNA fragment molecules which have been modified by extension of the 3' end with one or more nucleotides followed by 5' phosphorylation. In some cases, extension of the 3' end may be performed with a polymerase such as for example Klenow polymerase or any of the suitable polymerases provided herein, or by use of a terminal deoxynucleotide transferase, in the presence of one or more dNTPs in a suitable buffer containing magnesium. In some embodiments, target polynucleotides having blunt ends are joined to one or more adapters comprising a blunt end. Phosphorylation of 5' ends of DNA fragment molecules may be performed for example with T4 polynucleotide kinase in a suitable buffer containing ATP and magnesium. The fragmented DNA molecules may optionally be treated to dephosphorylate 5' ends or 3' ends, for example, by using enzymes known in the art, such as phosphatases.

In some embodiments, each of the plurality of independent samples comprises at least about 1 pg, 10 pg, 100 pg, 1 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, or more of nucleic acid material. In some embodiments, each of the plurality of independent samples comprises less than about 1 pg, 10 pg, 100 pg, 1 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, or more of nucleic acid.

Kits

Any of the compositions described herein may be comprised in a kit. In a non-limiting example the kit, in suitable container means, comprises: equipment and reagents for DNA fragmentation, an end repair enzyme, adapter ligation enzymes, DNA adapter oligonucleotides, equipment and/or reagents for size selection, and/or qPCR standards. In another non-limiting example the kit, in suitable container means, comprises PCR enzymes and plastics. In a yet further non-limiting example the kit, in suitable container means, comprises a holey plate with fragmentation enzyme, a plate, for example an elution plate, with barcoding oligos, and/or a plate, for example an elution plate, optionally preloaded with PCR enzyme.

The kit can further contain enzymes and/or reagents useful for ligation, cleavage and or amplification. The kit can contain a DNA-polymerase. The kit can contain reagents for amplification. The kit can further optionally contain reagents for sequencing, for example, reagents useful for next-generation massively parallel sequencing methods.

The containers of the kits can generally include at least one vial, test tube, flask, bottle, syringe or other containers, into which a component may be placed, and preferably, suitably aliquoted. Where there is more than one component in the kit, the kit also can generally contain a second, third or other additional container into which the additional components can be separately placed. However, various combinations of components can be comprised in a container.

When the components of the kit are provided in one or more liquid solutions, the liquid solution can be an aqueous solution. However, the components of the kit can be provided as dried powder(s). When reagents and/or components are provided as a dry powder, the powder can be reconstituted by the addition of a suitable solvent.

A kit can include instructions for employing the kit components as well the use of any other reagent not included in the kit. Instructions can include variations that can be implemented.

In one aspect, the invention provides kits containing any one or more of the elements disclosed in the above methods and compositions. In some embodiments, a kit comprises a composition of the invention, in one or more containers. In some embodiments, the invention provides kits comprising adapters, primers, and/or other oligonucleotides described herein. In some embodiments, the kit further comprises one or more of: (a) a DNA ligase, (b) a DNA-dependent DNA polymerase, (c) an RNA-dependent DNA polymerase, (d) random primers, (e) primers comprising at least 4 thymidines at the 3' end, (f) a DNA endonuclease, (g) a DNA-dependent DNA polymerase, (h) one or more primers, each primer having one of a plurality of selected sequences, (i) a DNA kinase, (j) a DNA exonuclease, (k) magnetic beads, (l) an RNA ligase, and (m) one or more buffers suitable for one or more of the elements contained in said kit. The adapters, primers, other oligonucleotides, and reagents can be, without limitation, any of those described above. Elements of the kit can further be provided, without limitation, in any of the amounts and/or combinations (such as in the same kit or same container) described above. The kits may further comprise additional agents, such as those described above, for use according to the methods of the invention. The kit elements can be provided in any suitable container, including but not limited to plates, test tubes, vials, flasks, bottles, ampules, syringes, or the like. The agents can be provided in a form that may be directly used in the methods of the invention, or in a form that requires preparation prior to use, such as in the reconstitution of lyophilized agents. Agents may be provided in aliquots for single-use or as stocks from which multiple uses, such as in a number of reaction, may be obtained.

Computer Systems

Figure 12:
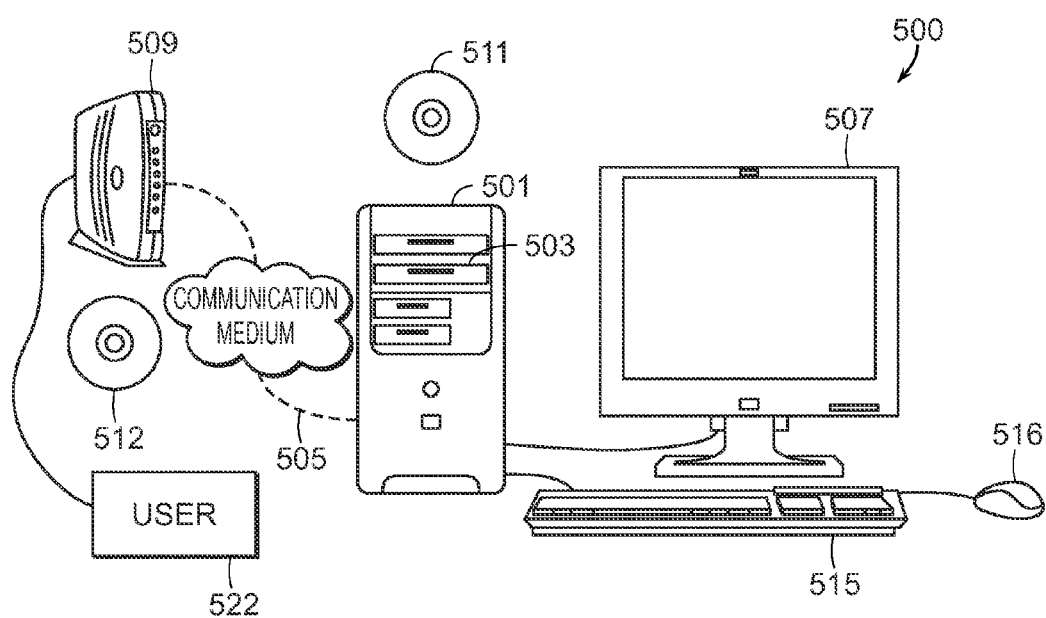
FIG. 12 illustrates various components of a generalized computer system according to some embodiments of the present invention.

The computer system 500 illustrated in FIG. 12 may be understood as a logical apparatus that can read instructions from media 511 and/or a network port 505, which can optionally be connected to server 509 having fixed media 512. The system, such as shown in FIG. 12 can include a CPU 501, disk drives 503, optional input devices such as keyboard 515 and/or mouse 516 and optional monitor 507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 522 as illustrated in FIG. 12.

Figure 13:
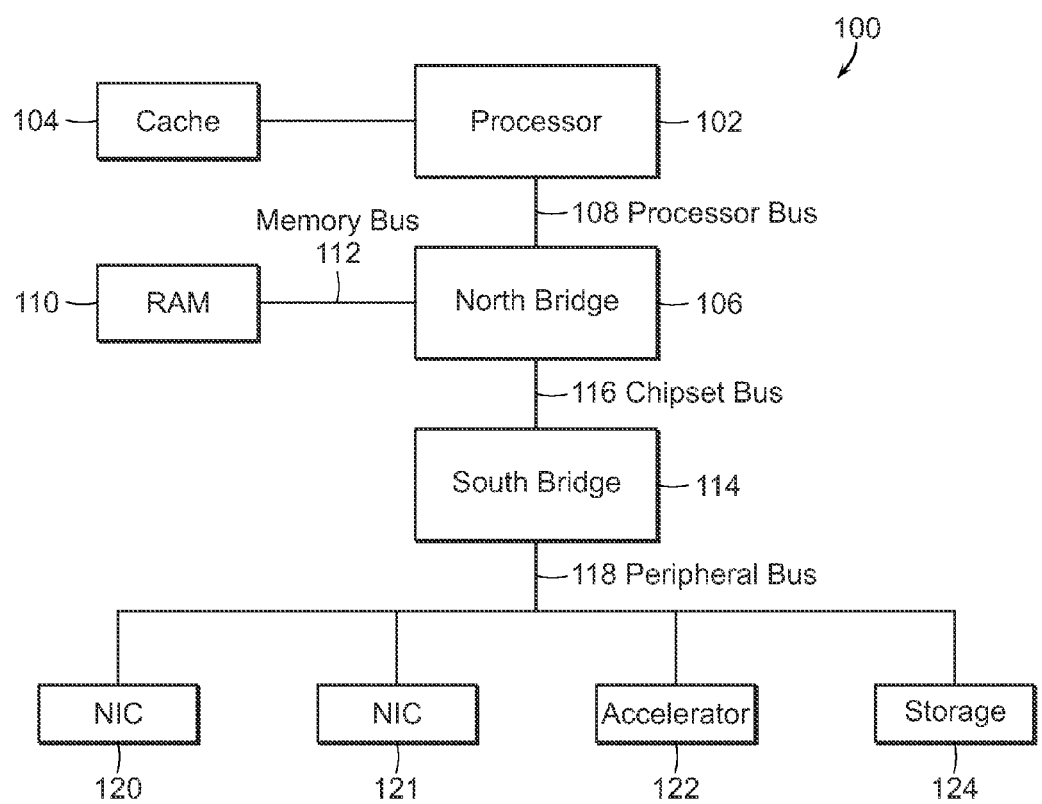
FIG. 13 is a block diagram illustrating an example architecture of a computer system that can be used in connection with example embodiments of the present invention.

FIG. 13 is a block diagram illustrating a first example architecture of a computer system 100 that can be used in connection with example embodiments of the present invention. As depicted in FIG. 13, the example computer system can include a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 13, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 14:
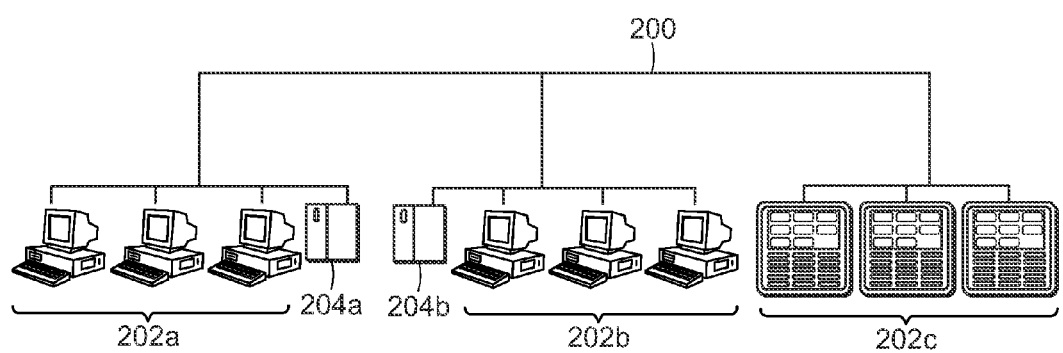
FIG. 14 is a diagram illustrating a computer network that can be used in connection with example embodiments of the present invention.

FIG. 14 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model can be used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 14 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 15:
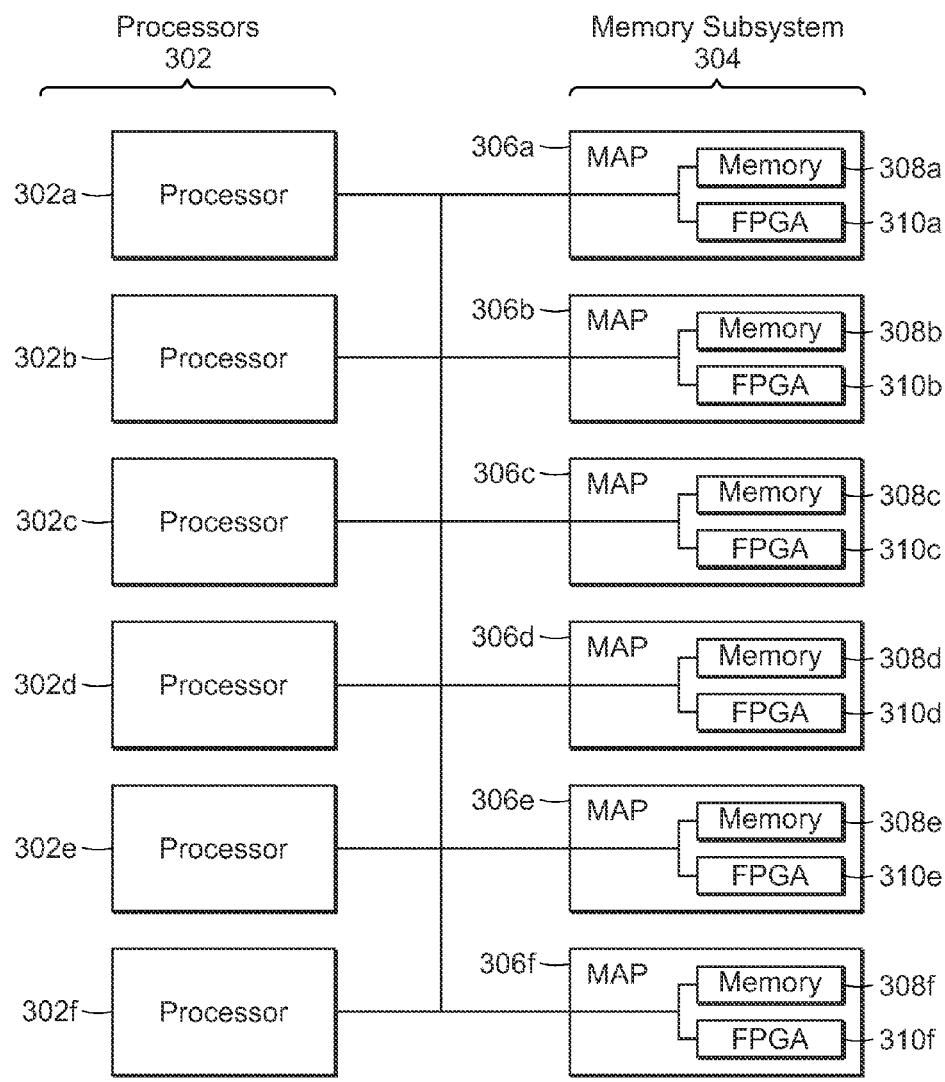
FIG. 15 is a block diagram illustrating another example architecture of a computer system that can be used in connection with example embodiments of the present invention.

FIG. 15 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 15, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 13.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein.

EXAMPLES

Example 1

Genome Assembly from Short Sequence Reads

An in vitro protocol was developed that allows amplification sequencing and reassembly of intermediate sized genomics fragments. In brief, genomic DNA was sheared to appropriate fragment size, amplification adapters were ligated at the ends of fragments, and the library was quantitated using qPCR to establish the number of amplifiable DNA fragments. The library was amplified library using adapter-specific primers with PCR after diluting the library to a necessary concentration. Amplification was carried out in independent wells of a PCR plate such that each well had an independent amplified population of molecules. The average number of molecules within each well was kept around 500-1000 to reduce complexity of unique DNA sequences, which is important to aid sequence assembly downstream. The resulting pool of amplified molecules were fragmented into a sequencing library using Nextera DNA transposase, and sequencing adapters with barcodes unique to each well were incorporated through limited cycle PCR. The library was then sequenced. After sequencing, reads were separated according to the barcodes and original long fragments were assembled using developed assembly algorithms described herein.

Methods of the invention allowed highly parallel preparation and sequencing of a large number of individual samples prepared from an artificially limited population of DNA molecules. The resulting complexity bottleneck was important for successful reassembly of the long DNA fragments.

Figure 2:
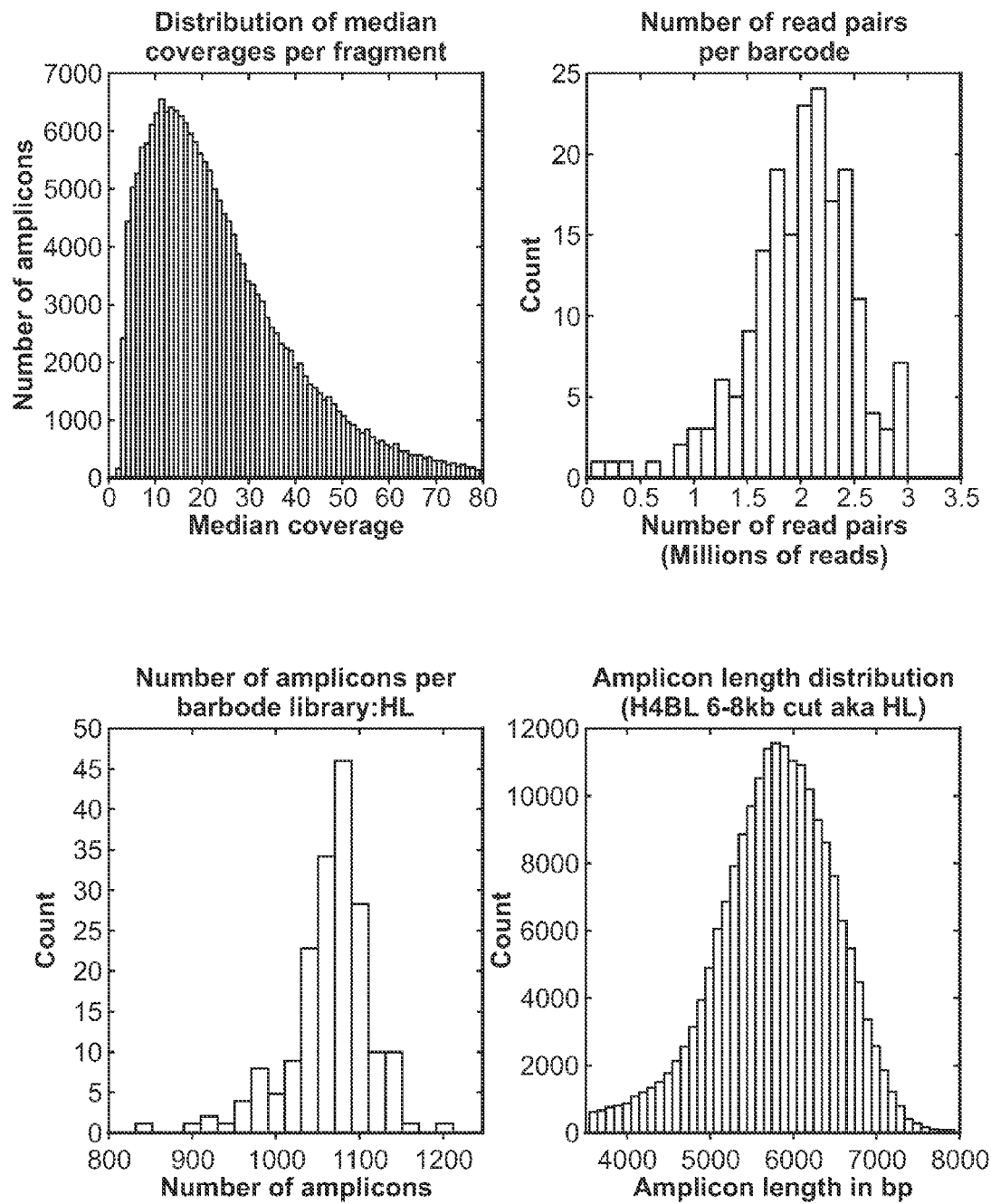
FIG. 2 is a set of graphs showing statistics for a sample, obtained by mapping reads to a reference genome.

To calibrate performance of the method, it was first applied it to sequencing of human genomic DNA. DNA was sheared to 4-8 kb, and a 5-7 kb gel cut was used as starting material for sample preparation. The Library was quantitated using qPCR relative to a set of previously sequenced standards and dilution was chosen to have a mean number of molecules around 1000. In this protocol, 192 barcodes were used, corresponding to wells of two 96 well plates. Barcodes were chosen such that to guarantee that all barcodes were at least two errors away from each other, and all reads that did not match exact barcode sequences were discarded. After sequencing, reads were aligned to a human genome reference, and it was established that an average number of distinct fragments was close to 1000. Fragment length distribution was found to be smaller than the initial gel cut, which can be explained by the fact that last few hundred base pairs from each fragment were underrepresented in the data due to the library construction method. Median coverage per fragment was around 20× which was sufficient to allow de-novo assembly of intermediate sized fragments (FIG. 2).

Figure 3:
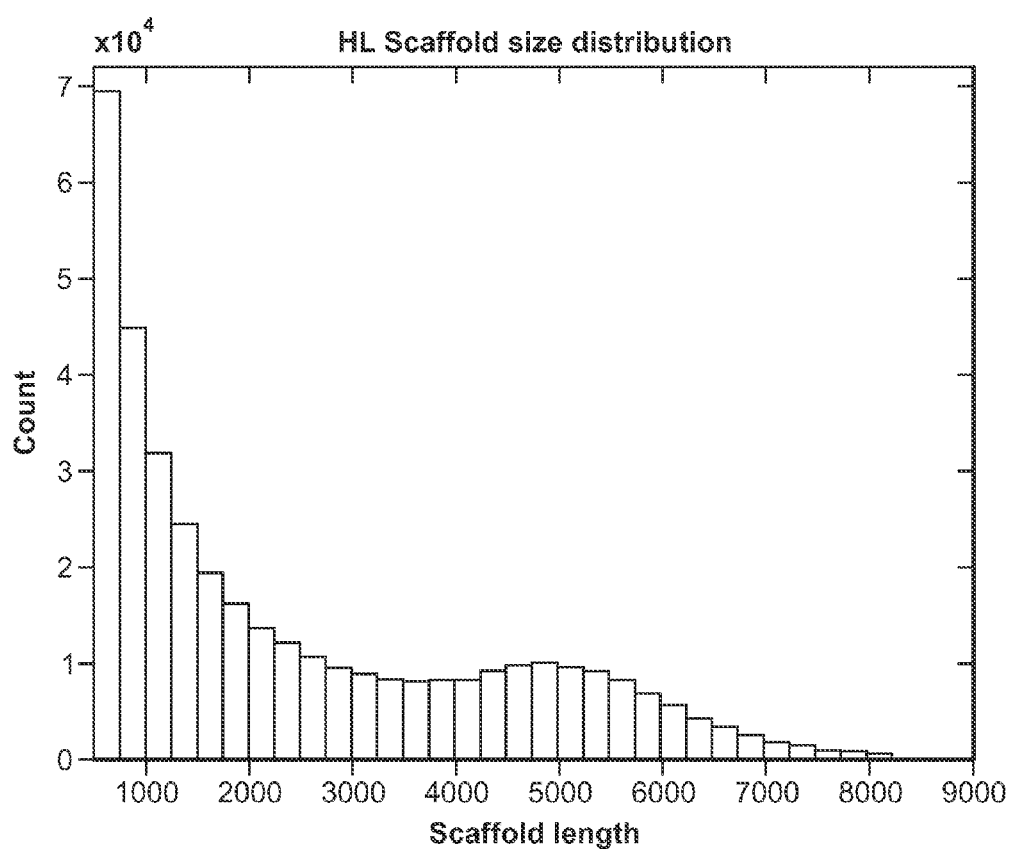
FIG. 3 is a graph showing assembly statistics.

Consensus sequences were assembled as described above. After assembly, a distribution of contigs with median size (N50) of approximately 3.5 kb was obtained. Complete reconstruction of full fragments was not possible for all intermediate sized fragments due to high repeat content of the human genome and variation of coverage due to sampling statistics; however, low frequency repeats were resolved using methods of the invention because it is unlikely that they will appear in multiple wells (FIG. 3).

Due to artificial dilution and amplification of limited amount of molecules, most of the fragments within each partitioned portion were a result of amplification of a fragment originating from a disjoint set of locations on the genome (otherwise overlaps would have been detected by coverage based analysis, or detecting heterozygous variants inconsistent with single molecule amplification, or by analysis of end markers embedded in the amplification adapters). This allowed haplotype-resolved variant calling to be performed by detecting variants using a pipeline that assumes haploid genome and "stitching together" overlapping fragments that share the same variants to obtain longer stretches of phased variants. This can be combined with haplotyping chips and bioinformatics approaches to extend continuous stretches of phased genome.

Figure 4:
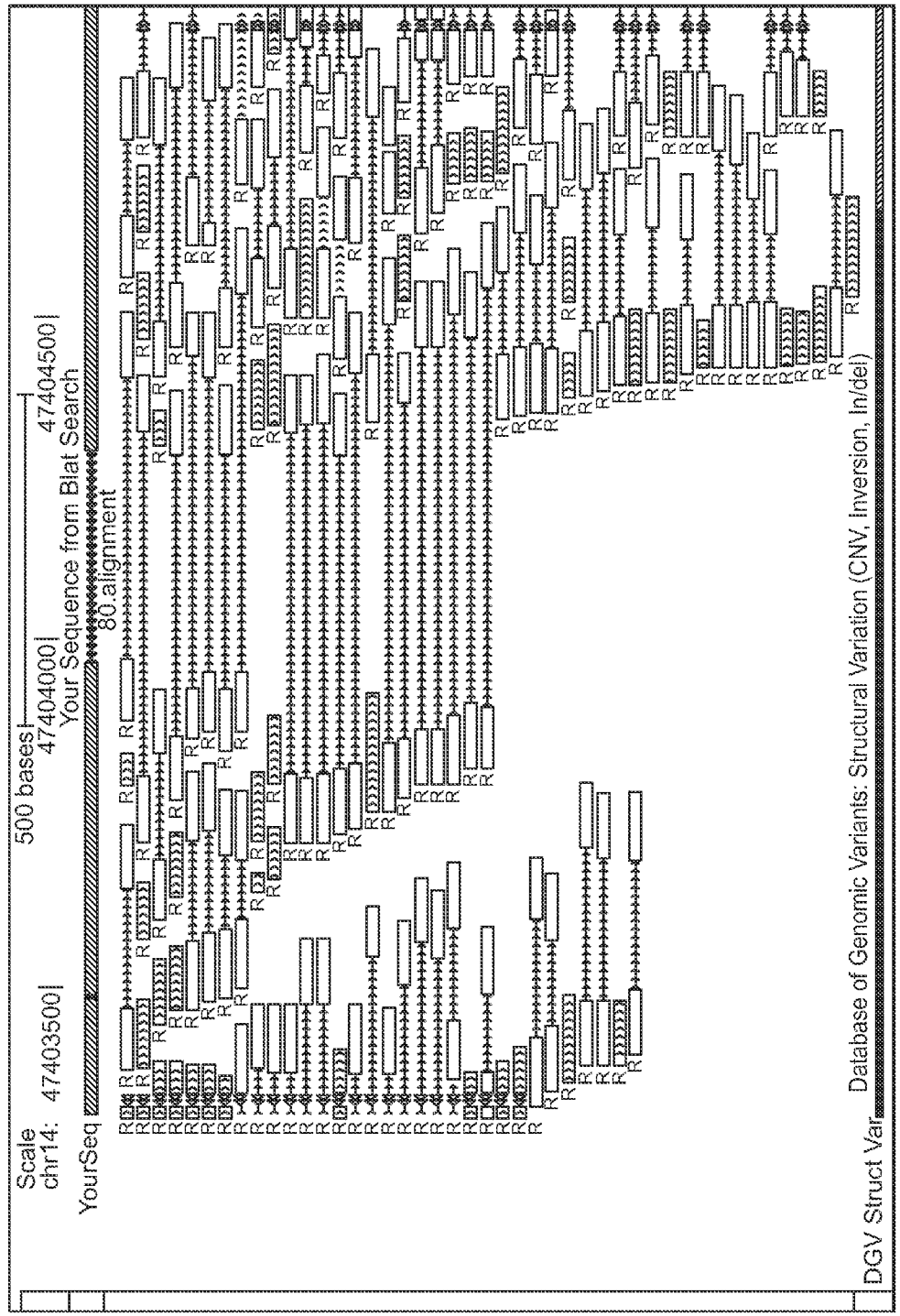
FIG. 4 shows structural variation detected using methods of the invention. Methods of the invention allowed detection of novel variants by comparing assembled long fragments with reference sequences. Single molecule amplification also allowed haplotype-resolved variant calling since each fragment originated from one of two chromosomes.

Methods of the invention were used to detect novel sequences by comparative analysis of assembled intermediate sized fragments (FIG. 4).

Example 2

Sample DNA Preparation

Genomic DNA was prepared using DNAeasy kit and sheared with HydroShear instrument to obtain DNA with size range around 10 kb. Sample was run on 0.8% e-gel to perform initial size selection to select band 7-10 kb band. Sample was analyzed using Agilent Bioanalyzer to confirm size distribution. DNA was treated with NEB end repair kit to obtain blunt end 5' phosphorylated ends.

Example 3

Repair Ends

A New England Biolabs end repair module was used to make blunt ends as follows. In 100 uL volume mix: 10 uL of 10× Neb next End repair reaction buffer, 5 uL of NEB Next End repair enzyme mix, 50 uL of eluted sample, and 35 uL of water. The mixture is incubated for 30 minutes at 20° C. and then purified on a Qiagen column. Elusion was performed in 30 ul water.

Example 4

Ligate Amplification Adaptors

A kit commercially available from 454 Life Sciences was used to ligate adapters onto the fragmented nucleic acid. The two sequence primers below were used:

```
Primer A1:
SEQ ID NO. 1:
5'-CCATCTCATCCCTGCGTGTCTCCGACTCAG-3'

SEQ ID NO. 2:
3'-TCTCCGACTCAG-5'

Primer B:
SEQ ID NO. 3:
5'-/5BioTEG/CCTATCCCCTGTGTGCCTTGGCAGTCTCAG-3'

SEQ ID NO. 4:
3'-TGGCAGTCTCAG-5'
```

Ligation was accomplished as follows. A mix of DNA 10 ul (450 ng); 2× ligation Buffer 20 ul; Adapter mix 5 ul; and Ligase 5 ul was incubated at 25° C. for 15 minutes.

Example 5

DNA Purification

Ampure beads purification was performed after ligation. The ratio of DNA to beads was 1:1.5 (Human DNA 40 ul:60 ul beads). The DNA and beads were gently vortexed by tapping on tube and incubated for 10 minutes. The tubes were then placed on a magnetic rack for 3 minutes and the supernatant was discarded. Two washed were performed with 70% ethanol without removing tubes from the rack. Most of the ethanol was removed and caps were removed from the tubes to allow for air drying until completely dry (approximately 5 minutes). Elution was performed in 25 μl of water. Incubation was for a few minutes and the supernatant was collected.

Example 6

Fill-in Reaction and Size Selection

A mixture of DNA 20 ul; 10× fill in buffer 2.5 ul; dNTP mix 1 ul; fill in polymerase 1.5 ul was prepared and incubated for 20 minutes at 37° C. 20 μL was transferred to the agarose gel and size selection was performed. Samples were cut from Qiagen gel and nucleic acid fragments eluted in 30 ul water.

Example 7

Quantitate Library Using qPCR

To quantitate, the sample library was compared to a reference library of known concentration, using LongAmp polymerase, and the same primer concentration that will be used for the amplification reaction. A mixture of 1.25 uL of 20× EvaGreen dye, 0.5 uL of Rox reference dye in 25 uL reaction volume was prepared. The qPCR was conducted according to the same thermocycling protocol as the used from the PCR reaction, see Table 2.

Example 8

PCR Amplification of Partitioned Nucleic Acids

The PCR reaction mixture is shown in Table 1 below.

TABLE 1

|  | 1 rxn | 220 rxn |
|---|---|---|
| LONGAMP-V2-LEFT (100 μm) | 0.1 μl | 20 μl |
| LONGAMP-V2-RIGHT (100 μm) | 0.1 μl | 20 μl |
| DNA | x (500 molecules) | x (110k molecules) |
| NEB LongAmp (M0287L) | 12.5 μl | 2750 μl |
| Water | 12.05 μl | 2673 μl |

SEQ ID NO. 5: LONGAMP-V2-LEFT 5'- CCA TCT CAT CCC TGC GTG TCT CCG -3'
SEQ ID NO. 6: LONGAMP-V2-RIGHT 5'- CCT ATC CCC TGT GTG CCT TGG CAG T -3'

The PCR reaction was conducted as follows. Two 96 half skirt plates were placed on ice to allow them to cool. The PCR cycler was set at 94° C. for preheating. To a 15 mL tube, was added water, both primers, and calculated amount of the sample. This mixture was vortexed rigorously, and placed on ice to cool down. 2× Enzyme master mix was added and the mixture was vortexed rigorously. 25 mL was transferred to a sterile container. Using an 8-channel pipette, the mixture was dispensed across all wells of both plates. The plates were covered with transparent PCR film, quickly spun, placed on the thermocycler, and the PCR reaction was conducted as shown in Table 2 below:

TABLE 2

| Step | Temperature | Time |
|---|---|---|
| 1 | 94 | 0:30 |
| 2 | 94 | 0:15 |
| 3 | 65 | 8:00 |
| 4 | Cycle to step 2 24 times | |
| 5 | 65 | 8:00 |
| 6 | 4 | hold |

Example 9

DNA Purification

A Zymo ZR-96 DNA clean and concentration (Zymogen D4024) kit was used for DNA purification. The two Zymo plates were assembled and the membrane plate was put on top of the collection plate. After the PCR reaction was finished 100 uL of the binding buffer was dispensed into each well and the PCR reaction contents were mixed with DNA binding buffer and transfer it to a Zymo plate. The plates were spun at 2200 g (or more) for 5 minutes, discarding the flow-through. 300 uL of the wash buffer was added to each well. The plates were spun again at 2200 g (or more) for 5 minutes, discarding the flow-through. 300 uL of the wash buffer was added to each well. The plates were spun again at 2200 g (or more) for 5 minutes.

The membrane plate was transferred to an elution plate and the collection plate was discarded. 12 uL of water was added to the middle of each membrane. The plates were spun at 2200 g (or more) for 5 minutes, use slower ramp-up speed (4 instead of 9).

Example 10

Fragmentation

The amplified nucleic acid is then fragmented. Each reaction had: 4 uL of DNA from the previous step eluted in water; 1 uL of 5× high molecular weight buffer, and 4 nL of nextera enzyme Illumina compatible 250 uL of high molecular weight buffer (HMW) and 10 uL of Nextera were combined in a 2 mL tube with enzyme. The mixture was vortexed, spun, and placed on ice. 4 uL from elution plates was transferred to new PCR plates directly to the bottom without touching the walls. 1 uL of the buffer-enzyme mixture was transferred to the walls of the 96 well plates, which were then covered with transparent PCR film. A quick spin down was performed to start the reaction, and the plates were vortexed while holding a rubber seal on the top to prevent cross-contamination between wells, followed by a second quick spin. The plates were placed on a cycler with a constant temperature of 55° C. for about 5 minutes. The plates were removed from the cycler and DNA binding buffer was added to each well. The purification was repeated as described above and elution plates were used to which 1 uL of 25×PCR primer mix designed to incorporate a custom set of bar code sequences according to the manufacturer recommendations was added.

Example 11

PCR Reaction

Two plates were placed on ice and 12.5 uL of 2× Phusion GC polymerase master mix (NEB M0532L) was transfer to the plates. All of the volume eluted after the fragmentation reaction was transferred to the wells. The plates contain: 1 uL of 25×PCR primer mix that was added to elution plates; 11.5 uL of DNA eluted in water after Nextera step; and 12.5 uL of 2× Phusion polymerase. The plates were covered with transparent PCR film, vortexed, and spun. The plates were then placed on a cycler and thermocycled as shown in Table 3.

TABLE 3

| Step | Temperature | Time |
| --- | --- | --- |
| 1 | 72 | 3:00 |
| 2 | 95 | 0:30 |
| 3 | 95 | 0:10 |
| 4 | 62 | 0:30 |
| 5 | 72 | 3:00 |
| 6 | Cycle to 4 for 8 more times | |
| 7 | 4 | hold |

Example 12

DNA purification

The amplified DNA was purified using the Quiagen 96-well plate vacuum protocol, which is commercially available from Qiagen. 80 uL of PM (DNA binding buffer for Qiagen 96WP purification kit) was added to each well. Well contents were mixed and the volume from all 192 wells was transferred to 25 ml tray. The contents of the tray were transferred to 50 mL tubes and vortexed. The contents were then transferred to 16 wells of 96 well plate purification system and placed on vacuum manifold. The vacuum is turned on and left running until the liquid is gone. 900 uL of PE buffer was added to each well, and the vacuum again was turned on until the liquid was gone. 900 uL of PE buffer was added again to each well and the vacuum again was turned on for 10 minutes. 60 uL of TE was added to the center of each well and let sit for 2 minutes, and the vacuum again was turned on for 5 minutes. All contents were transferred to a single 2 mL tube.

Example 13

Size Selection

The nucleic acid was then size selected using Egel Syber safe (2% agarose) gels. The gels were pre-run gel for 2 minutes. 8 middle lanes of the gels were loaded with 16 uL of the purified sample from last step, the next two lanes were filled with clean water, 16 uL of 30 ng/uL ladder was added to the nearby wells. The gels were run for 30 minutes, opened, and the band from 500-700 bp was cut from the gels. The DNA was purified using two Qiaquick columns and eluted in 35 uL of TE.

The purified DNA is then run again. Another 2% sybr safe gel was pre-run for 2 minutes. 4 lanes with purified sample from the first gel purification were loaded, water was loaded in nearby wells and two ladder wells. Gels were run for 30 minutes, opened, and the band from 500-700 bp was cut. The DNA was purified using two Qiaquick columns and eluted in 35 uL of TE.

Example 14

Quantitation

Quantitation (i.e., estimating number of molecules that can form clusters on Illumina flowcell) was performed with qPCR relative to a know standard previously characterized by direct DNA sequencing, using Agilent bioanalyzer, or using Fluidigm digital PCR to get absolute library quantitation.

Example 15

Bioinformatic Pipeline

After reads were obtained from sequencing instrument, they were subjected to a number of quality checks. First, sequences similar to the Nextera insertion sequences were detected and removed from ends of the reads. This situation may happen if distance between two read primers is less than read length, for example due to imperfect final gel purification. Second, quality trimming was then performed to remove ends of the reads that has quality less than a certain threshold, in this protocol, less than 15. Third, overlaps were detected between paired reads, if detected reads were combined in one single read and stored in a separate single read pool.

Reads were then split by bar code by matching indexing reads to a set of 192 7 bp bar codes. Bar codes were designed such that they were at least two sequencing errors away from each other which makes miscalls very unlikely. High quality reads resulting from this process were then mapped to a genome reference in order to perform haplotype-resolved variant calling and obtain basic quality statistics.

Another pipeline used high quality reads for de-novo fragment assembly. Reads with certain bar codes were first pre-processed to correct low frequency kmers that were a result of sequencing errors. Resulting read pools were assembled in contigs, paired end read information was then used to combine contigs in scaffolds and partially mapped reads were then used to fill gaps in scaffolds. Resulting scaffolds were then assembled into bigger scaffolds using de-novo assemblers designed to work with Sanger data to produce draft genome assembly.

What is claimed is:

1. A method for analyzing a plurality of target polynucleotides, the method comprising:
   (a) providing a sample comprising a plurality of target polynucleotide fragments, wherein each target polynucleotide fragment has a length of 5 kb to 40 kb;
   (b) performing a size selection on the plurality of target polynucleotide fragments to select 5-7 kb fragments;
   (c) ligating amplification adaptors at each end of at least a portion of the 5-7 kb fragments to produce a library of amplifiable fragments, wherein the adaptors serve as primer binding sites;
   (d) quantitating via qPCR to establish a number of amplifiable fragments in the library of amplifiable fragments;
   (e) determining a dilution factor based on the number of amplifiable fragments in the library of amplifiable fragments;
   (f) diluting and partitioning the library into a plurality of partitions based on the dilution factor such that each partition comprises, on average, a unique subset of 500 or more of the amplifiable fragments;
   (g) amplifying via polymerase chain reaction the partitioned amplifiable fragments;
   (h) subjecting the partitions to polynucleotide fragmentation thereby generating a set of smaller fragments; and
   (i) obtaining partial or complete sequence information from at least a subset of the smaller fragments.

2. A method for analyzing a plurality of target polynucleotides, the method comprising:
   (a) providing at least one sample comprising a plurality of target polynucleotide fragments, wherein each target polynucleotide fragment has of a length of 5 kb to 40 kb;
   (b) performing a size selection on the plurality of target polynucleotide fragments to select 5-7 kb fragments;
   (c) ligating amplification adaptors to each end of at least a portion of the 5-7 kb fragments to produce a library of amplifiable fragments, wherein the adaptor serves as a primer binding site;
   (d) quantitating via qPCR to establish a number of amplifiable fragments in the library of amplifiable fragments;
   (e) determining a dilution factor based on the number of amplifiable fragments in the library of amplifiable fragments;
   (f) diluting and partitioning the library based on the dilution factor into a plurality of partitions such that each partition comprises, on average, a unique subset of 500 or more of the amplifiable fragments;
   (g) amplifying via a polymerase chain reaction the partitioned amplifiable fragments;
   (h) subjecting the partitions to polynucleotide fragmentation thereby generating a set of smaller fragments;
   (i) coupling a partition specific barcode to at least a subset of the smaller fragments; and
   (j) obtaining partial or complete sequence information from at least a subset of the smaller fragments coupled with the partition specific barcodes.

3. The method of claim 1, wherein the adaptors coupled to each end of the 5-7 kb fragments comprise a first adaptor and a second adaptor, and the first adaptor is not the same as the second adaptor.

4. The method of claim 1, wherein the smaller fragments within a partition are labeled with one or more partition specific barcodes.

5. The method of claim 4, wherein the barcodes are nucleic acid sequences.

6. The method of claim 4, wherein the barcodes are greater than 3 nucleotides long.

7. The method of claim 4, wherein the barcodes are greater than 5 nucleotides long.

8. The method of claim 4, wherein the one or more partition specific barcodes comprise 2 barcodes that are each greater than 2 nucleotides long.

9. The method of claim 8, wherein all two partition specific barcodes comprise at least two differences in the nucleic acid sequence.

10. The method as in one of claims 1-2 wherein the sequence information comprises sequence reads obtained by sequencing.

11. The method as in one of claims 1-2, wherein the sequence information has an average accuracy of greater than 99%.

12. The method as in one of claims 1-2, wherein the sequence information has an average accuracy of greater than 95%.

13. The method as in one of claims 1-2, wherein the sequence information has an average accuracy of greater than 90%.

14. The method as in one of claims 1-2, wherein the sequence information has an average accuracy of greater than 80%.

15. The method of claim 10, wherein the sequence reads have an accuracy of greater than 99.98%.

16. The method of claim 10, wherein the sequence information spans more than 50 bp.

17. The method of claim 10, wherein the sequence information spans more than 100 bp.

18. The method of claim 10, wherein the sequence information spans more than 200 bp.

19. The method as in one of claims 1-2, wherein all sequence information is obtained in less than 1 month.

20. The method as in one of claims 1-2 wherein all sequence information is obtained in less than 2 weeks.

21. The method as in one of claims 1-2, wherein all sequence information is obtained in less than 1 week.

22. The method as in one of claims 1-2, wherein all sequence information is obtained in less than 1 day.

23. The method as in one of claims 1-2, wherein all sequence information is obtained in less than 3 hours.

24. The method as in one of claims 1-2, wherein all sequence information is obtained in less than 1 hour.

25. The method as in one of claims 1-2, wherein all sequence information is obtained in less than 30 minutes.

26. The method as in one of claims 1-2, wherein all sequence information is obtained in less than 10 minutes.

27. The method as in one of claims 1-2, wherein all sequence information is obtained in less than 5 minutes.

28. The method as in one of claims 1-2, wherein at least one target polynucleotide fragment within the sample is flagged if one or more of its sequence segments are substantially similar to one or more sequence segments of a second target polynucleotide fragment partitioned into the same partition.

29. The method as in one of claims 1-2, further comprising a sequence coverage of greater than 20 fold.

30. The method as in one of claims 1-2, further comprising an average sequence coverage of less than 500 fold.

31. The method of claim 10, wherein the sequencing comprises sequencing by synthesis.

32. The method of claim 10, wherein the sequencing comprises ion semiconductor sequencing.

33. The method of claim 10, wherein the sequencing comprises single molecule real time sequencing.

34. The method of claim 10, wherein the sequencing comprises nanopore sequencing.

35. The method of claim 10, wherein the sequencing comprises sequencing by electron microscopy.

36. The method as in one of claims 1-2, wherein the plurality of target polynucleotide fragments originates from genomic DNA.

37. The method of claim 36, wherein the genomic DNA originates from a polyploid genome.

38. The method as in one of claims 1-2, wherein at least one of the target polynucleotide fragments comprises a portion of a major histocompatibility complex gene.

39. The method as in one of claims 1-2, wherein at least one of the target polynucleotide fragments originates from fetal DNA.

40. The method of claim 10, wherein the sequencing comprises obtaining paired end reads.

41. The method as in one of claims 1-2, further comprising utilizing computing resources that are delivered over a network to improve detection of sequence variants and detection average accuracy.

42. The method as in one of claims 1-2, wherein the plurality of target polynucleotide fragments originate from a single molecule, and wherein the related sequence information links two or more positions on the single molecule.

43. The method of claim 42, wherein the two or more positions on the single molecule are separated by more than 5000 bp.

44. The method of claim 42, wherein the two or more positions on the single molecule are separated by more than 10000 bp.

45. The method as in one of claims 1-2, wherein the one or more target polynucleotide fragments comprise a first target polynucleotide and a second polynucleotide and the related sequence information to the first target polynucleotide and the related sequence information to the second target polynucleotide are linked.

46. The method as in one of claims 1-2, further comprising detecting a genomic structural variation.

47. The method as in one of claims 1-2, wherein the one or more target polynucleotide fragments originate from one or more tissue samples, wherein relating sequence information comprises detecting a plurality of sequence variants in the one or more tissue samples, and wherein the plurality of sequence variants from one or more tissue sample are compared.

48. The method as in one of claims 1-2, further comprising providing a diagnosis based on the related sequence information.

49. The method of claim 48, wherein the diagnosis is directed to a disease selected from the group consisting of allergic rhinitis, allergic conjunctivitis, allergic asthma, atopic eczema, atopic dermatitis, food allergy, severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects, rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens, hemangiomatosis in newborns, secondary progressive multiple sclerosis, chronic progressive myelodegenerative disease, neurofibromatosis, ganglioneuromatosis, keloid formation, Paget's Disease of the bone, fibrocystic disease (e.g., of the breast or uterus), sarcoidosis, Peronies and Duputren's fibrosis, cirrhosis, atherosclerosis and vascular restenosis, hematologic malignancies and solid tumors, 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

50. The method as in one of claims 1-2, wherein the one or more target polynucleotide fragments comprise at least a first target polynucleotide adjacent to a first known nucleotide sequence at at least one end and a second target polynucleotide adjacent to a second known nucleotide sequence at at least one end, wherein the first known nucleotide sequence is not the same as the second known nucleotide sequence.

51. The method of claim 50, wherein the first target polynucleotide further comprises a third known nucleotide sequence at at least one end, wherein the second target polynucleotide further comprises a fourth known nucleotide sequence at at least one end, wherein the third known nucleotide sequence is dependent on the first known nucleotide sequence and wherein the fourth known nucleotide sequence is dependent on the second known nucleotide sequence.

52. The method of claim 51, wherein relating sequence information from the plurality of fragments into the first target polynucleotide comprises linking the first and the third known nucleotide sequences.

53. The method of claim 52, wherein the first and third known nucleotide sequences are different from the second and fourth known nucleotide sequences.

54. The method as in one of claims 1-2, further comprising identifying the presence of a pathogen in the at least one sample.

55. The method of claim 54, wherein the pathogen is selected from the group consisting of a bacterial agent, a virus, a parasite, and a fungus.

56. The method of claim 55, wherein the bacterial agent is selected from the group consisting of *Escherichia coli, Salmonella, Shigella, Klebsiella Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia, B-Hemolytic strep., Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

57. The method of claim 55, wherein the fungus is selected from the group consisting of *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

58. The method of claim 55, wherein the virus is selected from the group consisting of human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

59. The method of claim 55, wherein the parasite is selected from the group consisting of *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidum, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii*, and *Necator americanis*.

60. The method of claim 54, wherein the pathogen comprises a drug resistant pathogen.

61. The method of claim 60, wherein the drug resistant pathogen is selected from the group consisting of vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus.

62. The method of claim 1, wherein the quantitating via qPCR and the amplifying via polymerase chain reaction both use the primer binding sites provided by the adaptors on the amplifiable fragments.

63. The method of claim 2, wherein the quantitating via qPCR and the amplifying via polymerase chain reaction both use the primer binding sites provided by the adaptors on the amplifiable fragments.

* * * * *

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 1
ccatctcatc cctgcgtgtc tccgactcag                                       30

<210> SEQ ID NO 2
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 2
tctccgactc ag                                                          12

<210> SEQ ID NO 3
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 3
cctatcccct gtgtgccttg gcagtctcag                                       30

<210> SEQ ID NO 4
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 4
tggcagtctc ag                                                          12

<210> SEQ ID NO 5
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 5
ccatctcatc cctgcgtgtc tccg                                             24

<210> SEQ ID NO 6
<211> LENGTH: 25
<212> TYPE: DNA
```

```
<213> ORGANISM: Artificial Sequence
<220> FEATURE:
<223> OTHER INFORMATION: Synthetic Sequence

<400> SEQUENCE: 6
cctatcccct gtgtgccttg gcagt                                              25
```